(12) United States Patent
Oeth et al.

(10) Patent No.: US 8,709,726 B2
(45) Date of Patent: Apr. 29, 2014

(54) NUCLEIC ACID-BASED TESTS FOR PRENATAL GENDER DETERMINATION

(75) Inventors: Paul Andrew Oeth, San Diego, CA (US); Payam Mahboubi, San Diego, CA (US); Min Seob Lee, San Diego, CA (US)

(73) Assignee: Sequenom, Inc., San Diego, CA (US)

( * ) Notice: Subject to any disclaimer, the term of this patent is extended or adjusted under 35 U.S.C. 154(b) by 268 days.

(21) Appl. No.: 12/401,493

(22) Filed: Mar. 10, 2009

(65) Prior Publication Data

US 2009/0317817 A1 Dec. 24, 2009

Related U.S. Application Data

(60) Provisional application No. 61/035,711, filed on Mar. 11, 2008.

(51) Int. Cl.
*C12Q 1/68* (2006.01)
*C12P 19/34* (2006.01)
*C07H 21/04* (2006.01)

(52) U.S. Cl.
USPC ................. 435/6.12; 435/91.2; 536/24.3

(58) Field of Classification Search
None
See application file for complete search history.

(56) References Cited

U.S. PATENT DOCUMENTS

| | | | |
|---|---|---|---|
| 4,109,496 A | 8/1978 | Allemann et al. |
| 4,179,337 A | 12/1979 | Davis et al. |
| 4,458,066 A | 7/1984 | Caruthers et al. |
| 4,469,863 A | 9/1984 | Ts'o et al. |
| 4,522,811 A | 6/1985 | Eppstein et al. |
| 4,656,127 A | 4/1987 | Mundy |
| 4,676,980 A | 6/1987 | Segal et al. |
| 4,683,195 A | 7/1987 | Mullis et al. |
| 4,683,202 A | 7/1987 | Mullis |
| 4,851,331 A | 7/1989 | Vary et al. |
| 4,868,103 A | 9/1989 | Stavrianopoulos et al. |
| 4,873,316 A | 10/1989 | Meade et al. |
| 4,965,188 A | 10/1990 | Mullis et al. |
| 5,048,530 A | 9/1991 | Hurwitz |
| 5,075,212 A | 12/1991 | Rotbart |
| 5,118,937 A | 6/1992 | Hillenkamp et al. |
| 5,210,015 A | 5/1993 | Gelfand et al. |
| 5,272,071 A | 12/1993 | Chappel et al. |
| 5,283,317 A | 2/1994 | Saifer et al. |
| 5,487,972 A | 1/1996 | Gelfand et al. |
| 5,492,806 A | 2/1996 | Drmanac et al. |
| 5,525,464 A | 6/1996 | Drmanac et al. |
| 5,536,821 A | 7/1996 | Agrawal et al. |
| 5,541,306 A | 7/1996 | Agrawal et al. |
| 5,547,835 A | 8/1996 | Koster |
| 5,589,330 A | 12/1996 | Shuber |
| 5,605,798 A | 2/1997 | Koster |
| 5,614,622 A | 3/1997 | Iyer et al. |
| 5,631,169 A | 5/1997 | Lakowicz et al. |
| 5,637,683 A | 6/1997 | Usher et al. |
| 5,637,684 A | 6/1997 | Cook |
| 5,656,493 A | 8/1997 | Mullis et al. |
| 5,679,524 A | 10/1997 | Nikiforov et al. |
| 5,691,141 A | 11/1997 | Koster |
| 5,695,940 A | 12/1997 | Drmanac et al. |
| 5,700,922 A | 12/1997 | Cook |
| 5,717,083 A | 2/1998 | Cook et al. |
| 5,719,262 A | 2/1998 | Buchardt et al. |
| 5,720,928 A | 2/1998 | Schwartz |
| 5,739,308 A | 4/1998 | Kandimalla et al. |
| 5,739,314 A | 4/1998 | Roy et al. |
| 5,766,849 A | 6/1998 | McDonough et al. |
| 5,773,601 A | 6/1998 | Agrawal |
| 5,786,146 A | 7/1998 | Herman et al. |
| 5,834,189 A | 11/1998 | Stevens et al. |
| 5,849,483 A | 12/1998 | Shuber |
| 5,849,497 A | 12/1998 | Steinman |
| 5,849,542 A | 12/1998 | Reeve et al. |
| 5,849,546 A | 12/1998 | Sousa et al. |
| 5,851,770 A | 12/1998 | Babon et al. |
| 5,869,242 A | 2/1999 | Kamb |
| 5,876,934 A | 3/1999 | Duthie et al. |
| 5,886,165 A | 3/1999 | Kandimalla et al. |
| 5,891,625 A | 4/1999 | Buchardt et al. |
| 5,908,755 A | 6/1999 | Kumar et al. |
| 5,912,118 A | 6/1999 | Ansorge et al. |
| 5,928,906 A | 7/1999 | Koster et al. |
| 5,929,226 A | 7/1999 | Padmapriya et al. |
| 5,952,174 A | 9/1999 | Nikiforov et al. |
| 5,955,599 A | 9/1999 | Iyer et al. |
| 5,958,692 A | 9/1999 | Cotton et al. |
| 5,962,674 A | 10/1999 | Iyer et al. |
| 5,976,802 A | 11/1999 | Ansorge et al. |

(Continued)

FOREIGN PATENT DOCUMENTS

EP 264166 4/1988
EP 0401384 12/1990

(Continued)

OTHER PUBLICATIONS

Lowe et al. A computer program for selection of oligonucleotide primers for polymerase chain reactions. Nucleic Acids Res. (1990) vol. 18, No. 7, pp. 1757-1761.*

(Continued)

*Primary Examiner* — Gary Benzion
*Assistant Examiner* — David Thomas
(74) *Attorney, Agent, or Firm* — Grant Anderson LLP

(57) ABSTRACT

Provided herein are compositions, processes and kits for non-invasive, early determination of fetal sex from, and/or amount of fetal nucleic acid in, an extracellular nucleic acid sample from a pregnant female. Such compositions, processes and kits are useful for detection of low genomic copy numbers of male fetal nucleic acid in a high copy number background of female nucleic acid, thereby determining the sex of a fetus and/or amount of fetal nucleic acid in a sample.

27 Claims, 7 Drawing Sheets

(56) References Cited

U.S. PATENT DOCUMENTS

| | | |
|---|---|---|
| 5,977,296 A | 11/1999 | Nielsen et al. |
| 5,981,186 A | 11/1999 | Gabe et al. |
| 5,998,143 A | 12/1999 | Ellis et al. |
| 6,004,744 A | 12/1999 | Goelet et al. |
| 6,013,431 A | 1/2000 | Soderlund et al. |
| 6,013,499 A | 1/2000 | Narumiya et al. |
| 6,017,702 A | 1/2000 | Lee et al. |
| 6,018,041 A | 1/2000 | Drmanac et al. |
| 6,024,925 A | 2/2000 | Little et al. |
| 6,043,031 A | 3/2000 | Koster et al. |
| 6,045,996 A | 4/2000 | Cronin et al. |
| 6,046,005 A | 4/2000 | Ju et al. |
| 6,057,134 A | 5/2000 | Lader et al. |
| 6,087,095 A | 7/2000 | Rosenthal et al. |
| 6,107,037 A | 8/2000 | Sousa et al. |
| 6,110,684 A | 8/2000 | Kemper et al. |
| 6,117,992 A | 9/2000 | Iyer |
| 6,136,541 A | 10/2000 | Gulati |
| 6,140,053 A | 10/2000 | Koster |
| 6,140,054 A | 10/2000 | Wittwer et al. |
| 6,140,482 A | 10/2000 | Iyer et al. |
| 6,142,681 A | 11/2000 | Gulati |
| 6,143,496 A | 11/2000 | Brown et al. |
| 6,156,501 A | 12/2000 | McGall et al. |
| 6,183,958 B1 | 2/2001 | Stanton, Jr. |
| 6,194,144 B1 | 2/2001 | Koster |
| 6,194,180 B1 | 2/2001 | Joyce |
| 6,197,506 B1 | 3/2001 | Fodor et al. |
| 6,210,574 B1 | 4/2001 | Sammons et al. |
| 6,210,891 B1 | 4/2001 | Nyren et al. |
| 6,214,556 B1 | 4/2001 | Olek et al. |
| 6,214,560 B1 | 4/2001 | Yguerabide et al. |
| 6,223,127 B1 | 4/2001 | Berno |
| 6,225,625 B1 | 5/2001 | Pirrung et al. |
| 6,229,911 B1 | 5/2001 | Balaban et al. |
| 6,239,273 B1 | 5/2001 | Pease et al. |
| 6,251,638 B1 | 6/2001 | Umansky et al. |
| 6,258,538 B1 | 7/2001 | Koster et al. |
| 6,258,540 B1 | 7/2001 | Lo et al. |
| 6,297,028 B1 | 10/2001 | Taniguchi et al. |
| 6,326,174 B1 | 12/2001 | Joyce et al. |
| 6,368,834 B1 | 4/2002 | Senapathy et al. |
| 6,440,706 B1 | 8/2002 | Vogelstein et al. |
| 6,468,748 B1 | 10/2002 | Monforte et al. |
| 6,610,492 B1 | 8/2003 | Stanton, Jr. et al. |
| 6,664,056 B2 | 12/2003 | Lo et al. |
| 6,723,513 B2 | 4/2004 | Lexow |
| 6,759,217 B2 * | 7/2004 | Kopreski ............. 435/91.2 |
| 6,818,394 B1 | 11/2004 | O'Donnell-Maloney et al. |
| 6,884,586 B2 | 4/2005 | Van Ness et al. |
| 6,916,634 B2 | 7/2005 | Kopreski |
| 6,927,028 B2 | 8/2005 | Dennis et al. |
| 6,929,911 B2 * | 8/2005 | Oefner et al. ............. 435/6.1 |
| 7,081,339 B2 | 7/2006 | Slepnev |
| 7,169,314 B2 | 1/2007 | Unger et al. |
| 7,244,567 B2 | 7/2007 | Chen et al. |
| 7,253,259 B2 * | 8/2007 | Otagiri et al. ............. 530/350 |
| 7,285,422 B1 | 10/2007 | Little et al. |
| 7,468,249 B2 | 12/2008 | Xie et al. |
| 7,655,399 B2 | 2/2010 | Cantor et al. |
| 7,709,262 B2 | 5/2010 | Cantor et al. |
| 7,785,798 B2 | 8/2010 | Cantor et al. |
| 2001/0008615 A1 | 7/2001 | Little et al. |
| 2001/0051341 A1 | 12/2001 | Lo et al. |
| 2002/0006621 A1 | 1/2002 | Bianchi |
| 2003/0022207 A1 | 1/2003 | Balasubramanian et al. |
| 2003/0082600 A1 | 5/2003 | Olek et al. |
| 2003/0087276 A1 | 5/2003 | Kopreski |
| 2003/0096426 A1 | 5/2003 | Little et al. |
| 2003/0180748 A1 | 9/2003 | Braun et al. |
| 2003/0180779 A1 | 9/2003 | Lofton-Day et al. |
| 2003/0211483 A1 | 11/2003 | Schroeder et al. |
| 2003/0211522 A1 | 11/2003 | Landes et al. |
| 2004/0014105 A1 | 1/2004 | Schroeder et al. |
| 2004/0081993 A1 | 4/2004 | Cantor et al. |
| 2004/0115684 A1 | 6/2004 | Costa |
| 2004/0137470 A1 | 7/2004 | Dhallan |
| 2004/0203037 A1 | 10/2004 | Lo et al. |
| 2005/0009059 A1 | 1/2005 | Shapero et al. |
| 2005/0019762 A1 | 1/2005 | Olek |
| 2005/0037388 A1 | 2/2005 | Antonarakis et al. |
| 2005/0059003 A1 | 3/2005 | Enoki et al. |
| 2005/0064406 A1 | 3/2005 | Zabarobsky et al. |
| 2005/0064428 A1 | 3/2005 | Berlin |
| 2005/0069879 A1 | 3/2005 | Berlin |
| 2005/0079521 A1 | 4/2005 | Beaulieu et al. |
| 2005/0112590 A1 | 5/2005 | Boom et al. |
| 2005/0153316 A1 | 7/2005 | Jeddeloh et al. |
| 2005/0153347 A1 | 7/2005 | Shapero et al. |
| 2005/0164241 A1 | 7/2005 | Hahn et al. |
| 2005/0266473 A1 | 12/2005 | Zhang et al. |
| 2005/0272070 A1 | 12/2005 | Ehrich et al. |
| 2005/0287592 A1 | 12/2005 | Kless |
| 2006/0019278 A1 | 1/2006 | Lo et al. |
| 2006/0094039 A1 | 5/2006 | Rosenfeld et al. |
| 2006/0136142 A1 | 6/2006 | Berlin et al. |
| 2006/0160105 A1 | 7/2006 | Dhallan |
| 2006/0166228 A1 * | 7/2006 | Page et al. ............. 435/6 |
| 2006/0210992 A1 | 9/2006 | van den Boom |
| 2006/0252068 A1 | 11/2006 | Lo et al. |
| 2006/0252071 A1 | 11/2006 | Lo et al. |
| 2007/0048755 A1 * | 3/2007 | Di Fiore ............. 435/6 |
| 2007/0059707 A1 | 3/2007 | Cantor et al. |
| 2007/0065823 A1 | 3/2007 | Dressman et al. |
| 2007/0111233 A1 | 5/2007 | Bianchi et al. |
| 2007/0202525 A1 | 8/2007 | Quake et al. |
| 2007/0207466 A1 | 9/2007 | Cantor et al. |
| 2007/0212689 A1 | 9/2007 | Bianchi et al. |
| 2007/0243549 A1 | 10/2007 | Bischoff |
| 2007/0275402 A1 | 11/2007 | Lo et al. |
| 2008/0020390 A1 | 1/2008 | Mitchell et al. |
| 2008/0070792 A1 | 3/2008 | Stoughton et al. |
| 2008/0096766 A1 | 4/2008 | Lee |
| 2008/0299562 A1 | 12/2008 | Oeth |
| 2008/0305479 A1 | 12/2008 | van den Boom |
| 2009/0026082 A1 | 1/2009 | Rothberg et al. |
| 2009/0029377 A1 | 1/2009 | Lo et al. |
| 2009/0061425 A1 | 3/2009 | Lo et al. |
| 2009/0111712 A1 | 4/2009 | Van Den Boom et al. |
| 2009/0142755 A1 | 6/2009 | Albitar |
| 2009/0202984 A1 | 8/2009 | Cantor |
| 2009/0317817 A1 | 12/2009 | Oeth et al. |
| 2009/0317818 A1 | 12/2009 | Ehrich et al. |
| 2010/0105049 A1 | 4/2010 | Ehrich et al. |
| 2010/0184046 A1 | 7/2010 | Klass et al. |
| 2010/0203529 A1 | 8/2010 | Kuslich et al. |
| 2010/0227320 A1 | 9/2010 | Fu |
| 2010/0240054 A1 | 9/2010 | Bischoff |
| 2010/0273165 A1 | 10/2010 | Ehrich et al. |
| 2010/0279295 A1 | 11/2010 | Roy et al. |
| 2011/0033851 A1 | 2/2011 | Rand |
| 2011/0105353 A1 | 5/2011 | Lo et al. |
| 2011/0151460 A1 | 6/2011 | Klass et al. |
| 2011/0177517 A1 | 7/2011 | Rava et al. |
| 2011/0178719 A1 | 7/2011 | Rabinowirz et al. |
| 2011/0201507 A1 | 8/2011 | Rava et al. |
| 2011/0212846 A1 | 9/2011 | Spier |
| 2011/0224087 A1 | 9/2011 | Quake et al. |
| 2011/0276277 A1 | 11/2011 | Lo et al. |
| 2011/0288780 A1 | 11/2011 | Rabinowirz et al. |
| 2012/0264618 A1 | 10/2012 | Nygren |
| 2012/0276542 A1 | 11/2012 | Nygren |

FOREIGN PATENT DOCUMENTS

| | | |
|---|---|---|
| EP | 1524321 | 4/2005 |
| EP | 1 373 561 | 2/2009 |
| WO | WO 91/06667 | 5/1991 |
| WO | WO 94/10300 | 5/1994 |
| WO | WO 97/12058 | 4/1997 |
| WO | WO 97/35589 | 10/1997 |
| WO | WO 97/37041 | 10/1997 |
| WO | WO 98/20020 | 5/1998 |
| WO | WO 98/22489 | 5/1998 |

(56) References Cited

FOREIGN PATENT DOCUMENTS

| | | |
|---|---|---|
| WO | WO 98/39352 | 9/1998 |
| WO | WO 98/39474 | 9/1998 |
| WO | WO 98/54364 | 12/1998 |
| WO | WO 99/57318 | 5/1999 |
| WO | WO 00/52625 | 9/2000 |
| WO | WO 00/56746 | 9/2000 |
| WO | WO 00/66771 | 11/2000 |
| WO | WO 00/75372 | 12/2000 |
| WO | WO 01/14398 | 3/2001 |
| WO | WO 01/20039 | 3/2001 |
| WO | WO 01/25485 | 4/2001 |
| WO | WO 01/27326 | 4/2001 |
| WO | WO 01/27327 | 4/2001 |
| WO | WO 01/27329 | 4/2001 |
| WO | WO 01/29259 | 4/2001 |
| WO | WO 02/18616 | 3/2002 |
| WO | WO 02/086163 | 10/2002 |
| WO | WO 03/000919 | 1/2003 |
| WO | WO 03/057909 | 7/2003 |
| WO | WO 03/062441 | 7/2003 |
| WO | WO 03/080863 | 10/2003 |
| WO | WO 2004/013284 | 2/2004 |
| WO | WO 2004/076653 | 9/2004 |
| WO | WO 2005/012578 | 2/2005 |
| WO | WO 2005/021793 | 3/2005 |
| WO | WO 2005/023091 | 3/2005 |
| WO | WO 2005/035725 | 4/2005 |
| WO | WO 2005/040399 | 5/2005 |
| WO | WO 2005/098050 | 10/2005 |
| WO | WO 2006/056480 | 6/2006 |
| WO | WO 2006/097049 | 9/2006 |
| WO | WO 2006/097051 | 9/2006 |
| WO | WO 2007/016668 | 2/2007 |
| WO | WO 2007/028155 | 3/2007 |
| WO | WO 2007/092473 | 8/2007 |
| WO | WO 2007/121276 | 10/2007 |
| WO | WO 2007/132166 | 11/2007 |
| WO | WO 2007/132167 | 11/2007 |
| WO | WO 2007/140417 | 12/2007 |
| WO | WO 2007/147063 | 12/2007 |
| WO | WO 2008/098142 | 8/2008 |
| WO | WO 2008/103761 | 8/2008 |
| WO | WO 2008/103763 | 8/2008 |
| WO | WO 2008/118988 | 10/2008 |
| WO | WO 2008/157264 | 12/2008 |
| WO | WO 2009/032779 | 3/2009 |
| WO | WO 2009/032781 | 3/2009 |
| WO | WO 2009/046445 | 4/2009 |
| WO | WO 2009/091934 | 7/2009 |
| WO | WO 2009/114543 | 9/2009 |
| WO | WO 2010/004265 | 1/2010 |
| WO | WO 2010/033639 | 3/2010 |
| WO | WO 2010/065470 | 6/2010 |
| WO | WO 2010/115016 | 10/2010 |
| WO | WO 2011/034631 | 3/2011 |
| WO | WO 2011/087760 | 7/2011 |
| WO | WO 2011/091063 | 7/2011 |
| WO | WO 2011/092592 | 8/2011 |
| WO | WO 2011/142836 | 11/2011 |
| WO | WO 2011/143659 | 11/2011 |
| WO | WO 2012/118745 | 9/2012 |
| WO | WO 2012/149339 | 11/2012 |
| WO | WO 2013/052913 | 4/2013 |
| WO | WO 2013/055817 | 4/2013 |

OTHER PUBLICATIONS

Swinkels et al. Hemolysis, elevated liver enzymes, and low platelet count (HELLP) syndrome as a complication of pre-eclampsia in pregnant women increases the amount of cell-free fetal and maternal DNA in maternal plasma and serum. Clinical Chem. (2002) vol. 48, No. 4, pp. 650-653.*
Invitation to Pay Additional Fees and Partial International Search Report mailed on: Dec. 28, 2009 in International application No. PCT/US2009/036683 filed on: Mar. 10, 2009 and published as WO 09/114543 on Sep. 17, 2009.
U.S. Appl. No. 12/354,749, filed Jan. 15, 2009, Cantor.
Anantha, et al., Biochemistry (1998) 37:2709 2714; and Qu & Chaires, Methods Enzymol. (2000) 321:353 369.
Beaucage and Caruthers, Tetrahedron Letts., 22:1859-1862, 1981.
Boom et al., 1991, J. Clin. Microbiol. 29: 1804-1811.
Boom et al., 1990, J. Clin. Microbiol. 28: 495-503.
Braslavsky et al., PNAS 100(7): 3960-3964 (2003).
Chen & Kwok, Nucleic Acids Research 25: 347-353 (1997).
Chen et al., Proc. Natl. Acad. Sci. USA 94/20: 10756-10761 (1997).
Cheung et al. (1994, J. Clin. Microbiol. 32: 2593-2597).
Chirgwin et al. (1979, Biochem. 18: 5294-5299.
Chomczynski and Mackey 1995, Anal. Biochem. 225: 163-164.
Chomczynski and Mackey 1995, Biotechniques 19: 942-945.
Chomczynski and Sacchi 1987, Analytical Biochem. 162: 156-159.
Chomczynski, 1993, Biotech. 15: 532-537.
Chow, K.C., et al., Mass Spectrometric detection of a SNP panel as an internal positive control for fetal DNA analysis in maternal plasma. Clin. Chem. 53, 141-142 (2007).
Current Protocols in Molecular Biology, John Wiley & Sons, N.Y., 6.3.1-6.3.6 (1989).
Dear Brief Funct Genomic Proteomic 2003; 1: 397-416.
Egger et al., J. Clin. Microbiol. 33:1442-1447, 1995.
Fournie et al., 1986 Anal. Biochem. 158: 250-256.
Grompe et al., Proc. Natl. Acad. Sci. USA 86: 5855-5892 (1989).
Grompe, Nature Genetics 5: 111-117 (1993).
Haase et al., Methods in Virology, vol. 7, pp. 189-226, 1984.
Hames and Higgins eds., Nucleic Acid Hybridization: A Practical Approach, IRL Press, 1987.
Harris TD et al. 2008 Science, 320, 106-109.
Hill, "Transcription-mediated amplification" (TMA) described at World Wide Web URL "gen-probe.com/pdfs/tma_whiteppr.pdf").
Jurinke, C., et al., "MALDI-TOF mass spectrometry: a versatile tool for high-performance DNA analysis." Mol. Biotechnol. 26, 147-164 (2004).
Kalinina et al., "Nanoliter scale PCR with TaqMan detection." Nucleic Acids Research. 25; 1999-2004, (1997).
Li, Y., et al., Genotyping fetal paternally inherited SNPs by MALDI-TOF MS using cell-free fetal DNA in maternal plasma: Influence of size fractionation. Electrophoresis 27, 3889-3896 (2006).
Lo et al., Lancet 350, 485-487 (1997).
Lo YM et. al., Am J Hum Genet. 62, 768-775. 1998.
Margulies, M. et al. 2005 Nature 437, 376-380.
Nakano et al., "Single-molecule PCR using water-in-oil emulsion;" Journal of Biotechnology 102: 117-124 (2003).
Needham-VanDevanter et al., Nucleic Acids Res. 12:6159-6168, 1984.
Nolte, Adv. Clin. Chem. 33:201-235, 1998.
Oeth, P. et al., "iPLEX™ Assay: Increased Plexing Efficiency and Flexibility for MassARRAY® System through single base primer extension with mass-modified Terminators." SEQUENOM Application Note (2005).
Orita et al., Proc. Natl. Acad. Sci. U.S.A 86: 27776-2770 (1989).
Pearson and Regnier, J. Chrom., 255:137-149, 1983.
Romero and Rotbart in Diagnostic Molecular Biology: Principles and Applications pp. 401-406; Persing et al., eds., Mayo Foundation, Rochester, Minn., 1993.
Sambrook and Russell, Molecular Cloning: A Laboratory Manual 3d ed., 2001.
Sheffield et al., Proc. Natl. Acad. Sci. USA 49: 699-706 (1991).
Singer et al., Biotechniques 4:230, 1986.
Soni and Meller, Clinical Chemistry 53(11): 1996-2001 (2007).
Van der Schoot, C.E., et al., Real-time PCR of bi-allelic insertion/deletion polymorphisms can serve as a reliable positive control for cell-free fetal DNA in non-invasive prenatal genotyping [abstract] Blood 102, 93a (2003).
Venter et al., Science 291: 1304-1351 (2001).
Vogelstein and Kinzler (Digital PCR. Proc Natl Acad Sci U S A. 96; 9236-41, (1999).
White et al., Genomics 12: 301-306 (1992).
Wilkinson, In situ Hybridization, Wilkinson ed., IRL Press, Oxford University Press, Oxford.

(56) References Cited

OTHER PUBLICATIONS

International Preliminary Report on Patentability, mailed on Sep. 23, 2010 in International application No. PCT/US2009/036683 filed on: Mar. 10, 2009 and published as WO 09/114543 on Sep. 17, 2009.
International Search Report and Written Opinion, mailed on Feb. 24, 2010 in International application No. PCT/US2009/036683 filed on: Mar. 10, 2009 and published as WO 09/114543 on Sep. 17, 2009.
Randen et al., "Prenatal genotyping of RHD and SRY using maternal blood," VOX Sanguinis, vol. 85, No. 4, Nov. 2003, pp. 300-306.
Supplementary European Search Report dated: Jul. 14, 2011 for European Application No. EP 09720284 filed: Mar. 10, 2009 based on internation application No. PCT/US2009/036683.
Tungwiwat et al., "Non-invasive fetal sex determination using a conventional nested PCR analysis of fetal DNA in maternal plasma," Clinica Chimica Acta, vol. 334, No. 1-2, Aug. 2003, pp. 173-177.
Adinolfi et al., "Rapid detection of aneuploidies by microsatellite and the quantitative fluorescent polymerase chain reaction." Prenat Diagn. Dec. 1997;17(13):1299-311.
Agresti, Categorical Data Analysis, 2nd Ed. 2002. Wiley.
Altschul et al., "Basic local alignment search tool." J Mol Biol. Oct. 5, 1990;215(3):403-10.
Altschul et al., "Gapped Blast and PSI-Blast: a new generation of protein database search programs." Nucleic Acids Res. Sep. 1, 1997;25(17):3389-402.
Amicucci et al., Clin. Chem. 46:301-302, 2000.
Amir et al., Nature Genet. 23:185-88 (1999).
Anders et al., Clin Chem, Oct. 2010, 56(10):1627-1635, Epub Aug. 20, 2010.
Anderson, S., "Shotgun DNA sequencing using cloned Dnase I-generated fragments," Nucl. Acids Res. 9:3015-3027 (1981.
Antonarakis et al., Am J Hum Genet. Mar. 1992;50(3):544-50.
Antonarakis et al., Nat Genet. Feb. 1993;3(2):146-50.
Aoki E. et al., "Methylation status of the p15INK4B gene in hematopoietic progenitors and peripheral blood cells in myelodysplastic syndromes", Leukemia 14(4):586-593 (2000.
Armour et al., "Measurement of locus copy number by hybridisation with amplifiable probes." Nucleic Acids Res. Jan. 15, 2000;28(2):605-9.
Armour et al., "The detection of large deletions or duplications in genomic DNA." Hum Mutat. Nov. 2002;20(5):325-37.
Asimakopoulos FA et al., "ABL 1 methylation is a distinct molecular event associated with clonal evolution of chronic myeloid leukemia" Blood 94(7):2452-2460 (1999.
Aston et al. (1999) Methods Enzymol. 303:55-73.
Aston et al. (1999) Trends Biotechnol. 17(7):297-302.
Ausubel et al., Current Protocols in Molecular Biology (Ausubel et al., eds., 1994).
Banerji et al., "A lymphocyte-specific cellular enhancer is located downstream of the joining region in immunoglobulin heavy chain genes." Cell. Jul. 1983;33(3):729-40.
Bartel et al., Biotechniques 14: 920-924 (1993.
Batey et al. (1992) Nucl. Acids Res. 20, 4515-4523.
Batey et al. (1996) Nucl. Acids Res. 24, 4836-4837.
Batzer et al., Nucleic Acid Res. 19:5081 (1991).
Beckman Coulter, Introduction to Capillary Electrophoresis, Beckman Coulter 1991.
Benson G. Tandem repeats finder: a program to analyze DNA sequences. Nucleic Acids Res. Jan. 15, 1999;27(2):573-80).
Bianchi, 'Fetal cells in the mother: from genetic diagnosis to diseases associated with fetal cell microchimerism', In: European Journal of Obstetrics & Gynecology and Reproductive Biology, Sep. 2000, vol. 92(I), pp. 103-108.
Boguski et al., "Identification of a cytidine-specific ribonuclease from chicken liver." J Biol Chem. Mar. 10, 1980;255(5):2160-3.
Boyer, L.A. et al. Polycomb complexes repress developmental regulators in murine embryonic stem cells. Nature 441, 349-53 (2006).
Brizot et al., "Maternal serum hCG and fetal nuchal translucency thickness for the prediction of fetal trisomies in the first trimester of pregnancy." Br J Obstet Gynaecol. Feb. 1995;102(2):127-32.

Bullinger et al., "Use of gene-expression profiling to identify prognostic subclasses in adult acute myeloid leukemia." N Engl J Med. Apr. 15, 2004;350(16):1605-16.
Burlingame et al. Anal. Chem. 70:647R-716R (1998).
Burnier et al., "Cell-derived microparticles in haemostasis and vascular medicine," Thromb Haemost 2009, 101:439-451.
Byrne et al., "Multiplex gene regulation: a two-tiered approach to transgene regulation in transgenic mice." Proc Natl Acad Sci U S A. Jul. 1989;86(14):5473-7.
Calame et al., "Transcriptional controlling elements in the immunoglobulin and T cell receptor loci." Adv Immunol. 1988;43:235-75.
Caliper LifeSciences, Products and Contract Services, LabChip GX 2010, printed from the internet on Mar. 15, 2011 (http://www.caliperl.com/products/labchip-gx.htm).
Camper et al., "Postnatal repression of the alpha-fetoprotein gene is enhancer independent." Genes Dev. Apr. 1989;3(4):537-46.
Chan et al. (2004) Clin. Chem. 50:88-92.
Chan et al., Oncogene 22:924-934 (2003).
Chang et al., "LIBSVM: a library for Support Vector Machines," 2001.
Cheson et al, "Report of the National Cancer Institute-sponsored workshop on definitions of diagnosis and response in acute myeloid leukemia" J Clin Oncol 8:813-819, 1990.
Chitty, L. Br Med Bull 54:839-856 (1998).
Chiu et al., "Effects of blood-processing protocols on fetal and total DNA quantification in maternal plasma." Clin Chem. Sep. 2001;47(9):1607-1613.
Chiu et al., Lancet 360:998-1000, 2002.
Chu et al, "A novel approach toward the challenge of accurately quantifying fetal DNA in maternal plasma," Prenatal Diagnosis, 2010; 30:1226-1229.
Colella et al. Biotechniques. Jul. 2003;35(1):146-50.
Costa et al., N. Engl. J. Med. 346:1502, 2002).
Costello et al., Restriction Landmark Genomic Scanning (RLGS): Analysis of CpG Islands in genomes by 2D Gel Electrophoresis, Methods in Molecular Biology, DNA Methylation, 2 Methods and Protocols, v.: 507, 2nd eds., pp. 131-148 (2000).
Cruikshank et al., "A lipidated anti-Tat antibody enters living cells and blocks HIV-1 viral replication." J. Acquired Immune Deficiency Syndromes and Human Retrovirology Mar. 1, 1997;14(3):193-203.
D'Alton., "Prenatal diagnostic procedures." Semin Perinatol. Jun. 1994;18(3):140-62.
Das, R. et al. Proc Natl Acad Sci U S A 103, 10713-6 (2006).
Davison., "Sedimentation of deoxyribonucleic acid isolated under low hydrodynamic shear." Nature. Mar. 26, 1960;185:918-20.
Davison., "The Effect of Hydrodynamic Shear on the Deoxyribonucleic Acid From T(2) and T(4) Bacteriophages." Proc Natl Acad Sci U S A. Nov. 1959;45(11):1560-8.
Dayie et al. (1998) J. Mag. Reson. 130, 97-101 (1998).
Deininger, P. L. "Random subcloning of sonicated DNA: application to shotgun DNA sequence analysis," Anal. Biochem. 129(1):216-223 (1983).
Dembo et al., 1994, Ann. Prob. 22: 2022-2039.
Ding C, Cantor CR (2003) A high-throughput gene expression analysis technique using competitive PCR and matrix-assisted laser desorption ionization time-of-flight MS. Proc Natl Acad Sci U S A 100:3059-3064.
Donis-Keller et al., Nucl. Acids Res. 4:2527-2537 (1977).
Donis-Keller., "Phy M: an RNase activity specific for U and A residues useful in RNA sequence analysis." Nucleic Acids Res. Jul. 25, 1980;8(14):3133-42.
Dupont JM, Tost J, Jammes H, and Gut IG. Anal Biochem, Oct. 2004; 333(1): 119-27.
Eads et al., Cancer Res. 59:2302-2306, 1999.
Eckhardt, F. et al. Nat Genet 38, 1378-85 (2006).
Edlund et al., "Cell-specific expression of the rat insulin gene: evidence for role of two distinct 5' flanking elements." Science. Nov. 22, 1985;230(4728):912-6.
Ehrich et al., "Noninvasive detection of fetal trisomy 21 by sequencing of DNA in maternal blood: a study in a clinical setting," Reports of Major Impact, American Journal of Obstetrics and Gyenocology, Mar. 2011, 205e1-205e11.

(56) References Cited

OTHER PUBLICATIONS

Ehrich et al., A new method for accurate assessment of DNA quality after bisulfite treatment, Nucl. Acids Res. (2007) 35(5): e29 1-8.
Ehrich M, et al. (2005) Quantitative high-throughput analysis of DNA methylation patterns by base specific cleavage and mass spectrometry. Proc Natl Acad Sci U S A 102:15785-15790.
Ehrich M, et al. (2008) Cytosine methylation profiling of cancer cell lines. Proc Natl Acad Sci U S A 105:4844-48.
Eiben et al., "First-trimester screening: an overview." J Histochem Cytochem. Mar. 2005;53(3):281-3.
Ernani et al., Agilent's SureSelect Target Enrichment System: Bringing Cost and Process Efficiency to Next-Generation Sequencing Product Note, Agilent Technologies, Mar. 16, 2009.
Eva and Aaronson, Nature, 316:273-275, 1985.
Extended European Search Report dated Jan. 4, 2012 in European Application No: EP10817598.5 filed: Mar. 18, 2010.
Extended European Search Report dated: Apr. 19, 2012 in European Application No. EP 09815148 filed: Sep. 16, 2009.
Fajkusova L. et al., "Detailed Mapping of Methylcytosine Positions at the CpG Island Surrounding the Pa Promoter at the bcr-abl Locus in CML Patients and in Two Cell Lines, K562 and BV173" Blood Cells Mol. Dis. 26(3):193-204 (2000).
Fan et al., "Noninvasive diagnosis of fetal aneuploidy by shotgun sequencing DNA from maternal blood." Proc Natl Acad Sci U S A. Oct. 21, 2008;105(42):16266-71. Epub Oct. 6, 2008.
Fan et al., "Working Set Selection Using the Second Order Information for Training SVM" Journal of Machine Learning Research 6 (2005) 1889-1918.
Feinberg., "Methylation meets genomics." Nat Genet. Jan. 2001;27(1):9-10.
Ferguson-Smith, "Placental mRNA in maternal plasma: Prospects for fetal screening", PNAS vol. 100, No. 8, 4360-4362 Apr. 15, 2003.
Frommer et al. (Proc. Natl. Acad. Sci. USA 89:1827-1831, 1992.
Futreal, P.A. et al. Nat Rev Cancer 4, 177-83 (2004).
Gardiner-Garden et al., "CpG islands in vertebrate genomes." J Mol Biol. Jul. 20, 1987;196(2):261-82.
Gebhard C, Schwarzfischer L, Pham TH, Andreesen R, Mackensen A, Rehli M (2006) Rapid and sensitive detection of CpG-methylation using methyl-binding (MB)-PCR. Nucleic Acids Res 34:e82.
Gebhard C, Schwarzfischer L, Pham TH, Schilling E, Klug M, Andreesen R, Rehli M (2006) Genomewide profiling of CpG methylation identifies novel targets of aberrant hypermethylation in myeloid leukemia. Cancer Res 66:6118-6128).
Giles et al., "Acute myeloid leukemia." Hematology Am Soc Hematol Educ Program. 2002:73-110.
Go et al. Clin Chem. Dec. 2007;53(12):2223-4.
Goeddel, Gene Expression Technology: Methods in Enzymology 185, Academic Press, San Diego, CA (1990).
Gonzalgo & Jones, Nucleic Acids Res. 25:2529-2531, 1997.
Gottesman, S., Gene Expression Technology: Methods in Enzymology, Academic Press, San Diego, California 185: 119-129 (1990).
Grunau et al., "Bisulfite genomic sequencing: systematic investigation of critical experimental parameters." Nucleic Acids Res. Jul. 1, 2001;29(13):E65-5.
Gupta et al., "Use of specific endonuclease cleavage in RNA sequencing." Nucleic Acids Res. Jun. 1977;4(6):1957-78.
Haddow, et al.,"Screening of maternal serum for fetal Down's syndrome in the first trimester", In: The New England Journal of Medicine, Apr. 2, 1998, Vol.338(14), pp. 955-961.
Hage & Tweed, J. Chromatogr. B Biomed. Sci. Appl. Oct. 10; 699 (1-2): 499-525 (1997.
Hahn et al., (2011) Placenta 32 Suppl: S17-S20.
Hahner et al., "Matrix-assisted laser desorption/ionization mass spectrometry (MALDI) of endonuclease digests of RNA." Nucleic Acids Res. May 15, 1997;25(10):1957-64.
Hannish, J. and M. McClelland, "Activity of DNA modification and restriction enzymes in KGB, a potassium glutamate buffer," Gene Anal. Tech 5:105 (1988.
Hart et al., J.Biol.Chem., 269:62-65, 1994.
Hasan et al., Nucl. Acids Res. 24:2150-2157 (1996.

Heegaard, J Mol. Recognit. Winter; 11(1-6): 141-8 (1998).
Hennig et al (2007) J. Am. Chem. Soc. 129, 14911-14921.
Herman et al. Proc. Nat. Acad. Sci. USA 93:9821-9826, 1996.
Hershey, A. D. and Burgi, E. J. Mol. Biol, 2:143-152 (1960.
HiSeq 2000 Sequencing System Specification Sheet, Illumina Inc. 2010.
Homer, J. et al., Prenat Diagn 23:566-571 (2003).
Hook, E. B. Lancet 2:169-172 (1981).
Hromandnikova, et al., "Quantification of Fetal and Total Circulatory DNA in Maternal Plasma Samples Before and After Size Fractionation by Agarose Gel Electrophoresis,"DNA and Cell Biology, vol. 25, No. 11, 2006, pp. 635-640.
Hu, D. G. et al., "Aneuploidy detection in single cells using DNA array-based comparative genomic hybridization", Mol Hum Reprod 10: 283-289, (2004).
Huang et al., "Mechanism of ribose 2'-group discrimination by an RNA polymerase." Biochemistry. Jul. 8, 1997;36(27):8231-42.
Hulten et al., "Rapid and simple prenatal diagnosis of common chromosome disorders: advantages and disadvantages of the molecular methods FISH and QF-PCR." Reproduction. Sep. 2003;126(3):279-97.
Hunkapiller et al., "A microchemical facility for the analysis and synthesis of genes and proteins." Nature. Jul. 12-18, 1984;310(5973)105-11.
Hyrup et al., "Peptide nucleic acids (PNA): synthesis, properties and potential applications." Bioorg Med Chem. Jan. 1996;4(1):5-23.
Imai et al. , 1992, J. Virol. Methods 36: 181-184).
Imamura et al., "Prenatal diagnosis of adrenoleukodystrophy by means of mutation analysis." Prenat Diagn. Mar. 1996;16(3):259-61.
Innis et al., PCR Protocols: A Guide to Methods and Applications, Innis et al., eds, 1990.
Issa., "CpG island methylator phenotype in cancer." Nat Rev Cancer. Dec. 2004;4(12):988-93.
Iverson et al., 1981, Prenat. Diagn. 9: 31-48.
Iwabuchi et al., Oncogene 8: 1693-1696 (1993.
Jing et al. (1998) Proc Natl Acad Sci USA. 95(14):8046-51.
Johansen et al., "An investigation of methods for enriching trophoblast from maternal blood." Prenat Diagn. Oct. 1995;15(10):921-31.
Kaneko et al., Gut 52:641-646 (2003).
Karlin et al., "Methods for assessing the statistical significance of molecular sequence features by using general scoring schemes." Proc Natl Acad Sci U S A. Mar. 1990;87(6):2264-8.
Kent, "BLAT—the BLAST-like alignment tool." Genome Res. Apr. 2002;12(4):656-64.
Kessel et al., "Murine developmental control genes." Science. Jul. 27, 1990;249(4967):374-9.
Kidd JM et al. Mapping and sequencing of structural variation from eight human genomes. Nature. May 1, 2008;453 (7191):56-64).
Kriegler, Gene Transfer and Expression: A Laboratory Manual (1990).
Kristensen et al., "PCR-Based Methods for Detecting Single-Locus DNA Methylation Biomarkers in Cancer Diagnostics, Prognostics, and Response to Treatement", Clinical Chemistry, Washington DC, vol. 55, No. 8., Aug. 1, 2009, pp. 1471-1483.
Kuchino et al., "Enzymatic RNA sequencing." Methods Enzymol. 1989;180:154-63.
Kuhn et al., "DNA Helicases" Cold Spring Harb Symp Quant Biol. 1979;43 Pt 1:63-7.
Kulkarmi et al., "Global DNA methylation patterns in placenta and its association with maternal hypertension in pre-eclampsia," (2011) DNA Cell Biol. 30(2):79-84.
Kumps et al., "RMeseuarlcthi aprtilcelex Amplicon Quantification (MAQ), a fast and efficient method for the simultaneous detection of copy number alterations in neuroblastoma," BMC Genomics 2010, 11:298, pp. 1-10.
Lai et al. (1999) Nat Genet. 23(3):309-13.
Laird, P.W. Nature Reviews Cancer 3, 253-266 (2003).
Larkin et al., "Clustal W and Clustal X version 2.0." Bioinformatics. Nov. 1, 2007;23(21):2947-8. Epub Sep. 10, 2007.
Lee et al., Fetal Nucleic Acids in Maternal Plasma, In:Fetal and Maternal Medicine Review, 2006, vol. 17,(2), pp. 125-137.

(56) References Cited

OTHER PUBLICATIONS

Lee TI, et al. (2006) Control of developmental regulators by Polycomb in human embryonic stem cells. Cell 125:301-313).

Leung et al., "An efficient algorithm for identifying matches with errors in multiple long molecular sequences." J Mol Biol. Oct. 20, 1991;221(4):1367-78.

Li et al. Nucl. Acids Res. 23:4495-4501 (1995).

Li et al., "Size separation of circulatory DNA in maternal plasma permits ready detection of fetal DNA polymorphisms." Clin Chem. Jun. 2004;50(6):1002-11. Epub Apr. 8, 2004

Li et al., "Targeted mutation of the DNA methyltransferase gene results in embryonic lethality." Cell. Jun. 12, 1992;69(6):915-26.

Lingbeek, M.E., Bruggeman, S.W. & van Lohuizen, M. Cell 118, 409-18 (2004).

Little, et al. Nat Med 3:1413-6 (1997.

Litz C. E. et al., "Methylation status of the major breakpoint cluster region in Philadelphia chromosome negative leukemias" Leukemia 6(1):35-41 (1992.

Liu et al., "Quantification of regional DNA methylation by liquid chromatography/tandem mass spectrometry", Analytical Biochemistry, Academic Press Inc, New York, vol. 391, No. 2, Aug. 15, 2009, pp. 106-113.

Liu et al., "The ribosomal small-subunit protein S28 gene from *Helianthus annuus* (asteraceae) is down-regulated in response to drought, high salinity, and abscisic acid," American Journal of Botany, vol. 90, No. 4., Apr. 1, 2003, pp. 526-531.

Lo et al. (Nat Med. Feb. 2007;13(2):218-23).

Lo et al., "Maternal Plasma DNA Sequencing Reveals the Genome-Wide Genetic and Mutational Profile of the Fetus," Prenatal Diagnosis, Science Translational Medicine, Dec. 8, 2010, vol. 2, Issue 61, 1-13 Lo et al. (2010).

Lo et al., Clin. Chem. 45:1747-1751, 1999.

Lo et al., Clin. Chem. 45:184-188, 1999.

Lo et al., N. Engl. J. Med. 339:1734-1738, 1998).

Lo, "Recent advances in fetal nucleic acids in maternal plasma." J Histochem Cytochem. Mar. 2005;53(3):293-6.

Lun et al., "Microfluidics digital PCR reveals a higher than expected fraction of fetal DNA in maternal plasma." Clin Chem. Oct. 2008;54(10):1664-72. Epub Aug. 14, 2008.

Lun et al., "Noninvasive prenatal diagnosis of monogenic diseases by digital size selection and relative mutation dosage on DNA in maternal plasma," PNAS, vol. 105, No. 50, Dec. 16, 2008, pp. 19920-19925.

Madura et al., J. Biol. Chem. 268: 12046-12054 (1993).

Majlessi et al., Nucleic Acids Research, 26(9):2224-2229, (1998).

Malik et al., "Polyethylene glycol (PEG)-modified granulocyte-macrophage colony-stimulating factor (GM-CSF) with conserved biological activity." Exp Hematol. Sep. 1992;20(8):1028-35.

Mann et al., "Development and implementation of a new rapid aneuploidy diagnostic service within the UK National Health Service and implications for the future of prenatal diagnosis." Lancet. Sep. 29, 2001;358(9287)1057-61.

Mann, K. Methods Mol Med 92:141-156 (2004).

Mao and Williamson (1999) Nucl. Acids Res. 27, 4059-4070.

Marais et al., EMBO J. 14: 3136-3145 (1995).

Marais et al., J. Biol. Chem. 272: 4378-4383 (1997.

Mason et al., EMBO J. 18: 2137-2148 (1999.

McClelland, M. et al., "A single buffer for all restriction endonucleases," Nucl. Acids Res. 16:364 (1988).

McConnell, H. M. et al., Science 257: 1906-1912 (1992)).

Meller A. 2007 Clin Chem 53: 1996-2001.

Metzker M Nature Rev 11:31-46 (2010).

Meyers & Miller, CABIOS 4:11-17 (1989).

Mito, Y., Henikoff, J.G. & Henikoff, S. Nat Genet 37, 1090-7 (2005.

Molecular Cloning of PCR Products, Unit 15.4, Current Protocols in Molecular Biology, (2001 John Wiley & Sons, Inc.) 15.4.1-15.4.11, Supplement 56.

Moudrianakis E. N. and Beer M. Proc Natl Acad Sci USA. Mar. 1965; 53:564-71.

Mouliere et al., "High Fragmentation Characterizes Tumour-Derived Circulating DNA," PLoS ONE, Sep. 2011, vol. 6, Issue 9, e23438, 1-10.

Nakamaye et al., Nucl. Acids Res. 23:9947-9959(1988).

Needleman et al., "A general method applicable to the search for similarities in the amino acid sequence of two proteins." J Mol Biol. Mar. 1970;48(3)444-453.

Ng et al. , 2003, Proc. Natl. Acad. Sci. USA 100 : 4748-4753.

Ng et al., 2002, Clin. Chem. 48: 1212-1217.

Nicolaides et al., "One-stop clinic for assessment of risk of chromosomal defects at 12 weeks of gestation." J Matern Fetal Neonatal Med. Jul. 2002;12(1):9-18.

Nicolaides, K. H. et al., Prenat Diagn 22:308-315 (2002)).

Nicolaidis et al., "Origin and mechanisms of non-disjunction in human autosomal trisomies." Hum Reprod. Feb. 1998;13(2):313-9.

Nishizuka et al., "Proteomic profiling of the NCI-60 cancer cell lines using new high-density reverse-phase lysate microarrays." Proc Natl Acad Sci U S A. Nov. 25, 2003;100(24):14229-34. Epub Nov. 17, 2003.

Nosaka, K. et al., "Increasing methylation of the CDKN2A gene is associated with the progression of adult T-cell leukemia", Cancer Res. 60(4):1043-1048 (2000).

Nygren et al., "Quantification of Fetal DNA by Use of Methylation-Based DNA Discrimination," Clinical Chemistry, 56:10, pp. 1627-1635.

Oefner, P. J. et al., "Efficient random subcloning of DNA sheared in a recirculating point-sink flow system," Nucl. Acids Res. 24(20):3879-3886 (1996).

Oeth et al., "Qualitative and quantitative genotyping using single base primer extension coupled with matrix-assisted laser desorption/ionization time-of-flight mass spectrometry (MassARRAY)." Methods Mol Biol. 2009;578:307-43.

Ohm, J.E. et al. A stem cell-like chromatin pattern may predispose tumor suppressor genes to DNA hypermethylation and heritable silencing. Nat Genet 39, 237-42 (2007).

Ohtsuka et al., J. Biol. Chem. 260:2605-2608 (1985).

Okano et al., "DNA methyltransferases Dnmt3a and Dnmt3b are essential for de novo methylation and mammalian development." Cell. Oct. 29, 1999;99(3):247-57.

Old RW, "Candidate epigenetic biomarkers for non-invasive prenatal diagnosis of Down syndrom," Reprod Biomed. Online 2007, vol. 15, No. 2, pp. 227-235.

Olek et al., "A modified and improved method for bisulphite based cytosine methylation analysis." Nucleic Acids Res. Dec. 15, 1996;24(24):5064-6.

Oligonucleotides and Analogues, A Practical Approach, F. Eckstein, editor, IRL Press, Oxford, 1991.

Osborne, et al., Curr. Opin. Chem. Biol.1(1): 5-9 (1997.

Oudejans et al., 2003, Prenatal Diagnosis 23: 111-116.

Padilla et al., "Efficient synthesis of nucleic acids heavily modified with non-canonical ribose 2'-groups using a mutantT7 RNA polymerase (RNAP)." Nucleic Acids Res. Mar. 15, 1999;27(6)1561-3.

Palomaki et al., "Maternal serum screening for Down syndrome in the United States: a 1995 survey." Am J Obstet Gynecol. May 1997;176(5):1046-51.

Pandya et al., "Screening for fetal trisomies by maternal age and fetal nuchal translucency thickness at 10 to 14 weeks of gestation." Br J Obstet Gynaecol. Dec. 1995;102(12):957-62.

Patel, D. J., Curr. Opin. Chem. Biol. Jun;1(1): 32-46 (1997).

Paulin, R. et al. in Nucleic Acids Res. 26:5009-5010, 1998.

Pearson, 1988, Proc. Natl. Acad. Sci. USA 85(5): 2444-2448.

Perry-O'Keefe et al., "Peptide nucleic acid pre-gel hybridization: an alternative to southern hybridization." Proc Natl Acad Sci U S A. Dec. 10, 1996;93(25):14670-5.

Pertl et al., "Rapid molecular method for prenatal detection of Down's syndrome." Lancet. May 14, 1994;343(8907):1197-8.

Peters et al., "Noninvasive Prenatal Diagnosis of a Fetal Microdeletion Syndrome," New England Journal of Medicine, Nov. 10, 2011, pp. 1847-1848.

Petersen and Mikkelsen. Cytogenet Cell Genet. 2000;91(1-4):199-203.

Pinkert et al., Genes Dev. 1: 268-277 (1987).

(56) References Cited

OTHER PUBLICATIONS

Poon et al., 2000, Clin. Chem. 46: 1832-1834.
Poon et al., "Differential DNA methylation between fetus and mother as a strategy for detecting fetal DNA in maternal plasma." Clin Chem. Jan. 2002;48(1):35-41.
Porter et al., Biochemistry 34: 11963-11969 (1995).
Qu et al., "Analysis of drug-DNA binding data." Methods Enzymol. 2000;321:353-69.
Queen et al., "Immunoglobulin gene transcription is activated by downstream sequence elements." Cell. Jul. 1983;33(3):741-8.
Radding., "Homologous pairing and strand exchange in genetic recombination." Annu Rev Genet. 1982;16:405-37.
Rashtchian (1994, PCR Methods Applic. 4: S83-S91).
Rivas, G., and Minton, A. P., Trends Biochem Sci Aug;18(8): 284-7 (1993).
Robertson et al., Nature Rev. Genet. 1:11-19 (2000).
Robinson M. D. and T. P. Speed. "A comparison of Affymetrix gene expression arrays." BMC Bioinformatics 8:449 (2007).
Rojo et al., "Cusativin, a new cytidine-specific ribonuclease accumulated in seeds of *Cucumis sativus* L." Planta. 1994;194(3):328-38.
Rollins et al., "Large-scale structure of genomic methylation patterns." Genome Res. Feb. 2006;16(2):157-63. Epub Dec. 19, 2005.
Roschke et al., "Karyotypic complexity of the NCI-60 drug-screening panel." Cancer Res. Dec. 15, 2003;63(24):8634-47.
Rosenberg, H. S. and Bendich, A. J. Am. Chem. Soc. 82:3198-3201 (1960).
Rossolini et al., Mol. Cell. Probes 8:91-98 (1994).
Sadri & Hornsby (Nucl. Acids Res. 24:5058-5059, 1996.
Saito et al., Lancet 356:1170, 2000.
Sanchez et al, "Effects of Sulpiride on Prolactin and mRNA Levels of Steroid 5a-reductase Isozymes in Adult Rat Brain," Neurochem Res (2008) 33:820-825.
Santoro, S. W. and Joyce, G. F. "A general purpose RNA-cleaving DNA enzyme," Proc. Natl. Acad. Sci. USA 94:4262-4266 (1997.
Sargent et al., Meth. Enz. 152:432 (1988)).
Schlesinger et al., "Polycomb-mediated methylation on Lys27 of histone H3 pre-marks genes for de novo methylation in cancer." Nat Genet. Feb. 2007;39(2):232-6. Epub Dec. 31, 2006.
Schouten et al., "Relative quantification of 40 nucleic acid sequences by multiplex ligation-dependent probe amplification." Nucleic Acids Res. Jun. 15, 2002;30(12):e57.
Schriefer, L. A. et al., "Low pressure DNA shearing: a method for random DNA sequence analysis," Nucl. Acids Res. 18:7455-7456 (1990.
Schuler GD, Sequence mapping by electronic PCR., Genome Res. May 1997;7(5):541-50.
Scott et al. (2004) J. Am. Chem. Soc. 126, 11776-11777.
Sekizawa et al., Clin. Chem. 47:2164-2165, 2001.
Silverman et al., "Methylation inhibitor therapy in the treatment of myelodysplastic syndrome." Nat Clin Pract Oncol. Dec. 2005;2 Suppl 1:S12-23.
Simoncsits et al., "New rapid gel sequencing method for RNA." Nature. Oct. 27, 1977;269(5631):833-6.
Sjolander & Urbaniczk, Anal. Chem. 63: 2338-2345 (1991.
Slater et al., "Rapid, high throughput prenatal detection of aneuploidy using a novel quantitative method (MLPA)." J Med Genet. Dec. 2003;40(12):907-12.
Smith et al., "Identification of common molecular subsequences." J Mol Biol. Mar. 25, 1981;147(1):195-7.
Smith et al., "Single-step purification of polypeptides expressed in *Escherichia coli* as fusions with glutathione S-transferase." Gene. Jul. 15, 1988;67(1):31-40.
Snijders et al., "Assembly of microarrays for genome-wide measurement of DNA copy number." Nat Genet. Nov. 2001;29(3):263-4.
Snijders et al., "First-trimester ultrasound screening for chromosomal defects." Ultrasound Obstet Gynecol. Mar. 1996;7(3):216-26.
Snijders et al., "UK multicentre project on assessment of risk of trisomy 21 by maternal age and fetal nuchal-translucency thickness at 10-14 weeks of gestation. Fetal Medicine Foundation First Trimester Screening Group." Lancet. Aug. 1, 1998;352(9125):343-6.

Sousa et al., "A mutant T7 RNA polymerase as a DNA polymerase." EMBO J. Sep. 15, 1995;14(18):4609-21.
Spetzler et al, Enriching for Rare Subpopulations of Circulating Microvesicles by the Depletion of Endothelial-and Leukocyte-Derived Microvesicles, CARIS Life Sciences, Carisome Posters, Papers, Abstracts and Presentations, American Academy of Cancer Research (AACR 2011).
Stanssens et al., "High-throughput MALDI-TOF discovery of genomic sequence polymorphisms." Genome Res. Jan. 2004;14(1):126-33.
Staunton et al., "Chemosensitivity prediction by transcriptional profiling." Proc Natl Acad Sci U S A. Sep. 11, 2001;98(19)10787-92.
Strathdee, et al., Am. J. Pathol. 158:1121-1127 (2001).
Strohmeier, Fred, "A New High-Performance Capillary Electrophoresis Instrument," 10-19, Hewlett-Packard Journal, Jun. 1995.
Szabo et al., Curr. Opin. Struct. Biol. 5: 699-705 (1995).
Takai et al., Proc. Natl. Acad. Sci. U.S.A. 99:3740-3745, 2002).
Tang et al. (2002) Analytical Chemistry 74, 226-331.
The Cancer Test, Cell Free DNA, 2007, Health Screen Inc. printed from the internet on Mar. 20, 2011 (http://www.thecancertest.com/science-of-cell-free-dna/.
The Human Genome, T. Strachan, BIOS Scientific Publishers, 1992.
The World Health Organization histological typing of lung tumours, Am J Clin Pathol 1982; 77:123-136.
Thorstenson, Y.R. et al., "An Automated Hydrodynamic Process for Controlled, Unbiased DNA Shearing," Genome Research 8:848-855 (1998).
Tolbert and Williamson (1996) J. Am. Chem. Soc. 118, 7929-7940.
Tolbert and Williamson (1997) J. Am. Chem. Soc. 119, 12100-12108.
Tong et al., "Noninvasive Prenatal Detection of Fetal Trisomy 18 by Epigenetic Allelic Ratio Analysis in Maternal Plasma: Theoretical and Empirical Considerations," Clinical Chemistry 52:12, pp. 2149-2202.
Tooke N and Pettersson M. IVDT. Nov. 2004; 41.
Tost et al., Nucl. Acids Res. 37:e50 (2003).
Toyota et al., "Methylation profiling in acute myeloid leukemia." Blood. May 1, 2001;97(9):2823-9.
Toyota et al., Cancer Res. 59:2307-12, 1999.
Tynan et al., "Fractional DNA quantification by massively parallel shotgun sequencing-implications for fetal fraction measurement in maternal plasma," (Sequenom MME) ASHG Poster, 2011.
Uhlmann, K. et al. Electrophoresis 23:4072-4079 (2002.
Valk et al., "Prognostically useful gene-expression profiles in acute myeloid leukemia." N Engl J Med. Apr. 15, 2004;350(16):1617-28.
Valk-Lingbeek et al., "Stem cells and cancer; the polycomb connection." Cell. Aug. 20, 2004;118(4):409-18.
Veltman et al., "High-throughput analysis of subtelomeric chromosome rearrangements by use of array-based comparative genomic hybridization." Am J Hum Genet. May 2002;70(5):1269-76. Epub Apr. 9, 2002.
Verbeck et al. in the Journal of Biomolecular Techniques (vol. 13, Issue 2, 56-61).
Verma et al., "Rapid and simple prenatal DNA diagnosis of Down's syndrome." Lancet. Jul. 4, 1998;352(9121):9-12.
Vincenet et al., "Helicase-Dependent isothermal DNA Amplification,"EMBO reports 5(8):795-800 (2004).
Vire et al., "The Polycomb group protein EZH2 directly controls DNA methylation." Nature. Feb. 16, 2006;439(7078):871-4. Epub Dec. 14, 2005.
Volkerding et al. Clin Chem 55:641-658 (2009).
Vu et al. "Symmetric and asymmetric DNA methylation in the human IGF2-H19 imprinted region," Genomics, Mar. 1 ;64(2):132-143. (2000).
Wada et al., "Codon usage tabulated from the GenBank genetic sequence data." Nucleic Acids Res. May 11, 1992;20 Suppl:2111-8.
Wald and Hackshaw, Prenat Diagn 17(9):821-829 (1997).
Wang, H. et al. BMC Genomics 7, 166 (2006.
Wapner et al., "First-trimester screening for trisomies 21 and 18." N Engl J Med. Oct. 9, 2003;349(15):1405-13.
Waterman et al., 1980, J. Mol. Biol. 147: 195-197.
Weber et al., Oncogene 19: 169-176 (2000.
Weisenberger, D.J. et al. Nat Genet 38, 787-93 (2006).

(56) References Cited

OTHER PUBLICATIONS

Widschwendter, M. et al. Epigenetic stem cell signature in cancer. Nat Genet 39, 157-8 (2007).
Winoto et al., "A novel, inducible and T cell-specific enhancer located at the 3' end of the T cell receptor alpha locus." EMBO J. Mar. 1989;8(3):729-33.
Xiong & Laird, Nucleic Acids Res. 25:2532-2534, 1997.
Yamada et al. (Genome Research 14:247-266, 2004).
Yan et al., "A novel diagnostic strategy for trisomy 21 using short tandem repeats," Electrophoresis 2006, 27,416-422.
Zahra S, et al, Plasma microparticles are not elevated in fresh plasma from patients with gynaecologicalmalignancy—An observational study, Gynecol Onco, Oct. 2011;123(1):152-156.
Zervos et al., Cell 72:223-232 (1993.
Zhao et al., (2010) Pretat Diag 30(8):778-782.
Zheng et al., "Nonhematopoietically Derived DNA Is Shorter than Hematopoietically Derived DNA in Plasma: A Transplantation Model," Clin Chem 58:2, Nov. 3, 2011.
Zhong et al., Am. J. Obstet. Gynecol. 184:414-419, 2001).
Zhong et al., Prenat. Diagn. 20:795-798, 2000.
Zimmermann Lecturer, et al., 'Serum parameters and nuchal translucency in first trimester screening for fetal chromosomal abnormalities', In: BJOG: An International Journal of Obstetrics & Gynaecology, 1996, vol. I03(1O), pp. 1009-1014.
Zimmermann, B. et al., Clin Chem 48:362-363 (2002).
Zuker "Mfold web server for nucleic acid folding and hybridization prediction," Nucleic Acids Res. 31(13), 3406-3415.
International Preliminary Report on Patentability dated: Sep. 3, 2009 in International Application No. PCT/US2008/54468 filed on Feb. 20, 2008.
International Search Report and Written Opinion dated: Sep. 23, 2008 in International Application No. PCT/US2008/54468 filed on Feb. 20, 2008.
International Preliminary Report on Patentability dated: Feb. 18, 2010 in International Application No. PCT/US2008/54470 filed on Feb. 20, 2008.
International Search Report and Written Opinion dated: Aug. 18, 2008 in International Application No. PCT/US2008/54470 filed on Feb. 20, 2008.
International Preliminary Report on Patentability dated: Dec. 30, 2009 in International Application No. PCT/US2008/066791 filed on Jun. 12, 2008.
International Search Report and Written Opinion dated: Dec. 22, 2008 in International Application No. PCT/US2008/066791 filed on Jun. 12, 2008.
International Preliminary Report on Patentability mailed on: Mar. 31, 2011 in International Application No. PCT/US2009/057215 filed on Sep. 16, 2009 and published as: WO 10/033639 on Mar. 25, 2010.
International Search Report and Written Opinion mailed on: Dec. 29, 2010 in International Application No. PCT/US2009/057215 filed on Sep. 16, 2009 and published as: WO 10/033639 on Mar. 25, 2010.
International Preliminary Report on Patentability dated: Mar. 29, 2012 in International Application No. PCT/US2010/027879 filed on Mar. 18, 2010.
International Search Report and Written Opinion mailed on: Dec. 30, 2010 in International Application No. PCT/US2010/027879 filed on Mar. 18, 2010.
International Preliminary Report on Patentability dated: Jul. 5, 2012 in International Application No. PCT/US2010/061319 filed on Dec. 20, 2010.
International Search Report and Written Opinion dated: Sep. 21, 2011 in International Application No. PCT/US2010/061319 filed on Dec. 20, 2010.
International Search Report and Written Opinion dated: Jan. 10, 2012 in International Application No. PCT/US2012/035479 filed on Apr. 27, 2012.
Office Action dated: Feb. 27, 2013 in U.S. Appl. No. 12/561,241, filed Sep. 16, 2009.
Office Action dated: Jun. 15, 2012 in U.S. Appl. No. 12/561,241, filed Sep. 16, 2009.
Office Action dated: Apr. 5, 2013 in U.S. Appl. No. 13/495,975, filed Jun. 13, 2012.
Office Action dated: Apr. 5, 2013 in U.S. Appl. No. 13/517,532, filed Jun. 13, 2012.
Office Action dated: Jan. 28, 2013 in U.S. Appl. No. 13/457,978, filed Apr. 27, 2012 and published as: 2012/0276542 on: Oct. 1, 2012.
Office Action dated: Sep. 17, 2012 in U.S. Appl. No. 13/457,978, filed Apr. 27, 2012 and published as: 2012/0276542 on: Oct. 1, 2012.
Office Action dated: Feb. 6, 2013 in U.S. Appl. No. 13/458,036, filed Apr. 27, 2012 and published as: 2012/0264618 on: Oct. 18, 2012.
Office Action dated: Sep. 24, 2012 in U.S. Appl. No. 13/458,036, filed Apr. 27, 2012 and published as: 2012/0264618 on: Oct. 18, 2012.
Office Action dated: Feb. 5, 2013 in U.S. Appl. No. 13/458,341, filed Apr. 27, 2012.
Office Action dated: Sep. 17, 2012 in U.S. Appl. No. 13/458,341, filed Apr. 27, 2012.
Li et al., Dynamic Distribution of Linker Histone H1.5 in Cellular Differentiation, PLOS Genetics, vol. 8, Issue 8, e1002879, Aug. 2012, pp. 1-13.
Zhang et al., "Histone H1 Depletion Impairs Embryonic Stem Cell Differentiation," PLOS Genetics, vol. 8, Issue 5, e1002691, May 2012, pp. 1-14.
Terme et al. "Histone H1 Variants Are Differentially Expressed and Incorporated into Chromatin during Differentiation and Reprogramming to Pluripotency," The Journal of Clinical Chemistry, vol. 286, No. 41, Oct. 14, 2011, pp. 35347-35357.
Millipore, QIA25 Nucleosome ELISA Kit, Information Brochure, Calbiochem, Feb. 26, 2013.
Dai et al., "Detection of Post-translational Modifications on Native Intact Nucleosomes by ELISA," Journal of Visualized Experiments, 2011, pp. 1-4.
Cell Death Detection ELISA Plus Cat. No. 11 774 425 001 "Detection of Post-translational Modifications on Native Intact Nucleosomes by ELISA," Version 11.0, Roche, Content Version: Sep. 2010, pp. 1-19.
Salgame et al., "An ELISA for detection of apoptosis," Nucleic Acids Research, 1997, vol. 25, No. 3, pp. 680-681.
Weiss et al., "H1 variant-specific lysine methylation by G9a/KMT1C and Glp1/KMT1D," Epigenetics & Chromatin Mar. 24, 2010, 3:7, pp. 1-13.
International Search Report and Written Opinion mailed on Aug. 14, 2013 in International Application No. PCT/US2013/041354, filed on May 16, 2013.
Office Action dated Sep. 20, 2013 in U.S. Appl. No. 13/517,532, filed Jun. 13, 2012 and published as US 2013-0150249 on Jun. 13, 2013.
Office Action dated Sep. 24, 2013 in U.S. Appl. No. 13/495,975, filed Jun. 13, 2012 and published as US 2012-0277119 on Nov. 1, 2012.
Sayres et al., "Cell-free fetal nucleic acid testing: A review of the technology and its applications" Obstetrical and Gynecological Survey (2011) 66(7):431-442.
Sharma et al., "Mass spectrometric based analysis, characterization and applications of circulating cell free DNA isolated from human body fluids" International Journal of Mass Spectrometry (2011) 304:172-183.
NCBI dbSNP cluster report record for rs16139, accessed Sep. 16, 2013.
International Search Report and Written Opinion mailed on Jul. 1, 2013 in International Application No. PCT/US2013/028699, filed on Mar. 1, 2013.
Go et al., "Non-invasive aneuploidy detection using free fetal DNA and RNA in maternal plasma: recent progress and future possibilities" Human Reproduction Update (2011) 17(3):372-382.
Beaudet, "Progress toward noninvasive prenatal diagnosis" Clin. Chem. (2011) 57(6):802-804.
Office Action dated Aug. 13, 2013 in U.S. Appl. No. 13/517,508, filed Jun. 13, 2012 and published as US 2013-0143211 on Jun. 6, 2013.
Chan et al., "Hypermethylated RASSFIA in Maternal Plasma: A Universal Fetal DNA Marker that Improves the Reliability of Noninvasive Prenatal Diagnosis" Clin. Chem. (2006) 52:2211-2218.
International Search Report and Written Opinion mailed on Jul. 16, 2013 in International Application No. PCT/US2013/041906, filed on May 20, 2013.

(56) References Cited

OTHER PUBLICATIONS

Tabor et al., "Non-Invasive Fetal Genome Sequencing: Opportunities and Challenges" American Journal of Medical genetics Part A (2012) 158A(10):2382-2384.

Kitzman et al., "Noninvasive Whole-Genome Sequencing of a Human Fetus" Science Translation Medicine (2012) 4(137-140):115-122.

Office Action dated: Apr. 12, 2013 in U.S. Appl. No. 12/727,198, filed Mar. 18, 2010.

Extended European Search Report dated Apr. 22, 2013 in European Application No. EP10843520 filed: Dec. 20, 2010 based on International Application No. PCT/US2010/061319.

* cited by examiner

FIGURE 1A

CDY1-1

```
TATGGAGTACTTCAGGGTAGAATGGACAGATACTCAAAAGCAGTATGAACAAACAAAGATTAAGGTAAAGATAAATACATGAACAA
ATATGTAAGATAAAAAATTTGGCTGGGCTCAGTGGCTCACACCTGTAATCCCAGCATTTTGGGAGGCTGAGGTGCTTGGATCACGA
GGTCAGGAGATCGAGACAATCCTGGCTAACATGGTGAAACCCCGTCTCTAC[T/*]AAAAATACAACAAATTCGTAGGGCCAGGTG
GCAGGTGCCTGTAGTCTCAGCTACTCGGGAGGCTGAGACAGGAGAAT

Amplicon length:  98 bp

Forward Primer:   ACGTTGGATGGTCAGGAGATCGAGACAATC

Reverse Primer:   ACGTTGGATGCTGGCCCTACGAATTTGTTG

Extend Primer:    GGCCCTACGAATTTGTTGTATTTTT

Extend Direction:   R

Extend Allele:    T
```

FIGURE 1B

HSFY-1

```
CCTTTGCCTTTGTGTCCACAGAGGTTTCTGTATTCCACCGTGCAGGTGCAAAACATACACCAGAGCAGAAAAGCAGTTTGTTCTTC
CTCTTTGTTTCTAAATATAGAGGTGCTTAAACAACATCCCTATTTTGAGATTACTATTCCATAAAAGAAAACAATCTCATCTTAGA
GTAACTTTCACTTCTTGTTCTAGCAAAGAGAAAGTTGCCTTTCTGCCTGCAGAAATTATCAAACGCCTCTTTTGTATTTTAATTTC
ATGAGA[A/*]GGATTGAGAAGAGATGGGGGGTGGAGAGAGAGGAAA

Amplicon length:  119 bp

Forward Primer:   ACGTTGGATGAAAGTTGCCTTTCTGCCTGC

Reverse Primer:   ACGTTGGATGTTTCCTCTCTCTCCACCCC

Extend Primer:    CCCATCTCTTCTCAATCC

Extend Direction:   R

Extend Allele:    A
```

FIGURE 1C

```
RBMY1A1-1

GGCCAGGCGAACCTCAGGCTCTTTGTCCTACTAAAAAGCGCAGGTATTTTCTG[T/*]TTCTCTGGACAGCTGGGTCTCTCGGCAA
GAATAGAAAGCGAAGGTTTGGGATTTTGTCTATAAAAGGGGATGGGTTTTCTATGTGTGGGTGTTGAATTACGGGAGGAGTCAGTG
GGGAAAGAACTCCTCAGTGCTATTAAGAGACTCACTTTCGTTAAACTCATTGATTTTTCCTGAGGATTCTACCTTTAACTGCCTAA
TGTGTCCGACTAGTTGTGGGAGATGGTGCTAAGCCGCCATTGGTTTT

Amplicon length:  101

Forward Primer:   ACGTTGGATGGAACCTCAGGCTCTTTGTCC

Reverse Primer:   ACGTTGGATGTCTATTCTTGCCGAGAGACC

Extend Primer:    AAAAAGCGCAGGTATTTTCTG

Extend Direction: F

Extend Allele:    T
```

FIGURE 1D

```
RBMY2-1

CAATGCAGAAATAACATTTCAATTTTTGATTTGCAAACAAGGATTGGTATGCAATAACTATTATTTTCAATGCTTGCTTTAATATC
TGCTCGAGTCTCCTTTTTCAGATCGACTCTCCCCACCATCTACTATAGATGCCACATAACTTGAGCTACCATATGCTTCACGAGGA
TCAGGGAGCACCCTACCCAGAGAAGGCGGATTCCTTTGGTCTTTTCTGCAAACATGCTCACGATCAC[A/*]ATAATGAAAATCAC
CACAGCTCGAGTAACTCTCCCAACTTCTGCCATATCTATCTCGTGTA

Amplicon length:  111

Forward Primer:   ACGTTGGATGAGAGAAGGCGGATTCCTTTG

Reverse Primer:   ACGTTGGATGGAAGTTGGGAGAGTTACTCG

Extend Primer:    AAACATGCTCACGATCAC

Extend Direction: F

Extend Allele:    A
```

FIGURE 1E

```
TTTY16-1

GCCACTCTTCTAGAAAGAACAGAAGAACACCACAACCAAGAACAGAAATATACCAGTGTTTAATTGTCTTTCAGCCAATCCAAGGA
GAGACACTATCATTCATCTCTACCGGGCCTATTAAATTTACCTCGAATTTGATTCCCAGAGGAGTTGGTGCTTCACATCATCAGGG
GGAACTT[C/*]TCCATTGTCTTGGGATTTCAGTCTGGGATAGAGACTTTGAACAGCAATAAGGTAATAAGGTCAGATAGGGGTGG
GGATACCCCTCTGGTGAGGGGTGGATGCCATGCTGTACCTTCACCTG

Amplicon length: 100

Forward Primer:   ACGTTGGATGTCGAATTTGATTCCCAGAGG

Reverse Primer:   ACGTTGGATGTCCCAGACTGAAATCCCAAG

Extend Primer:    ggggTGAAATCCCAAGACAATGGA

Extend Direction: R

Extend Allele:    C
```

FIGURE 1F

```
TTTY22-1

ACCAATGCAATGCACTAGTCTCAGGGCACCAGGCCTGAGCTGTGAGCTCTGGCTAGCATCACAATGAATGCCACCATT[G/*]CCT
AGCGACAAGTCCCTGCCATAAGGTAGAGAAGTAGCCCTTCGTGGAGGTGCACAGACCATGGATTCTTGCCTTCTTCTGTGTGGGGT
CCACAGGATATTCCCATAGTTCTAGGAGAGGACAGACATTAGCCTGCCTAAAGAAACATCAAGCAGAGCCCCAGGAATAAACTGTG
GAATTCCTAACGATTCAAAAAGATTTGCAGGATGCATCAGACCTGCC

Amplicon length:  98

Forward Primer:   ACGTTGGATGCTCTGGCTAGCATCACAATG

Reverse Primer:   ACGTTGGATGACGAAGGGCTACTTCTCTAC

Extend Primer:    GCAGGGACTTGTCGCTAGG

Extend Direction: R

Extend Allele:    G
```

FIGURE 1G

SRY_4-i

ACGTCCAGGATAGAGTGAAGCGACCCATGAACGCATTCATCGTGTGGTCTCGCGATCAGAGGCGCAAGATGGCTCTAGAGAATCCC
AGAATGCGAAACTC[A/*]GAGATCAGCAAGCAGCTGGGATACCAGTGGAAAATGCTTACTGAAGCCGAAAAATGGCCATTCTTCC
AGGAGGCACAGAAATTACAGGCCATGCACA

Amplicon length: 92

Forward Primer: ACGTTGGATGAGATGGCTCTAGAGAATCCC

Reverse Primer:  ACGTTGGATGGCATTTTCCACTGGTATCCC

Extend Primer:  CCAGAATGCGAAACTC

Extend Direction:  F

Extend Allele:  A

FIGURE 1H

XKRY-1

TATATCCTTTGAGTACGTATCTGGAAGTAGAGTAGCTGGATTATGTGGTAATTCTTATTTTTAATTTAACTGTATTTTTGAACACT
CAATTCTATGACCCCAAAAGCACAGACTAGAAAAGCACAACAAAAAACAATTGGATCACATTACATCAAA[C/*]TAAAATGTTTC
TGTACCACAGAGGGAAAAGGGTGAAAAGCAAATGTTCACTGATAGTGTATATGCTATATTACAAGCACTTATTAAATTAAAGGTAT
AGGTTCCAAAATGTACTAGGTGAAAAATGTATTATGGTTATTTTTTC

Amplicon length:  110

Forward Primer:  ACGTTGGATGATGACCCCAAAAGCACAGAC

Reverse Primer:  ACGTTGGATGTCCCTCTGTGGTACAGAAAC

Extend Primer:  CAATTGGATCACATTACATCAAA

Extend Direction:  F

Extend Allele:  C

FIGURE 1I

```
Alb-2-i

GCTCAGTATCTTCAGCAGTGTCCATTTGAAGAT[C/*]ATGTAAAATTAGTGAATGAAGTAACTGAATTTGC

Amplicon length:   85bp

Forward Primer:    ACGTTGGATGCAGTATCTTCAGCAGTGTCC

Reverse Primer:    ACGTTGGATGGCAAATTCAGTTACTTCATTC

Extend Primer:   GCAGTGTCCATTTGAAGAT

Extend Direction:   F

Extend Allele:   C
```

NUCLEIC ACID-BASED TESTS FOR PRENATAL GENDER DETERMINATION

RELATED PATENT APPLICATION

This patent application claims the benefit of U.S. Patent Application No. 61/035,711 filed on Mar. 11, 2008, entitled NUCLEIC ACID-BASED TESTS FOR PRENATAL GENDER DETERMINATION, naming Paul Oeth and Payam Mahboubi as inventors, and designated by. The entire content of the foregoing patent application is incorporated herein by reference, including all text, tables and drawings.

FIELD OF THE INVENTION

The invention relates in part to compositions, methods and kits for determining from an extracellular nucleic acid sample obtained from a pregnant female (i) the sex of a fetus, and/or (ii) the amount of fetal nucleic acid.

BACKGROUND

Early determination of fetal sex is medically relevant when there is a family history of sex dependent or X-linked disorders. The presence of cell free fetal (cff) DNA in maternal plasma allows for fetal genotyping at an earlier time point than either amniocentesis or chorionic villus sampling with lower risk to the fetus (Lo et al., Lancet 350, 485-487 (1997)). However, the total amount and relative proportion of cff DNA in maternal plasma is lower in earlier stages of pregnancy. Because of low relative amounts of cff DNA during the first trimester, assays for fetal sex determination must have extraordinary sensitivity and specificity, and must be able to detect Y-chromosomal sequences at very low copy numbers.

SUMMARY

Provided herein are compositions and processes for non-invasive, early determination of fetal sex. More specifically, the compositions and processes are useful for the detection of low genomic copy numbers of male DNA in a high copy number background of female DNA, thereby determining the sex of a fetus. The assay comprises a multiplexed PCR reaction to amplify a portion of the albumin (ALB) gene (which serves as a positive amplification control) and 8 Y-chromosomal targets to confirm the presence of male Y-chromosomal sequences. The multiple Y-chromosomal regions provide increased sensitivity while maintaining high specificity. The assay was designed to target gene-based Y-chromosome sequences (termed "ampliconic") primarily with testis-specific expression (see Table 1). With the exception of SRY and RBMY, Y-chromosomal sequences with evolutionary similarity to X-chromosomal sequences were avoided. Any PCR-based detection method may be used to determine the fetal sex using the methods and compositions provided herein. In some embodiments, PCR amplification is followed by a primer extension reaction (for example, Sequenom's TypePLEX™ assay) and detection of the extension products using mass spectrometry (for example, Sequenom's MassARRAY® System).

Methods described herein may be performed in conjunction with other noninvasive prenatal tests, for example, but not limited to, detecting the presence of fetal nucleic in a sample, determining the relative amount of fetal nucleic acid in a sample, testing for chromosomal abnormalities or determining fetal blood type or RhD compatibility, where each of the assays may be performed alone or in combination with methods of the present invention. Examples of RhD and fetal identifier assays are provided in U.S. patent application Ser. No. 12/027,954, which was filed Feb. 7, 2008, and is hereby incorporated by reference.

Provided herein are compositions and methods for determining fetal sex. In some embodiments, the compositions and methods of the invention may be used to determine the presence or absence of Y-chromosome nucleic acid in a sample from a pregnant female. In related embodiments, compositions and methods described herein may be used to determine the presence or absence of any of the genes in Table 1.

Also provided herein are compositions and methods that can be used to analyze a nucleic acid sample for the presence or absence of one or more Y-chromosome genes from Table 1, comprising the steps of amplifying the one or more Table 1 genes (or amplicons therein) with one or more primer pairs provided in Table 3; determining the presence or absence of the amplification products from the amplification reaction, thereby determining the sex of the fetus where the presence of one or more Y-chromosome amplification products indicates the presence of a male fetus and conversely the absence of one or more Y-chromosome amplification products indicates the presence of a female fetus. In related embodiments, the sample is blood from a pregnant female. In certain embodiments, the genes are analyzed in a multiplexed amplification reaction. In related embodiments, two or more multiplexed assays are performed in parallel. In certain embodiments, the sample is blood, plasma or serum from a pregnant female. In related embodiments, the sample contains fetal nucleic acid and maternal nucleic acid. In related embodiments, the primer pairs in Table 3 comprise a tag sequence to improve multiplexing. In certain embodiments, the presence or absence of amplification products is determined by mass spectrometry. In some embodiments, the presence or absence of amplification products is determined by detection of hybridization of the amplification products to a gene chip. In certain embodiments, the presence or absence of amplification products is determined by real time-PCR (alternatively called RT-PCR or Q-PCR).

In some embodiments, each primer of the amplification primer pair may comprise the entire sequence shown or only the non-underlined sequence, where the underlined portion of the primer is a tag sequence for improved multiplexing and the non-underlined portion is a sequence-specific primer sequence. The tag sequence may be any tag sequence known in the art that improves multiplexing. In certain embodiments, the invention in part includes primers having nucleotide sequences substantially identical to a nucleotide sequence of primers provided herein, for example, about 80%, 81%, 82%, 83%, 84%, 85%, 86%, 87%, 88%, 89%, 90%, 91%, 92%, 93%, 94%, 95%, 96%, 97%, 98%, 99% or 99% or more identical, or having only 1, 2, 3, 4, 5, 6, 7, 8, 9 or 10 mismatched nucleotides (e.g., mismatches are determined when the nucleotide sequences are aligned) and further where the primers still specifically hybridize to a given Y-chromosome region (e.g., gene). For example, one or more bases of a primer sequence may be changed or substituted, for example with an inosine, but the primer still maintains the same specificity and plexing ability.

Provided herein are compositions and methods to analyze a nucleic acid sample for the presence or absence of one or more Y-chromosome genes from Table 1, comprising the steps of amplifying the one or more Y-chromosome genes with the primer pairs provided in Table 3; hybridizing (e.g., annealing) one or more extend primers to the amplification products of the first step (e.g., examples of extend primers are provided in Table 3); performing a primer extension reaction;

and analyzing the primer extension products to determine the sex of a fetus. In certain embodiments, the presence or absence of primer extension products is determined by mass spectrometry. In certain embodiments, the presence or absence of primer extension products is determined by any method known in the art.

The invention is not limited by the detection method; therefore, the amplification products and/or primer extension products may be detected by any detection method, which includes but is not limited to, the use of hybridization probes and quantitative real time polymerase chain reaction (QRT-PCR), digital PCR, electrophoresis, pyrosequencing, primer extension, microarrays, chips and sequencing. In certain embodiments, detection of amplification products and/or extension products can be carried out using the single tube methods described in U.S. patent application Ser. No. 11/950, 395, which was filed Dec. 4, 2007, and is hereby incorporated by reference. In certain embodiments, whole genome sequencing methods may be utilized to detect nucleic acid from the Y-chromosome. Examples of whole genome sequencing methods include, but are not limited to, nanopore-based sequencing methods, sequencing by synthesis and sequencing by ligation.

In some embodiments, a primer extension reaction includes incorporation of a chain terminating nucleotide. In related embodiments, the chain terminating nucleotide is a dideoxynucleotide, dideoxybromouridine or acyclonucleotide. In certain embodiments, the extension reaction comprises incorporation of a deoxynucleotide, a dideoxynucleotide or a combination thereof. In certain embodiments, the extension reaction comprises incorporation of a labeled nucleotide. In related embodiments, the extension reaction comprises using a mixture of labeled and unlabeled nucleotides. In related embodiments, the labeled nucleotide is labeled with a molecule selected from the group consisting of radioactive molecule, fluorescent molecule, mass label, antibody, antibody fragment, hapten, carbohydrate, biotin, derivative of biotin, phosphorescent moiety, luminescent moiety, electrochemiluminescent moiety, chromatic moiety, and moiety having a detectable electron spin resonance, electrical capacitance, dielectric constant and electrical conductivity. In related embodiments, the labeled nucleotide is labeled with a fluorescent molecule.

In some embodiments the sample is blood from a pregnant female. In certain embodiments, the biological sample is from any animal, including but not limited to, human, non-human, mammal, reptile, cattle, cat, dog, goat, swine, pig, monkey, ape, gorilla, bull, cow, bear, horse, sheep, poultry, mouse, rat, lion, tiger, fish, dolphin, whale, and shark, or any animal or organism that may be subjected to prenatal gender determination.

Methods described herein are useful across a range of gestational ages (see Example 1). Thus in some embodiments, a sample is obtained from a human pregnant female when the fetus is at a gestational age selected from the group consisting of: 0-4, 4-8, 8-12, 12-16, 16-20, 20-24, 24-28, 28-32, 32-36, 36-40, 40-44, 44-48, 48-52, and more than 52 weeks. In related embodiments, the sample is obtained through non-invasive means. In certain embodiments, the nucleic acid is obtained from plasma from blood. In certain embodiments, the nucleic acid is obtained from serum from blood. In some embodiments, the biological sample contains cellular elements or cellular remnants in maternal blood.

In certain embodiments, the fetal nucleic acid may be extracted from maternal body fluids, sometimes whole blood, and often plasma or serum, using e.g. DNA extraction methods such as, but not limited to, gelatin extraction method; silica, glass bead, or diatom extraction method; guanidinium thiocyanate acid-phenol based extraction methods; guanidinium thiocyanate acid based extraction methods; guanidine-hydrochloride based extraction methods; methods using centrifugation through cesium chloride or similar gradients; phenol-chloroform based extraction methods; and/or other available DNA extraction methods, as are known in the art for use in extraction of intracellular DNA, including commercially available DNA extraction methods, e.g. by using or adapting or modifying the methods of Boom et al. (1990, J. Clin. Microbiol. 28: 495-503); Cheung et al. (1994, J. Clin. Microbiol. 32: 2593-2597); Boom et al. (1991, J. Clin. Microbiol. 29: 1804-1811); Chomczynski and Sacchi (1987, Analytical Biochem. 162: 156-159); Chomczynski, (1993, Biotech. 15: 532-537); Chomczynski and Mackey (1995, Biotechniques 19: 942-945); Chomczynski and Mackey (1995, Anal. Biochem. 225: 163-164); Chirgwin et al. (1979, Biochem. 18: 5294-5299); Fournie et al. (1986 Anal. Biochem. 158: 250-256); and WO97/35589.

While the invention is not limited by how the sample is obtained, methods and compositions described herein are particularly useful for assaying samples obtained by non-invasive means, which may contain lower amounts of fetal nucleic acid to be assayed. In related embodiments, the sample is processed to selectively enrich fetal nucleic acid. In certain embodiments, a sample is enriched or relatively enriched for fetal nucleic acid. Methods for enriching a sample for a particular species of nucleic acid are described, for example, in International Patent Application Number PCT/US07/69991, filed May 30, 2007, International Patent Application Number PCT/US2007/071232, filed Jun. 15, 2007, International Patent Application Number PCT/US2008/074689 and International Patent Application Number PCT/US2008/074692 and International Patent Application Number PCT/EP05/012707, which are all hereby incorporated by reference.

Multiplexed reactions can be utilized in methods described herein to improve throughput and reduce cost. Thus, provided herein are optimized methods for performing a primer mass extension assay, including an optimized PCR amplification reaction that produces amplified targets for subsequent multiplexed primer mass extension genotyping analysis using mass spectrometry. Also provided herein are optimized methods for performing multiplexed amplification reactions and multiplexed primer mass extension reactions in a single reaction vessel (e.g., single well or pit of plate or chip, or single reaction tube) to further increase the throughput and reduce the cost per genotype for primer mass extension reactions. Certain nucleic acid target-region amplification and primer mass extension genotyping reactions have been optimized herein to permit moderate to high level multiplexing reactions with greater efficiency and accuracy, while at the same time not adversely affecting the mass spectrometry analysis of mass extension products.

In some embodiments, the amplification primers provided in Table 3 comprises a 5' tag (underlined) and a gene-specific sequence. The tag can be used to assist in the amplification of the nucleic acids. The primer tags may serve to stabilize the primer during amplification or they may serve as universal primer sites. More specifically, once the target gene nucleic acids of Table 1 have been PCR amplified using the primers, primers to the tags are used to further amplify the sequences in certain embodiments. In some embodiments, both amplification steps are performed simultaneously. As will be appreciated by those skilled in the art, primers without the 5' tag can be used in the method of the invention to amplify the target gene nucleic acids. Alternatively, the primer sequences can comprise different tag sequences than the tags indicated in the Table. Tag sequences useful for multiplex amplification reactions are known in the art.

In certain embodiments, the amplification primers allow for sequence specific amplification. For example, the PCR primers are designed to discriminate against amplification of similar genes or paralogs that are on other chromosomes by taking advantage of sequence differences between the target nucleic acids of Table 1 and any paralogs from other chromosomes.

In particular embodiments, a sequence tag is attached to a plurality of primary and secondary primer pairs provided in Table 3. The sequence tag can be attached to either one or both of the primary and secondary primers from each pair. Typically, the sequence tag is attached to the primary and secondary primer of each pair. The sequence tags used herein can range from 5 up to 20, from 5 up to 30, from 5 up to 40, or from 5 up to 50 nucleotides in length, with a sequence tag of 10-mer length being particularly useful in the methods provided herein. The sequence tag need not be the same sequence for each primer pair in a multiplexed amplification reaction, nor the same sequence for a primary and secondary primer within a particular amplification pair. In a particular embodiment, the sequence tag is the same for each primer in the multiplexed amplification reaction. For example, in certain embodiments, the sequence tag is a 10-mer, such as -ACGTTGGATG- (SEQ ID NO: 186), and is attached to the 5' end of each primary and secondary primer. In particular embodiments of the methods provided herein, only a single primer pair is used to amplify each particular nucleic acid target-region (e.g., a "universal primer").

Methods and compositions described herein may be combined with other prenatal tests, including the use of fetal identifiers to detect the presence or absence of fetal nucleic acid in a maternal sample. Thus in some embodiments, fetal identifier compositions and methods are also provided for analyzing a plurality of polymorphisms in a nucleic acid sample of fetal origin; and analyzing a plurality of polymorphisms in a nucleic acid sample of maternal origin, whereby the presence of at least one polymorphism in the nucleic acid sample of fetal origin, which is not present in the nucleic acid sample of maternal origin, confirms the presence of fetal nucleic acid in the fetal nucleic acid sample. In related embodiments, the presence of at least one polymorphism in the nucleic acid sample of fetal origin, which is not present in the nucleic acid sample of maternal origin, is a paternally-inherited allele. In certain embodiments, the same polymorphisms are analyzed in fetal nucleic acid and maternal nucleic acid. In certain embodiments, the polymorphism is heterozygous. The plurality of polymorphisms may include 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, 600, 700, 800, 900, 1000 or more polymorphisms. In related embodiments, the polymorphism is a single nucleotide polymorphism (SNP), insertion/deletion, short tandem repeats (STRs), RFLPs or any other alternate form of a gene, genomic DNA or non-coding region of DNA that occupies the same position on a chromosome. The polymorphism may be naturally-occurring or synthetic. Synthetic polymorphisms may include alternative forms introduced on a synthetic oligonucleotide that serve as a competitor or control. In some embodiments, the sequence variation falls in a restriction site, whereby one allele is susceptible to digestion by a restriction enzyme and the one or more other alleles are not. In certain embodiments, the sequence variation is a methylation site.

In certain embodiments, a method for detecting the presence or absence of fetal nucleic acid in a sample comprises obtaining or possessing a nucleic acid sample known to be of maternal origin and suspected of comprising fetal nucleic acid; analyzing the nucleic acid sample to determine the maternal genotype of at one or more nucleotide polymorphisms; and analyzing the nucleic acid sample to determine the fetal genotype of one or more nucleotide polymorphisms, where a fetal genotype possessing a paternally-inherited allele indicates the presence of fetal nucleic acid. In related embodiments, the maternal genotypes are determined from DNA that is substantially free of fetal nucleic acid. For example, in the case when the sample is blood, the maternal genotypes may be determined from the portion of the blood that comprises nucleated maternal cells (e.g., white blood cells). In some embodiments, the DNA that is substantially free of fetal nucleic acid is from peripheral blood mononuclear cells. In certain embodiments, the amount of fetal DNA is determined by comparing the relative amount of paternally-inherited alleles to maternally-inherited alleles in fetal nucleic acid.

The invention in part also provides compositions and methods to determine the relative amount of target nucleic acid in a sample (e.g., fetal nucleic acid in a pregnant female sample). In some embodiments, compositions and methods described herein may be used to quantify the relative amount of the alleles at a heterozygous polymorphic site, where the heterozygous polymorphic site has been identified by determining the sequence of alleles at a polymorphic site from template DNA obtained from a maternal sample, where the relative amount is expressed as a ratio, and the ratio indicates the relative amount of fetal nucleic acid present in the maternal sample. In certain embodiments, the polymorphic site is an insertion/deletion, STR or RFLP.

In certain embodiments, the heterozygous polymorphic site is part of a restriction site, and a restriction enzyme is introduced that can discriminate between the alleles of the polymorphic site. The maternal allele is digested and the nucleic acid comprising the paternal allele is relatively enriched in some embodiments.

In certain embodiments, the total copy number of nucleic acid molecules for the human serum albumin (ALB) gene is determined. Methods for determining the total copy number of nucleic acid present in a sample comprise detecting albumin-specific extension products and comparing the relative amount of the extension products to competitors introduced to the sample. In related embodiments, Provided herein are compositions and methods to determine the relative amount of fetal DNA in a sample (e.g., plasma of a pregnant woman carrying a male fetus), which comprises annealing one or more albumin gene sequences to the fetal DNA; and analyzing the primer extension products to determine the relative amount of ALB extension products. The assay is useful to measure how much nucleic acid (e.g., total copy number) is present in a sample or loaded into a particular reaction. The assay may serve as an internal control and a guide to the likelihood of success for a particular PCR reaction.

In certain embodiments, the methods and compositions of the invention are used to detect Y-chromosome nucleic acid at low copy numbers. In some embodiments, the fetal nucleic acid copy number is about 5 to about 1000 copies, and sometimes about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 60, 70, 80, 90, 100, 150, 200, 250, 300, 350, 400, 500, 600, 700, 800, 900 or 1000 or more.

In certain embodiments, methods described herein include steps to reduce the introduction of non-fetal Y-chromosome. For example, samples sometimes are collected and/or processed by a female.

Embodiments of the invention are described further in the following brief description of the drawings, detailed description and claims.

BRIEF DESCRIPTION OF THE DRAWINGS

FIG. 1A-1I provide the location design of the fetal sex amplification and extend primers within the target nucleic acids. FIG. 1A discloses SEQ ID NOS 177, 9, 43 and 76, respectively, in order of appearance. FIG. 1B discloses SEQ ID NOS 178, 2, 36 and 69, respectively, in order of appearance. FIG. 1C discloses SEQ ID NOS 179, 40, 6 and 73, respectively, in order of appearance. FIG. 1D discloses SEQ ID NOS 180, 37, 3 and 70, respectively, in order of appearance. FIG. 1E discloses SEQ ID NOS 181, 8, 42 and 75, respectively, in order of appearance. FIG. 1F discloses SEQ ID NOS 182, 5, 39 and 72, respectively, in order of appearance. FIG. 1G discloses SEQ ID NOS 183, 35, 1 and 68, respectively, in order of appearance. FIG. 1H discloses SEQ ID NOS 184, 41, 7 and 74, respectively, in order of appearance. FIG. 1I discloses SEQ ID NOS 185, 38, 4 and 71, respectively, in order of appearance.

DETAILED DESCRIPTION

Figure 2:
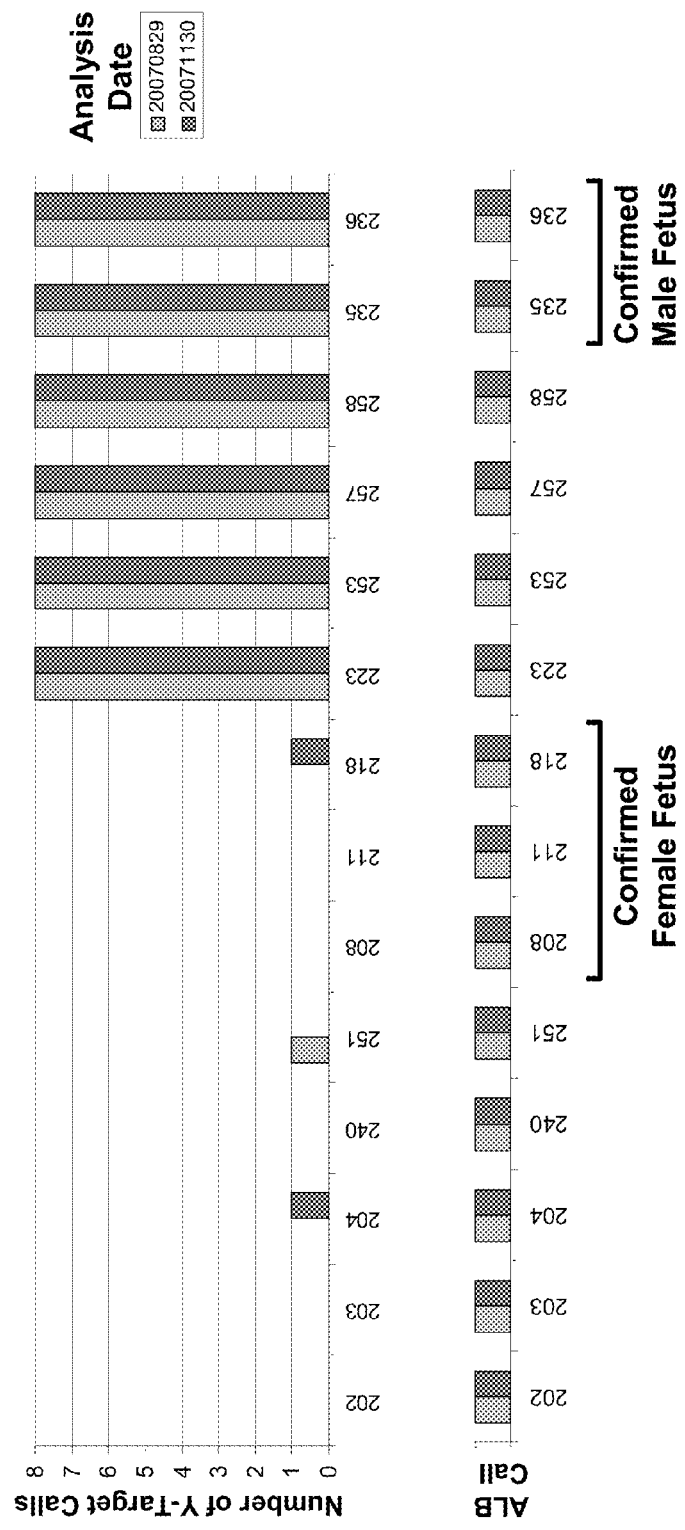
FIG. 2 shows results from the maternal plasma sample analysis. Samples were assayed in either August 2007 (20070829) or November 2007 (20071130) as indicated by the light and dark gray bars. The top panel shows the number of Y-target calls for each sample. Bottom panel shows the ALB call for each sample to indicate successful PCR. Samples within brackets at the bottom indicate fetal gender phenotype information for those where it was known.

Early determination of fetal sex is medically relevant, for example, when there is a family history of sex dependent or X-linked disorders such as congenital adrenal hyperplasia (CAH), Duchennes muscular dystrophy, hemophilia or Fragile X. The presence of fetal nucleic acid in maternal plasma allows for fetal genotyping at an earlier time point than either amniocentesis or chorionic villus sampling and with lower secondary risk to the fetus. However, cell-free fetal nucleic acid constitutes only a minority of the total DNA in maternal plasma (typically less than 6%) (Lo Y M et. al., Am J Hum Genet. 62, 768-75. 1998). Additionally, the total amount and relative proportion of fetal nucleic acid in maternal plasma is lowest in the first trimester when fetal sex determination is most relevant, especially in cases of CAH. Therefore, assays for fetal sex determination must be highly sensitive and specific.

In certain embodiments, assays comprises a multiplexed PCR to amplify a portion of the albumin (ALB) gene (which serves as a positive amplification control) and 8 Y-chromosomal targets to confirm the presence of male Y-chromosomal sequences. The Y-chromosomal markers used in the assay design were chosen from targets in the male specific regions of the Y-chromosome, and cover sites in both the long and short arm of the Y-chromosome. Markers include the genes and transcriptional units indicated in Table 1. An emphasis was placed on multi-copy loci because the nature of these targets is predicted to allow higher rates of detection in situations with low fetal copy numbers typically seen in maternal plasma at early stages of pregnancy. The multiple Y-chromosomal regions provide increased sensitivity while maintaining high specificity in such embodiments. The assays were designed to target gene-based Y-chromosome sequences (termed "ampliconic") primarily with testis-specific expression (Table 1). With the exception of SRY and RBMY, Y-chromosomal sequences with evolutionary similarity to X-chromosomal sequences were avoided.

TABLE 1

| Class | Gene/Txn Symbol | Gene/Txn Name | No. copies* | Tissue expression | X-linked homologue | Autosomal homologue |
|---|---|---|---|---|---|---|
| ampliconic | HSFY | Heat shock transcription factor Y | 2 | testis | — | — |
| | RBMY | RNA-binding motif Y | 6 | testis | RBMX | — |
| | PRY | PTP-BL related Y | 2 | testis | — | — |
| | BPY2 | Basic protein Y 2 | 3 | testis | — | — |
| | XKRY | XK related Y | 2 | testis | — | — |
| | CDY | Chromodomain | 4 | testis | — | CDYL |
| | TTTY | Non-coding transcription units | | — | — | — |
| X-degenerate | CYORF14 | Chromosome Y open reading frame 14 | | — | — | — |
| | SRY | Sex determining region Y | 1 | testis | SOX3 | — |

In some embodiments, PCR amplification is followed by a primer extension reaction and detection of the extension products using mass spectrometry. Other detection methods may be used to detect the amplification products or extension products.

In certain assay embodiments, initial testing on male and female genomic DNA showed the ability of the assay system to discriminate the presence or absence of Y-chromosomal DNA. Secondary studies were performed using DNA mixtures with as low as 20 genomic copies of either male or female DNA mixed with a 50-fold excess of female genomic DNA. Out of 88 total DNA mixtures, 40 female:female DNA mixtures were used to evaluate spurious amplification of individual Y-chromosomal targets. In 48 male:female DNA mixtures, ALB was amplified in all cases and all 8 Y-chromosomal target regions were detected consistently. These results demonstrate high sensitivity and specificity for accurately detecting Y-chromosomal DNA. Initial testing of the assay using maternal plasma and non-pregnant female plasma samples has been performed and shows a high degree of reproducibility between replicate sample aliquots of maternal plasma and high specificity as determined by the lack of Y-chromosomal target detection in plasma DNA isolated from non-pregnant female donors. Compared to other cell-free fetal nucleic acid tests for SRY, the use of methods and compositions described herein increases specificity of the assay while maintaining high sensitivity with utility for early determination of fetal sex in a clinical setting.

As used herein, "sample" refers to a composition containing a material to be detected or analyzed. Samples include "biological samples", which refer to any material obtained from a living source, for example, an animal such as a human or other mammal. The sample may be obtained through invasive (e.g., amniocentesis) or non-invasive (e.g., blood draw) means. In some embodiments, the sample is obtained non-invasively. The biological sample can be in any form that potentially includes fetal nucleic acid, including a solid material such as a tissue, cells, a cell pellet, a cell extract, or a biological fluid such as urine, whole blood, plasma, serum, interstitial fluid, vaginal swab, pap smear, peritoneal fluid, sweat, saliva, follicular fluid, breast milk, non-milk breast secretions, cerebral spinal fluid, seminal fluid, lung sputum, amniotic fluid, a mouth wash containing buccal cells, synovial fluid, or any other fluid sample produced by the subject. If desired, solid materials can be mixed with a fluid or purified or amplified or otherwise treated. Samples examined using the methods described herein can be treated in one or more purification steps in order to increase the purity of the desired cells or nucleic acid in the sample. Samples also can be examined using the methods described herein without any purification steps to increase the purity or relative concentration of desired cells or nucleic acid. As used herein, the term "blood" encompasses whole blood or any fractions of blood, such as serum and plasma as conventionally defined. In certain embodiments, nucleic acid is isolated from a sample that is cell free, acellular or extracellular (e.g., blood plasma, blood serum, urine).

The terms "nucleic acid" and "nucleic acid molecule" may be used interchangeably throughout the disclosure. The terms refer to a deoxyribonucleotide (DNA), ribonucleotide polymer (RNA), RNA/DNA hybrids and polyamide nucleic acids (PNAs) in either single- or double-stranded form, and unless otherwise limited, would encompass known analogs of natural nucleotides that can function in a similar manner as naturally occurring nucleotides. In the case of RNA or mRNA, a DNA copy (cDNA) of the RNA transcript of interest often is synthesized. This synthesis often is achieved by reverse transcription, which can be carried out as a separate step in certain embodiments. In a homogeneous reverse transcription-polymerase chain reaction (RT-PCR) embodiment, a modification of the polymerase chain reaction for amplifying RNA.

As used herein, the term "multiplexing" refers to simultaneous amplification and/or primer mass extension reaction of more than one oligonucleotide or primer (e.g., in a single reaction container); or the simultaneous analysis of more than one oligonucleotide, in a single mass spectrometric or other mass measurement, i.e., a single mass spectrum or other method of reading sequence. Examples of different multiplex schemes (MP1, MP2, MP3 and MP4) are provided in Table 3.

As used herein, the phrase "target nucleic acid" refers to one or more nucleic acids, such as genomic DNA, from which one or more regions or loci are to be amplified. As used herein, the phrase "nucleic acid-target region" refers to the region-specific areas or loci of a target nucleic acid (e.g., UTR, exon or intron) that are amplified for subsequent fetal sex determination. For example, FIGS. 1A-1I provide target nucleic acid regions from the genes listed in Table 1.

As used herein, the term "polymorphism" refers to the coexistence of more than one form or allele of a nucleic acid, such as a chromosome, or portion thereof. For example, a portion or locus of a gene at which there are at least two different alleles, i.e., two different nucleotide sequences, is referred to as a polymorphic loci, site or region of a gene. A polymorphic loci can be a single nucleotide (e.g., SNP) or can be several nucleotides in length (e.g., insertions or deletions). Accordingly, polymorphism includes substitutions, insertions, duplications and deletions of nucleotides. A polymorphism can also refer to a particular nucleotide(s) or nucleotide sequence occurring at a particular polymorphic site.

As used herein, the term "genotyping" refers to the process of determining the particular nucleotide or nucleotides (e.g., sequence variation) either present or absent at a particular polymorphic loci or genomic location. As used herein, the term "genotype" refers to the identity of the alleles or non-homologous variants present in an individual or sample. The term "genotyping a sample" or "genotyping an individual" refers to determining a specific allele or specific nucleotide(s) in a sample or carried by an individual at particular region(s).

As used herein, the term "allele" refers to a variant at a particular locus, namely a nucleic acid sequence variant (e.g., sequence variations such as single nucleotide polymorphisms, copy number variations, short tandem repeats (STRs), insertion/deletion polymorphisms and methylation sites), at the particular locus of interest. A locus is a site on a chromosome or, for example, a transcript thereof. When a subject has two identical alleles of a polymorphic region within a gene, the subject is said to be homozygous for the allele. When a subject has two different alleles of a polymorphic region within a gene, the subject is said to be heterozygous for the allele.

Amplification

In some embodiments, it may be desirable to amplify a target sequence using any of several nucleic acid amplification procedures (described in greater detail herein). Nucleic acid amplification may be particularly beneficial when target sequences exist at low copy number, or the target sequences are non-host sequences and represent a small portion of the total nucleic acid in the sample (e.g., fetal nucleic acid in a maternal nucleic acid background). In some embodiments, amplification of target sequences may aid in detection of one or more Y-chromosome nucleotide sequences, for example.

Nucleic acid amplification often involves enzymatic synthesis of nucleic acid amplicons (copies), which contain a sequence complementary to a nucleotide sequence species being amplified. An amplification product (amplicon) of a particular nucleotide sequence species (e.g., target sequence) is referred to herein as an "amplified nucleic acid species." Amplifying target sequences and detecting the amplicon synthesized, can improve the sensitivity of an assay, since fewer target sequences are needed at the beginning of the assay, and can improve detection of target sequences.

The terms "amplify", "amplification", "amplification reaction", or "amplifying" refers to any in vitro process for multiplying the copies of a target sequence of nucleic acid. Amplification sometimes refers to an "exponential" increase in target nucleic acid. However, "amplifying" as used herein can also refer to linear increases in the numbers of a select target sequence of nucleic acid, but is different than a one-time, single primer extension step. In some embodiments a limited amplification reaction, also known as pre-amplification, can be performed. Pre-amplification is a method in which a limited amount of amplification occurs due to a small number of cycles, for example 10 cycles, being performed. Pre-amplification can allow some amplification, but stops amplification prior to the exponential phase, and typically produces about 500 copies of the desired nucleotide sequence(s). Use of pre-amplification may also limit inaccuracies associated with depleted reactants in standard polymerase chain reaction (PCR) reactions, and also may reduce amplification biases due to nucleotide sequence or species abundance of the target. In some embodiments, a one-time primer extension may be used may be performed as a prelude to linear or exponential amplification. In some embodiments, amplification of the target nucleic acid may not be required, due to the use of ultra sensitive detections methods (e.g., single nucleotide sequencing, sequencing by synthesis and the like).

Based on the 5' and 3' primers that are chosen, amplification often serves to restrict and define a target-region or locus of the genome subject to analysis. Amplification can be by any process known, and in particular embodiments, includes the use of PCR. The phrase "simultaneous amplification" as used herein refers to amplification of two or more nucleic acid target-regions at the same time. Simultaneous amplification often is performed within the same amplification mixture. As used herein, the phrase "simultaneous amplification" refers to the multiplexed amplification of two or more loci or nucleic acid target-regions in a single reaction mixture. Simultaneous amplification therefore encompasses 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 30 or more, 40 or more, 50 or more, 60 or more, 70 or more, 80 or more, 100 or more, 200 or more, 500 or more, 1000 or more, 2000 or more amplification reactions. Amplification of each particular target-region occurs in parallel at the same time. Although it is contemplated herein that the simultaneous amplifications can occur in separate reaction mixtures, for the methods provided herein the simultaneous amplification reactions typically occur in the same single reaction. Likewise multiplexed primer mass extension refers to the simultaneous extension of 2 or more extend primers in a single reaction mixture. Accordingly, multiplexed primer mass extension therefore encompasses 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 30 or more, 40 or more, 50 or more, 60 or more, 70 or more, 80 or more, 100 or more, 200 or more, 500 or more, 1000 or more, 2000 or more primer mass extension reactions. Multiplexed amplification and primer mass extension reactions also encompass 21, 22, 23, 24, 24, 25, 26, 27, 28, 29, 30, 35, 40, 45, 50, 60, 70, 80, 100, 1000 or more reactions.

Where amplification may be desired, any suitable amplification technique can be utilized. Non-limiting examples of methods for amplification of polynucleotides include, polymerase chain reaction (PCR); ligation amplification (or ligase chain reaction (LCR)); amplification methods based on the use of Q-beta replicase or template-dependent polymerase (see US Patent Publication Number US20050287592); helicase-dependant isothermal amplification (Vincent et al., "Helicase-dependent isothermal DNA amplification". EMBO reports 5 (8): 795-800 (2004)); strand displacement amplification (SDA); thermophilic SDA nucleic acid sequence based amplification (3SR or NASBA) and transcription-associated amplification (TAA). Non-limiting examples of PCR amplification methods include standard PCR, AFLP-PCR, Allele-specific PCR, Alu-PCR, Asymmetric PCR, Colony PCR, Hot start PCR, Inverse PCR (IPCR), In situ PCR (ISH), Intersequence-specific PCR (ISSR-PCR), Long PCR, Multiplex PCR, Nested PCR, Quantitative PCR, Reverse Transcriptase PCR (RT-PCR), Real Time PCR, Single cell PCR, Solid phase PCR, combinations thereof, and the like. Reagents and hardware for conducting PCR are commercially available.

In some embodiments, amplification of Y-chromosome loci described herein may be accomplished by any suitable method available to one of skill in the art or selected from the listing above (e.g., ligase chain reaction (LCR), transcription-mediated amplification, and self-sustained sequence replication or nucleic acid sequence-based amplification (NASBA)). More recently developed branched-DNA technology may also be used to amplify the signal of the Y-chromosome loci described herein. For a review of branched-DNA (bDNA) signal amplification for direct quantification of nucleic acid sequences in clinical samples, see Nolte, Adv. Clin. Chem. 33:201-235, 1998.

Amplification also can be accomplished using digital PCR, in certain embodiments (e.g., Kalinina and colleagues (Kalinina et al., "Nanoliter scale PCR with TaqMan detection." Nucleic Acids Research. 25; 1999-2004, (1997); Vogelstein and Kinzler (Digital PCR. Proc Natl Acad Sci USA. 96; 9236-41, (1999); PCT Patent Publication No. WO05023091A2 (incorporated herein in its entirety); US Patent Publication No. 20070202525 (incorporated herein in its entirety)). Digital PCR takes advantage of nucleic acid (DNA, cDNA or RNA) amplification on a single molecule level, and offers a highly sensitive method for quantifying low copy number nucleic acid. Systems for digital amplification and analysis of nucleic acids are available (e.g., Fluidigm® Corporation).

In some embodiments, where RNA nucleic acid species may be used for detection of certain nucleotide sequences (e.g., fetal nucleotide sequences), a DNA copy (cDNA) of the RNA transcripts of interest can be synthesized prior to the amplification step. The cDNA copy can be synthesized by reverse transcription, which may be carried out as a separate step, or in a homogeneous reverse transcription-polymerase chain reaction (RT-PCR), a modification of the polymerase chain reaction for amplifying RNA. Methods suitable for PCR amplification of ribonucleic acids are described by Romero and Rotbart in Diagnostic Molecular Biology: Principles and Applications pp. 401-406; Persing et al., eds., Mayo Foundation, Rochester, Minn., 1993; Egger et al., J. Clin. Microbiol. 33:1442-1447, 1995; and U.S. Pat. No. 5,075,212.

Use of a primer extension reaction also can be applied in methods of the invention. A primer extension reaction operates, for example, by discriminating nucleic acid sequences, SNP alleles for example, at a single nucleotide mismatch (e.g., a mismatch between paralogous sequences, or SNP alleles). The terms "paralogous sequence" or "paralogous sequences" refer to sequences that have a common evolutionary origin but which may be duplicated over time in the genome of interest. Paralogous sequences may conserve gene structure (e.g., number and relative position of introns and exons and sometimes transcript length), as well as sequence. Therefore, the methods described herein can be used to detect sequence mismatches in SNP-alleles or in evolutionarily conserved regions that differ by one or more point mutations, insertions or deletions (both will hereinafter be referred to as "mismatch site" or "sequence mismatch").

The mismatch may be detected by the incorporation of one or more deoxynucleotides and/or dideoxynucleotides to a primer extension primer or oligonucleotide, which hybridizes to a region adjacent to the SNP site (e.g., mismatch site). The extension oligonucleotide generally is extended with a polymerase. In some embodiments, a detectable tag or detectable label is incorporated into the extension oligonucleotide or into the nucleotides added on to the extension oligonucleotide (e.g., biotin or streptavidin). The extended oligonucleotide can be detected by any known suitable detection process (e.g., mass spectrometry; sequencing processes). In some embodiments, the mismatch site is extended only by one or two complementary deoxynucleotides or dideoxynucleotides that are tagged by a specific label or generate a primer extension product with a specific mass, and the mismatch can be discriminated and quantified.

For embodiments using primer extension to amplify a target sequence, the primer extension is not limited to a single round of extension, and is therefore distinguished from "one-time primer extension" described above. Non-limiting examples of primer extension or oligonucleotide extension methods suitable for use with embodiments described herein are described in U.S. Pat. Nos. 4,656,127; 4,851,331; 5,679,524; 5,834,189; 5,876,934; 5,908,755; 5,912,118; 5,976,802; 5,981,186; 6,004,744; 6,013,431; 6,017,702; 6,046,005; 6,087,095; 6,210,891; and WO 01/20039, for example.

A generalized description of an amplification process is presented herein. Primers and target nucleic acid are contacted, and complementary sequences anneal to one another, for example. Primers can anneal to a nucleic acid, at or near (e.g., adjacent to, abutting, and the like) a target sequence of interest. A reaction mixture, containing all components necessary for full enzymatic functionality, is added to the primer-target nucleic acid hybrid, and amplification can occur under suitable conditions. Components of an amplification reaction may include, but are not limited to, e.g., primers (e.g., individual primers, primer pairs, primer sets and the like) a polynucleotide template (e.g., nucleic acid containing a target sequence), polymerase, nucleotides, dNTPs and the like. In some embodiments, non-naturally occurring nucleotides or nucleotide analogs, such as analogs containing a detectable label (e.g., fluorescent or calorimetric label) may be used, for example. Polymerases can be selected by a person of ordinary skill and include polymerases for thermocycle amplification (e.g., Taq DNA Polymerase; Q-Bio™ Taq DNA Polymerase (recombinant truncated form of Taq DNA Polymerase lacking 5'-3'exo activity); SurePrime™ Polymerase (chemically modified Taq DNA polymerase for "hot start" PCR); Arrow™ Taq DNA Polymerase (high sensitivity and long template amplification)) and polymerases for thermostable amplification (e.g., RNA polymerase for transcription-mediated amplification (TMA) described at World Wide Web URL "gen-probe.com/pdfs/tma_whiteppr.pdf"). Other enzyme components can be added, such as reverse transcriptase for transcription mediated amplification (TMA) reactions, for example.

The terms "near" or "adjacent to" when referring to a nucleotide target sequence refers to a distance or region between the end of the primer and the nucleotide or nucleotides of interest. As used herein adjacent is in the range of about 5 nucleotides to about 500 nucleotides (e.g., about 5 nucleotides away from nucleotide of interest, about 10, about 20, about 30, about 40, about 50, about 60, about 70, about 80, about 90, about 100, about 150, about 200, about 250, about 300, abut 350, about 400, about 450 or about 500 nucleotides from a nucleotide of interest).

Each amplified nucleic acid species independently can be about 10 to about 1000 base pairs in length in some embodiments. In certain embodiments, an amplified nucleic acid species is about 20 to about 250 base pairs in length, sometimes is about 50 to about 150 base pairs in length and sometimes is about 100 base pairs in length. Thus, in some embodiments, the length of each of the amplified nucleic acid species products independently is about 10, 15, 20, 25, 30, 35, 40, 45, 50, 55, 60, 65, 70, 75, 80, 82, 84, 86, 88, 90, 92, 94, 96, 98, 100, 102, 104, 106, 108, 110, 112, 114, 116, 118, 120, 125, 130, 135, 140, 145, 150, 175, 200, 250, 300, 350, 400, 450, 500, 550, 600, 650, 700, 750, 800, 850, 900, 950 or 1000 base pairs (bp) in length.

An amplification product may include naturally occurring nucleotides, non-naturally occurring nucleotides, nucleotide analogs and the like and combinations of the foregoing. An amplification product often has a nucleotide sequence that is identical to or substantially identical to a target sequence or complement thereof. A "substantially identical" nucleotide sequence in an amplification product will generally have a high degree of sequence identity to the nucleotide sequence species being amplified or complement thereof (e.g., about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater than 99% sequence identity), and variations sometimes are a result of infidelity of the polymerase used for extension and/or amplification, or additional nucleotide sequence(s) added to the primers used for amplification.

PCR conditions can be dependent upon primer sequences, target abundance, and the desired amount of amplification, and therefore, one of skill in the art may choose from a number of PCR protocols available (see, e.g., U.S. Pat. Nos. 4,683,195 and 4,683,202; and PCR Protocols: A Guide to Methods and Applications, Innis et al., eds, 1990. PCR often is carried out as an automated process with a thermostable enzyme. In this process, the temperature of the reaction mixture is cycled through a denaturing region, a primer-annealing region, and an extension reaction region automatically. Machines specifically adapted for this purpose are commercially available. A non-limiting example of a PCR protocol that may be suitable for embodiments described herein is, treating the sample at 95° C. for 5 minutes; repeating forty-five cycles of 95° C. for 1 minute, 59° C. for 1 minute, 10 seconds, and 72° C. for 1 minute 30 seconds; and then treating the sample at 72° C. for 5 minutes. Multiple cycles frequently are performed using a commercially available thermal cycler. Suitable isothermal amplification processes known and selected by the person of ordinary skill in the art also may be applied, in certain embodiments.

In some embodiments, multiplex amplification processes may be used to amplify target sequences, such that multiple amplicons are simultaneously amplified in a single, homogenous reaction. As used herein "multiplex amplification" refers to a variant of PCR where simultaneous amplification of many target sequences in one reaction vessel may be accomplished by using more than one pair of primers (e.g., more than one primer set). Multiplex amplification may be useful for analysis of deletions, mutations, and polymorphisms, or quantitative assays, in some embodiments. In certain embodiments multiplex amplification may be used for detecting paralog sequence imbalance, genotyping applications where simultaneous analysis of multiple markers is required, detection of pathogens or genetically modified organisms, or for microsatellite analyses. In some embodiments multiplex amplification may be combined with another amplification (e.g., PCR) method (e.g., nested PCR or hot start PCR, for example) to increase amplification specificity and reproducibility. In some embodiments, multiplex amplification processes may be used to amplify the Y-chromosome loci described herein.

In certain embodiments, nucleic acid amplification can generate additional nucleic acid species of different or substantially similar nucleic acid sequence. In certain embodiments described herein, contaminating or additional nucleic acid species, which may contain sequences substantially complementary to, or may be substantially identical to, the target sequence, can be useful for sequence quantification, with the proviso that the level of contaminating or additional sequences remains constant and therefore can be a reliable marker whose level can be substantially reproduced. Additional considerations that may affect sequence amplification reproducibility are; PCR conditions (number of cycles, volume of reactions, melting temperature difference between primers pairs, and the like), concentration of target nucleic acid in sample (e.g. fetal nucleic acid in maternal nucleic acid background, viral nucleic acid in host background), the number of chromosomes on which the nucleotide species of interest resides (e.g., paralogous sequences or SNP-alleles), variations in quality of prepared sample, and the like. The terms "substantially reproduced" or "substantially reproducible" as used herein refer to a result (e.g., quantifiable amount of nucleic acid) that under substantially similar conditions would occur in substantially the same way about 75% of the time or greater, about 80%, about 85%, about 90%, about 95%, or about 99% of the time or greater.

In some embodiments, amplification may be performed on a solid support. In some embodiments, primers may be associated with a solid support. In certain embodiments, target nucleic acid (e.g., template nucleic acid or target sequences) may be associated with a solid support. A nucleic acid (primer or target) in association with a solid support often is referred to as a solid phase nucleic acid.

In some embodiments, nucleic acid molecules provided for amplification are in a "microreactor". As used herein, the term "microreactor" refers to a partitioned space in which a nucleic acid molecule can hybridize to a solid support nucleic acid molecule. Examples of microreactors include, without limitation, an emulsion globule (described hereafter) and a void in a substrate. A void in a substrate can be a pit, a pore or a well (e.g., microwell, nanowell, picowell, micropore, or nanopore) in a substrate constructed from a solid material useful for containing fluids (e.g., plastic (e.g., polypropylene, polyethylene, polystyrene) or silicon) in certain embodiments. Emulsion globules are partitioned by an immiscible phase as described in greater detail hereafter. In some embodiments, the microreactor volume is large enough to accommodate one solid support (e.g., bead) in the microreactor and small enough to exclude the presence of two or more solid supports in the microreactor.

The term "emulsion" as used herein refers to a mixture of two immiscible and unblendable substances, in which one substance (the dispersed phase) often is dispersed in the other substance (the continuous phase). The dispersed phase can be an aqueous solution (i.e., a solution comprising water) in certain embodiments. In some embodiments, the dispersed phase is composed predominantly of water (e.g., greater than 70%, greater than 75%, greater than 80%, greater than 85%, greater than 90%, greater than 95%, greater than 97%, greater than 98% and greater than 99% water (by weight)). Each discrete portion of a dispersed phase, such as an aqueous dispersed phase, is referred to herein as a "globule" or "microreactor." A globule sometimes may be spheroidal, substantially spheroidal or semi-spheroidal in shape, in certain embodiments.

The terms "emulsion apparatus" and "emulsion component(s)" as used herein refer to apparatus and components that can be used to prepare an emulsion. Non-limiting examples of emulsion apparatus include without limitation counter-flow, cross-current, rotating drum and membrane apparatus suitable for use by a person of ordinary skill to prepare an emulsion. An emulsion component forms the continuous phase of an emulsion in certain embodiments, and includes without limitation a substance immiscible with water, such as a component comprising or consisting essentially of an oil (e.g., a heat-stable, biocompatible oil (e.g., light mineral oil)). A biocompatible emulsion stabilizer can be utilized as an emulsion component. Emulsion stabilizers include without limitation Atlox 4912, Span 80 and other biocompatible surfactants.

In some embodiments, components useful for biological reactions can be included in the dispersed phase. Globules of the emulsion can include (i) a solid support unit (e.g., one bead or one particle); (ii) sample nucleic acid molecule; and (iii) a sufficient amount of extension agents to elongate solid phase nucleic acid and amplify the elongated solid phase nucleic acid (e.g., extension nucleotides, polymerase, primer). Inactive globules in the emulsion may include a subset of these components (e.g., solid support and extension reagents and no sample nucleic acid) and some can be empty (i.e., some globules will include no solid support, no sample nucleic acid and no extension agents).

Emulsions may be prepared using known suitable methods (e.g., Nakano et al. "Single-molecule PCR using water-in-oil emulsion;" Journal of Biotechnology 102 (2003) 117-124). Emulsification methods include without limitation adjuvant methods, counter-flow methods, cross-current methods, rotating drum methods, membrane methods, and the like. In certain embodiments, an aqueous reaction mixture containing a solid support (hereafter the "reaction mixture") is prepared and then added to a biocompatible oil. In certain embodiments, the reaction mixture may be added dropwise into a spinning mixture of biocompatible oil (e.g., light mineral oil (Sigma)) and allowed to emulsify. In some embodiments, the reaction mixture may be added dropwise into a cross-flow of biocompatible oil. The size of aqueous globules in the emulsion can be adjusted, such as by varying the flow rate and speed at which the components are added to one another, for example.

The size of emulsion globules can be selected by the person of ordinary skill in certain embodiments based on two competing factors: (i) globules are sufficiently large to encompass one solid support molecule, one sample nucleic acid molecule, and sufficient extension agents for the degree of elongation and amplification required; and (ii) globules are sufficiently small so that a population of globules can be amplified by conventional laboratory equipment (e.g., thermocycling equipment, test tubes, incubators and the like). Globules in the emulsion can have a nominal, mean or average diameter of about 5 microns to about 500 microns, about 10 microns to about 350 microns, about 50 to 250 microns, about 100 microns to about 200 microns, or about 5, 10, 15, 20, 25, 30, 35, 40, 45, 50, 55, 60, 65, 70, 75, 80, 85, 90, 95, 100, 200, 300, 400 or 500 microns in certain embodiments.

In certain embodiments, amplified nucleic acid species in a set are of identical length, and sometimes the amplified nucleic acid species in a set are of a different length. For example, one amplified nucleic acid species may be longer than one or more other amplified nucleic acid species in the set by about 1 to about 100 nucleotides (e.g., about 2, 3, 4, 5, 6, 7, 8, 9, 10, 11, 12, 13, 14, 15, 16, 17, 18, 19, 20, 30, 40, 50, 60, 70, 80 or 90 nucleotides longer).

In some embodiments, a ratio can be determined for the amount of one amplified nucleic acid species in a set to the amount of another amplified nucleic acid species in the set (hereafter a "set ratio"). In some embodiments, the amount of one amplified nucleic acid species in a set is about equal to the amount of another amplified nucleic acid species in the set (i.e., amounts of amplified nucleic acid species in a set are about 1:1), which generally is the case when the number of chromosomes or the amount of DNA representative of nucleic acid species in a sample bearing each nucleotide sequence species amplified is about equal. The term "amount" as used herein with respect to amplified nucleic acid species refers to any suitable measurement, including, but not limited to, copy number, weight (e.g., grams) and concentration (e.g., grams per unit volume (e.g., milliliter); molar units). In some embodiments, the ratio of fetal nucleic acid to maternal nucleic acid (or conversely maternal nucleic acid to fetal nucleic acid) can be used in conjunction with measurements of the ratios of mismatch sequences for determination of chromosomal abnormalities possibly associated with sex chromosomes. That is, the percentage of fetal nucleic acid detected in a maternal nucleic acid background or the ratio of fetal to maternal nucleic acid in a sample, can be used in conjunction with the determination of the ratio Y-chromosome specific loci (e.g., the loci listed in Table 1) to detect chromosomal aneuploidies.

In certain embodiments, the amount of one amplified nucleic acid species in a set can differ from the amount of another amplified nucleic acid species in a set, even when the number of chromosomes in a sample bearing each nucleotide sequence species amplified is about equal. In some embodiments, amounts of amplified nucleic acid species within a set may vary up to a threshold level at which an outcome (e.g., (i) sex determination, (ii) presence or absence of Y-chromosome nucleic acid or (iii) amount of fetal nucleic acid) can be called with a confidence level of about 95% (e.g., about 90, 91, 92, 93, 94, 95, 96, 97, 98, 99, or greater than 99%). In certain embodiments, the amounts of the amplified nucleic acid species in a set vary by about 50% or less (e.g., about 45, 40, 35, 30, 25, 20, 15, 10, 5, 4, 3, 2 or 1%, or less than 1%). Thus, in certain embodiments amounts of amplified nucleic acid species in a set may vary from about 1:1 to about 1:1.5. Without being limited by theory, certain factors can lead to the observation that the amount of one amplified nucleic acid species in a set can differ from the amount of another amplified nucleic acid species in a set, even when the number of chromosomes in a sample bearing each nucleotide sequence species amplified is about equal. Such factors may include different amplification efficiency rates and/or amplification from a chromosome not intended in the assay design.

Each amplified nucleic acid species in a set generally is amplified under conditions that amplify that species at a substantially reproducible level. The term "substantially reproducible level" as used herein refers to consistency of amplification levels for a particular amplified nucleic acid species per unit template nucleic acid (e.g., per unit template nucleic acid that contains the particular nucleotide sequence species amplified). A substantially reproducible level varies by about 1% or less in certain embodiments, after factoring the amount of template nucleic acid giving rise to a particular amplification nucleic acid species (e.g., normalized for the amount of template nucleic acid). In some embodiments, a substantially reproducible level varies by 5%, 4%, 3%, 2%, 1.5%, 1%, 0.5%, 0.1%, 0.05%, 0.01%, 0.005% or 0.001% after factoring the amount of template nucleic acid giving rise to a particular amplification nucleic acid species.

In some embodiments amplification nucleic acid species (e.g., amplified target sequences) of primer sets may be generated in one reaction vessel. In some embodiments amplification of mismatch sequences may be performed in a single reaction vessel. In certain embodiments, mismatch sequences (on the same or different chromosomes) may be amplified by a single primer pair or set. In some embodiments target sequences may be amplified by a single primer pair or set. In some embodiments target sequences in a set may be amplified with two or more primer pairs.

Primers

Primers useful for amplification, detection, quantification and sequencing of Y-chromosome loci described herein, for example, are provided. In some embodiments the primers may be complementary to, and hybridize or anneal specifically to or near (e.g., adjacent to) sequences that flank a target region therein. In some embodiments primers are used in sets, where a set contains at least a pair. In some embodiments a set of primers may include a third or a fourth nucleic acid (e.g., two pairs of primers or nested sets of primers, for example). A plurality of primer pairs may constitute a primer set in certain embodiments (e.g., about 2, 3, 4, 5, 6, 7, 8, 9, 10, 15, 20, 25, 30, 35, 40, 45, 50, 55, 60, 65, 70, 75, 80, 85, 90, 95 or 100 pairs). In some embodiments a plurality of primer sets, each set comprising pair(s) of primers, may be used.

The term "primer" as used herein refers to a nucleic acid that comprises a nucleotide sequence capable of hybridizing or annealing to a target nucleic acid, at or near (e.g., adjacent to) a specific region of interest. As used herein, the term "PCR primer(s)" refers to oligonucleotides that can be used in a polymerase chain reaction (PCR) to amplify a nucleotide sequence originated from a Y-chromosome loci described herein, for example. In certain embodiments, at least one of the PCR primers for amplification of a nucleotide sequence encoding a Y-chromosome loci described herein can be sequence-specific for the locus (e.g., sequence specific for one of the loci described in Table 1). In some embodiments, primers may be modified (e.g., addition of a universal primer sequence) to improve multiplexing.

Primers can allow for specific determination of a target nucleic acid nucleotide sequence or detection of the target nucleic acid sequence (e.g., presence or absence of a sequence or copy number of a sequence), or feature thereof, for example. Primers may also be used to detect amplification products or extension products, in certain embodiments. A primer may be naturally occurring or synthetic. The term "specific", "specifically" or "specificity", as used herein with respect to nucleic acids, refers to the binding or hybridization of one molecule to another molecule, such as a primer for a target polynucleotide sequence. That is, "specific", "specifically" or "specificity" refers to the recognition, contact, and formation of a stable complex between two molecules, as compared to substantially less recognition, contact, or complex formation of either of those two molecules with other molecules. As used herein, the term "anneal" refers to the formation of a stable complex between two molecules. The terms "primer", "oligo", or "oligonucleotide" may be used interchangeably throughout the document, when referring to primers.

A primer nucleic acid can be designed and synthesized using suitable processes, and may be of any length suitable for hybridizing to a nucleotide sequence of interest (e.g., where the nucleic acid is in liquid phase or bound to a solid support) and performing analysis processes described herein. Primers may be designed based upon a target nucleotide sequence. A primer in some embodiments may be about 10 to about 100 nucleotides, about 10 to about 70 nucleotides, about 10 to about 50 nucleotides, about 15 to about 30 nucleotides, or about 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 nucleotides in length. A primer may be composed of naturally occurring and/or non-naturally occurring nucleotides (e.g., labeled nucleotides), or a mixture thereof. Primers suitable for use with embodiments described herein may be synthesized and labeled using known techniques. Oligonucleotides (e.g., primers) may be chemically synthesized according to the solid phase phosphoramidite triester method first described by Beaucage and Caruthers, Tetrahedron Letts., 22:1859-1862, 1981, using an automated synthesizer, as described in Needham-VanDevanter et al., Nucleic Acids Res. 12:6159-6168, 1984. Purification of oligonucleotides can be effected by native acrylamide gel electrophoresis or by anion-exchange high-performance liquid chromatography (HPLC), for example, as described in Pearson and Regnier, J. Chrom., 255:137-149, 1983.

All or a portion of a primer nucleic acid sequence (naturally occurring or synthetic) may be substantially complementary to a target nucleic acid sequence, in some embodiments. As referred to herein, "substantially complementary" with respect to sequences refers to nucleotide sequences that will hybridize with each other. The stringency of the hybridization conditions can be altered to tolerate varying amounts of sequence mismatch. Included are regions of counterpart, target and capture nucleotide sequences 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more complementary to each other.

Primers that are substantially complimentary to a target nucleic acid sequence are also substantially identical to the compliment of the target nucleic acid sequence. That is, primers can be substantially identical to the anti-sense strand of the nucleic acid. As referred to herein, "substantially identical" with respect to sequences refers to nucleotide sequences that are 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more identical to each other. One test for determining whether two nucleotide sequences are substantially identical is to determine the percent of identical nucleotide sequences shared.

Primer sequences and length may affect hybridization to target nucleic acid sequences. Depending on the degree of mismatch between the primer and target nucleic acid, low, medium or high stringency conditions may be used to effect primer/target annealing. As used herein, the term "stringent conditions" refers to conditions for hybridization and washing. Methods for hybridization reaction temperature condition optimization are known to those of skill in the art, and may be found in Current Protocols in Molecular Biology, John Wiley & Sons, N.Y., 6.3.1-6.3.6 (1989). Aqueous and non-aqueous methods are described in that reference and either can be used. Non-limiting examples of stringent hybridization conditions are hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions is hybridization in 6× sodium chloride/sodium citrate (SSC) at about 45° C., followed by one or more washes in 0.2×SSC, 0.1% SDS at 60° C. Often, stringent hybridization conditions are hybridization in 6× sodium chloride/sodium citrate (SSC) at about 45° C., followed by one or more washes in 0.2×SSC, 0.1% SDS at 65° C. More often, stringency conditions are 0.5M sodium phosphate, 7% SDS at 65° C., followed by one or more washes at 0.2×SSC, 1% SDS at 65° C. Stringent hybridization temperatures can also be altered (i.e. lowered) with the addition of certain organic solvents, formamide for example. Organic solvents, like formamide, reduce the thermal stability of double-stranded polynucleotides, so that hybridization can be performed at lower temperatures, while still maintaining stringent conditions and extending the useful life of nucleic acids that may be heat labile.

As used herein, the phrase "hybridizing" or grammatical variations thereof, refers to binding of a first nucleic acid molecule to a second nucleic acid molecule under low, medium or high stringency conditions, or under nucleic acid synthesis conditions. Hybridizing can include instances where a first nucleic acid molecule binds to a second nucleic acid molecule, where the first and second nucleic acid molecules are complementary. As used herein, "specifically hybridizes" refers to preferential hybridization under nucleic acid synthesis conditions of a primer, to a nucleic acid molecule having a sequence complementary to the primer compared to hybridization to a nucleic acid molecule not having a complementary sequence. For example, specific hybridization includes the hybridization of a primer to a target nucleic acid sequence that is complementary to the primer.

In some embodiments primers can include a nucleotide subsequence that may be complementary to a solid phase nucleic acid primer hybridization sequence or substantially complementary to a solid phase nucleic acid primer hybridization sequence (e.g., about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater than 99% identical to the primer hybridization sequence complement when aligned). A primer may contain a nucleotide subsequence not complementary to or not substantially complementary to a solid phase nucleic acid primer hybridization sequence (e.g., at the 3' or 5' end of the nucleotide subsequence in the primer complementary to or substantially complementary to the solid phase primer hybridization sequence).

A primer, in certain embodiments, may contain a detectable molecule or entity (e.g., a fluorophore, radioisotope, colorimetric agent, particle, enzyme and the like). When desired, the nucleic acid can be modified to include a detectable label using any method known to one of skill in the art. The label may be incorporated as part of the synthesis, or added on prior to using the primer in any of the processes described herein. Incorporation of label may be performed either in liquid phase or on solid phase. In some embodiments the detectable label may be useful for detection of targets. In some embodiments the detectable label may be useful for the quantification target nucleic acids (e.g., determining copy number of a particular sequence or species of nucleic acid). Any detectable label suitable for detection of an interaction or biological activity in a system can be appropriately selected and utilized by the artisan. Examples of detectable labels are fluorescent labels such as fluorescein, rhodamine, and others (e.g., Anantha, et al., Biochemistry (1998) 37:2709 2714; and Qu & Chaires, Methods Enzymol. (2000) 321:353 369);

radioactive isotopes (e.g., 125I, 131I, 35S, 31P, 32P, 33P, 14C, 3H, 7Be, 28Mg, 57Co, 65Zn, 67Cu, 68Ge, 82Sr, 83Rb, 95Tc, 96Tc, 103Pd, 109Cd, and 127Xe); light scattering labels (e.g., U.S. Pat. No. 6,214,560, and commercially available from Genicon Sciences Corporation, CA); chemiluminescent labels and enzyme substrates (e.g., dioxetanes and acridinium esters), enzymic or protein labels (e.g., green fluorescence protein (GFP) or color variant thereof, luciferase, peroxidase); other chromogenic labels or dyes (e.g., cyanine), and other cofactors or biomolecules such as digoxigenin, strepdavidin, biotin (e.g., members of a binding pair such as biotin and avidin for example), affinity capture moieties and the like. In some embodiments a primer may be labeled with an affinity capture moiety. Also included in detectable labels are those labels useful for mass modification for detection with mass spectrometry (e.g., matrix-assisted laser desorption ionization (MALDI) mass spectrometry and electrospray (ES) mass spectrometry).

A primer also may refer to a polynucleotide sequence that hybridizes to a subsequence of a target nucleic acid or another primer and facilitates the detection of a primer, a target nucleic acid or both, and amplification products or extension products, as with molecular beacons, for example. The term "molecular beacon" as used herein refers to detectable molecule, where the detectable property of the molecule is detectable only under certain specific conditions, thereby enabling it to function as a specific and informative signal. Non-limiting examples of detectable properties are, optical properties, electrical properties, magnetic properties, chemical properties and time or speed through an opening of known size.

In some embodiments a molecular beacon can be a single-stranded oligonucleotide capable of forming a stem-loop structure, where the loop sequence may be complementary to a target nucleic acid sequence of interest and is flanked by short complementary arms that can form a stem. The oligonucleotide may be labeled at one end with a fluorophore and at the other end with a quencher molecule. In the stem-loop conformation, energy from the excited fluorophore is transferred to the quencher, through long-range dipole-dipole coupling similar to that seen in fluorescence resonance energy transfer, or FRET, and released as heat instead of light. When the loop sequence is hybridized to a specific target sequence, the two ends of the molecule are separated and the energy from the excited fluorophore is emitted as light, generating a detectable signal. Molecular beacons offer the added advantage that removal of excess probe is unnecessary due to the self-quenching nature of the unhybridized probe. In some embodiments molecular beacon probes can be designed to either discriminate or tolerate mismatches between the loop and target sequences by modulating the relative strengths of the loop-target hybridization and stem formation. As referred to herein, the term "mismatched nucleotide" or a "mismatch" refers to a nucleotide that is not complementary to the target sequence at that position or positions. A probe may have at least one mismatch, but can also have 2, 3, 4, 5, 6 or 7 or more mismatched nucleotides.

Detection

Polymorphisms, polynucleotide sequences generated, amplified nucleic acid species (e.g. amplicons or amplification products) or detectable products (e.g., extension products), prepared from the foregoing, can be detected by a suitable detection process. Non limiting examples of methods of detection, quantification, sequencing and the like are; mass detection of mass modified amplicons (e.g., matrix-assisted laser desorption ionization (MALDI) mass spectrometry and electrospray (ES) mass spectrometry), a primer extension method (e.g., iPLEX™; Sequenom, Inc.), microsequencing methods (e.g., a modification of primer extension methodology), ligase sequence determination methods (e.g., U.S. Pat. Nos. 5,679,524 and 5,952,174, and WO 01/27326), mismatch sequence determination methods (e.g., U.S. Pat. Nos. 5,851, 770; 5,958,692; 6,110,684; and 6,183,958), direct DNA sequencing, restriction fragment length polymorphism (RFLP analysis), allele specific oligonucleotide (ASO) analysis, methylation-specific PCR (MSPCR), pyrosequencing analysis, acycloprime analysis, Reverse dot blot, Gene-Chip microarrays, Dynamic allele-specific hybridization (DASH), Peptide nucleic acid (PNA) and locked nucleic acids (LNA) probes, TaqMan, Molecular Beacons, Intercalating dye, FRET primers, AlphaScreen, SNPstream, genetic bit analysis (GBA), Multiplex minisequencing, SNaPshot, GOOD assay, Microarray miniseq, arrayed primer extension (APEX), Microarray primer extension (e.g., microarray sequence determination methods), Tag arrays, Coded microspheres, Template-directed incorporation (TDI), fluorescence polarization, Colorimetric oligonucleotide ligation assay (OLA), Sequence-coded OLA, Microarray ligation, Ligase chain reaction, Padlock probes, Invader assay, hybridization methods (e.g., hybridization using at least one probe, hybridization using at least one fluorescently labeled probe, and the like), conventional dot blot analyses, single strand conformational polymorphism analysis (SSCP, e.g., U.S. Pat. Nos. 5,891,625 and 6,013,499; Orita et al., Proc. Natl. Acad. Sci. U.S.A. 86: 27776-2770 (1989)), denaturing gradient gel electrophoresis (DGGE), heteroduplex analysis, mismatch cleavage detection, and techniques described in Sheffield et al., Proc. Natl. Acad. Sci. USA 49: 699-706 (1991), White et al., Genomics 12: 301-306 (1992), Grompe et al., Proc. Natl. Acad. Sci. USA 86: 5855-5892 (1989), and Grompe, Nature Genetics 5: 111-117 (1993), cloning and sequencing, electrophoresis, the use of hybridization probes and quantitative real time polymerase chain reaction (QRT-PCR), digital PCR, nanopore sequencing, chips and combinations thereof. The detection and quantification of alleles or paralogs can be carried out using the "closed-tube" methods described in U.S. patent application Ser. No. 11/950,395, which was filed Dec. 4, 2007. In some embodiments the amount of each amplified nucleic acid species is determined by mass spectrometry, primer extension, sequencing (e.g., any suitable method, for example nanopore or pyrosequencing), Quantitative PCR (Q-PCR or QRT-PCR), digital PCR, combinations thereof, and the like.

In addition to the methods of detection listed above, the following detection methods may also be used to detect amplified nucleic acid species (e.g., target sequences). In some embodiments, the amplified nucleic acid species, can be sequenced directly using any suitable nucleic acid sequencing method. Non-limiting examples of nucleic acid sequencing methods useful for process described herein are; pyrosequencing, nanopore based sequencing methods (e.g., sequencing by synthesis), sequencing by ligation, sequencing by hybridization, microsequencing (primer extension based polymorphism detection), and conventional nucleotide sequencing (e.g., dideoxy sequencing using conventional methods).

In some embodiments, the amplified sequence(s) may be cloned prior to sequence analysis. That is, the amplified nucleic acid species may be ligated into a nucleic acid cloning vector by any process known to one of skill in the art. Cloning of the amplified nucleic acid species may be performed by including unique restriction sites in primer subsequences, which can be used to generate a fragment flanked by restriction sites useful for cloning into an appropriately prepared vector, in some embodiments. In certain embodiments bluntended cloning can be used to clone amplified nucleic acid species into an appropriately prepared cloning vector. Cloning of the amplified nucleic acid species may be useful for further manipulation, modification, storage, and analysis of the target sequence of interest. In some embodiments, primers may be designed to overlap an SNP site to allow analysis by allele-specific PCR. Allele-specific PCR may be used to discriminate between Y-chromosome loci described herein, because only the correctly hybridized primers will be amplified. In some embodiments, the amplified nucleic acid species may be further analyzed by hybridization (e.g., liquid or solid phase hybridization using sequence specific probes, for example).

Amplified nucleic acids (including amplified nucleic acids that result from reverse transcription) may be modified nucleic acids. Reverse transcribed nucleic acids also may be modified nucleic acids. Modified nucleic acids can include nucleotide analogs, and in certain embodiments include a detectable label and/or a capture agent (e.g., biomolecules or members of a binding pair, as listed below). Modified nucleic acids can be detected by detecting a detectable label or "signal-generating moiety" in some embodiments. The term "signal-generating" as used herein refers to any atom or molecule that can provide a detectable or quantifiable effect, and that can be attached to a nucleic acid. In certain embodiments, a detectable label generates a unique light signal, a fluorescent signal, a luminescent signal, an electrical property, a chemical property, a magnetic property and the like.

Detectable labels include, but are not limited to, nucleotides (labeled or unlabelled), compomers, sugars, peptides, proteins, antibodies, chemical compounds, conducting polymers, binding moieties such as biotin, mass tags, calorimetric agents, light emitting agents, chemiluminescent agents, light scattering agents, fluorescent tags, radioactive tags, charge tags (electrical or magnetic charge), volatile tags and hydrophobic tags, biomolecules (e.g., members of a binding pair antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, vitamin B12/intrinsic factor, chemical reactive group/complementary chemical reactive group (e.g., sulfhydryl/maleimide, sulfhydryl/haloacetyl derivative, amine/isotriocyanate, amine/succinimidyl ester, and amine/sulfonyl halides) and the like, some of which are further described below. In some embodiments a probe may contain a signal-generating moiety that hybridizes to a target and alters the passage of the target nucleic acid through a nanopore, and can generate a signal when released from the target nucleic acid when it passes through the nanopore (e.g., alters the speed or time through a pore of known size).

A solution containing amplicons produced by an amplification process, or a solution containing extension products produced by an extension process, can be subjected to further processing. For example, a solution can be contacted with an agent that removes phosphate moieties from free nucleotides that have not been incorporated into an amplicon or extension product. An example of such an agent is a phosphatase (e.g., alkaline phosphatase). Amplicons and extension products also may be associated with a solid phase, may be washed, may be contacted with an agent that removes a terminal phosphate (e.g., exposure to a phosphatase), may be contacted with an agent that removes a terminal nucleotide (e.g., exonuclease), may be contacted with an agent that cleaves (e.g., endonuclease, ribonuclease), and the like.

The term "solid support" or "solid phase" as used herein refers to an insoluble material with which nucleic acid can be associated. Examples of solid supports for use with processes described herein include, without limitation, arrays, beads (e.g., paramagnetic beads, magnetic beads, microbeads, nanobeads) and particles (e.g., microparticles, nanoparticles). Particles or beads having a nominal, average or mean diameter of about 1 nanometer to about 500 micrometers can be utilized, such as those having a nominal, mean or average diameter, for example, of about 10 nanometers to about 100 micrometers; about 100 nanometers to about 100 micrometers; about 1 micrometer to about 100 micrometers; about 10 micrometers to about 50 micrometers; about 1, 5, 10, 15, 20, 25, 30, 35, 40, 45, 50, 55, 60, 65, 70, 75, 80, 85, 90, 95, 100, 200, 300, 400, 500, 600, 700, 800 or 900 nanometers; or about 1, 5, 10, 15, 20, 25, 30, 35, 40, 45, 50, 55, 60, 65, 70, 75, 80, 85, 90, 95, 100, 200, 300, 400, 500 micrometers.

A solid support can comprise virtually any insoluble or solid material, and often a solid support composition is selected that is insoluble in water. For example, a solid support can comprise or consist essentially of silica gel, glass (e.g. controlled-pore glass (CPG)), nylon, Sephadex®, Sepharose®, cellulose, a metal surface (e.g. steel, gold, silver, aluminum, silicon and copper), a magnetic material, a plastic material (e.g., polyethylene, polypropylene, polyamide, polyester, polyvinylidenedifluoride (PVDF)) and the like. Beads or particles may be swellable (e.g., polymeric beads such as Wang resin) or non-swellable (e.g., CPG). Commercially available examples of beads include without limitation Wang resin, Merrifield resin and Dynabeads® and SoluLink.

A solid support may be provided in a collection of solid supports. A solid support collection comprises two or more different solid support species. The term "solid support species" as used herein refers to a solid support in association with one particular solid phase nucleic acid species or a particular combination of different solid phase nucleic acid species. In certain embodiments, a solid support collection comprises 2 to 10,000 solid support species, 10 to 1,000 solid support species or about 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000 or 10000 unique solid support species. The solid supports (e.g., beads) in the collection of solid supports may be homogeneous (e.g., all are Wang resin beads) or heterogeneous (e.g., some are Wang resin beads and some are magnetic beads). Each solid support species in a collection of solid supports sometimes is labeled with a specific identification tag. An identification tag for a particular solid support species sometimes is a nucleic acid (e.g., "solid phase nucleic acid") having a unique sequence in certain embodiments. An identification tag can be any molecule that is detectable and distinguishable from identification tags on other solid support species.

Mass spectrometry is a particularly effective method for the detection of nucleic acids (e.g., PCR amplicon, primer extension product, detector probe cleaved from a target nucleic acid). Presence of a target nucleic acid is verified by comparing the mass of the detected signal with the expected mass of the target nucleic acid. The relative signal strength, e.g., mass peak on a spectra, for a particular target nucleic acid indicates the relative population of the target nucleic acid amongst other nucleic acids, thus enabling calculation of a ratio of target to other nucleic acid or sequence copy number directly from the data. For a review of genotyping methods using Sequenom® standard iPLEX™ assay and MassARRAY® technology, see Jurinke, C., Oeth, P., van den Boom, D., "MALDI-TOF mass spectrometry: a versatile tool for high-performance DNA analysis." Mol. Biotechnol. 26, 147-164 (2004); and Oeth, P. et al., "iPLEX™ Assay: Increased Plexing Efficiency and Flexibility for MassARRAY® System through single base primer extension with mass-modified Terminators." SEQUENOM Application Note (2005). For a review of detecting and quantifying target nucleic using cleavable detector probes that are cleaved during the amplification process and detected by mass spectrometry, see U.S. patent application Ser. No. 11/950,395, which was filed Dec. 4, 2007, and is hereby incorporated by reference. Such approaches may be adapted to detection of chromosome abnormalities by methods described herein.

In some embodiments, amplified nucleic acid species may be detected by (a) contacting the amplified nucleic acid species (e.g., amplicons) with extension primers (e.g., detection or detector primers), (b) preparing extended extension primers, and (c) determining the relative amount of the one or more mismatch nucleotides (e.g., SNP that exist between SNP-alleles or paralogous sequences) by analyzing the extended detection primers (e.g., extension primers, or detection of extension products). In certain embodiments one or more mismatch nucleotides may be analyzed by mass spectrometry. In some embodiments amplification, using methods described herein, may generate between about 1 to about 100 amplicon sets, about 2 to about 80 amplicon sets, about 4 to about 60 amplicon sets, about 6 to about 40 amplicon sets, and about 8 to about 20 amplicon sets (e.g., about 1, 2, 3, 4, 5, 6, 7, 8, 9, 10, 15, 20, 25, 30, 35, 40, 45, 50, 55, 60, 65, 70, 75, 80, 85, 90, 95, or about 100 amplicon sets).

An example using mass spectrometry for detection of amplicon sets (e.g., sets of amplification products) is presented herein. Amplicons may be contacted (in solution or on solid phase) with a set of oligonucleotides (the same primers used for amplification or different primers representative of subsequences in the primer or target nucleic acid) under hybridization conditions, where: (1) each oligonucleotide in the set comprises a hybridization sequence capable of specifically hybridizing to one amplicon under the hybridization conditions when the amplicon is present in the solution, (2) each oligonucleotide in the set comprises a distinguishable tag located 5' of the hybridization sequence, (3) a feature of the distinguishable tag of one oligonucleotide detectably differs from the features of distinguishable tags of other oligonucleotides in the set; and (4) each distinguishable tag specifically corresponds to a specific amplicon and thereby specifically corresponds to a specific target nucleic acid. The hybridized amplicon and "detection" primer are subjected to nucleotide synthesis conditions that allow extension of the detection primer by one or more nucleotides (labeled with a detectable entity or moiety, or unlabeled), where one of the one of more nucleotides can be a terminating nucleotide. In some embodiments one or more of the nucleotides added to the primer may comprises a capture agent. In embodiments where hybridization occurred in solution, capture of the primer/amplicon to solid support may be desirable. The detectable moieties or entities can be released from the extended detection primer, and detection of the moiety determines the presence, absence or copy number of the nucleotide sequence of interest. In certain embodiments, the extension may be performed once yielding one extended oligonucleotide. In some embodiments, the extension may be performed multiple times (e.g., under amplification conditions) yielding multiple copies of the extended oligonucleotide. In some embodiments performing the extension multiple times can produce a sufficient number of copies such that interpretation of signals, representing copy number of a particular sequence, can be made with a confidence level of 95% or more (e.g., confidence level of 95% or more, 96% or more, 97% or more, 98% or more, 99% or more, or a confidence level of 99.5% or more). In some embodiments, the method for detecting amplicon sets can be used to detect extension products.

Methods provided herein allow for high-throughput detection of nucleic acid species in a plurality of nucleic acids (e.g., nucleotide sequence species, amplified nucleic acid species and detectable products generated from the foregoing). Multiplexing refers to the simultaneous detection of more than one nucleic acid species. General methods for performing multiplexed reactions in conjunction with mass spectrometry, are known (see, e.g., U.S. Pat. Nos. 6,043,031, 5,547,835 and International PCT application No. WO 97/37041). Multiplexing provides an advantage that a plurality of nucleic acid species (e.g., some having different sequence variations) can be identified in as few as a single mass spectrum, as compared to having to perform a separate mass spectrometry analysis for each individual target nucleic acid species. Methods provided herein lend themselves to high-throughput, highly-automated processes for analyzing sequence variations with high speed and accuracy, in some embodiments. In some embodiments, methods herein may be multiplexed at high levels in a single reaction.

Microarrays may be adapted for use in embodiments described herein. A microarray can be utilized for determining whether a polymorphic variant is present or absent in a nucleic acid sample. A microarray may include any oligonucleotides or primers described herein, and methods for making and using oligonucleotide microarrays suitable for prognostic use are disclosed in U.S. Pat. Nos. 5,492,806; 5,525,464; 5,589,330; 5,695,940; 5,849,483; 6,018,041; 6,045,996; 6,136,541; 6,142,681; 6,156,501; 6,197,506; 6,223,127; 6,225,625; 6,229,911; 6,239,273; WO 00/52625; WO 01/25485; and WO 01/29259. The microarray typically comprises a solid support and the oligonucleotides may be linked to this solid support by covalent bonds or by non-covalent interactions. The oligonucleotides may also be linked to the solid support directly or by a spacer molecule. A microarray may comprise one or more oligonucleotides complementary to a polymorphic site within a nucleotide sequence in Tables 6, 7 or 8. Microarrays may be used with multiplexed protocols described herein.

In certain embodiments, the number of nucleic acid species multiplexed include, without limitation, about 1 to about 500 (e.g., about 1-3, 3-5, 5-7, 7-9, 9-11, 11-13, 13-15, 15-17, 17-19, 19-21, 21-23, 23-25, 25-27, 27-29, 29-31, 31-33, 33-35, 35-37, 37-39, 39-41, 41-43, 43-45, 45-47, 47-49, 49-51, 51-53, 53-55, 55-57, 57-59, 59-61, 61-63, 63-65, 65-67, 67-69, 69-71, 71-73, 73-75, 75-77, 77-79, 79-81, 81-83, 83-85, 85-87, 87-89, 89-91, 91-93, 93-95, 95-97, 97-101, 101-103, 103-105, 105-107, 107-109, 109-111, 111-113, 113-115, 115-117, 117-119, 121-123, 123-125, 125-127, 127-129, 129-131, 131-133, 133-135, 135-137, 137-139, 139-141, 141-143, 143-145, 145-147, 147-149, 149-151, 151-153, 153-155, 155-157, 157-159, 159-161, 161-163, 163-165, 165-167, 167-169, 169-171, 171-173, 173-175, 175-177, 177-179, 179-181, 181-183, 183-185, 185-187, 187-189, 189-191, 191-193, 193-195, 195-197, 197-199, 199-201, 201-203, 203-205, 205-207, 207-209, 209-211, 211-213, 213-215, 215-217, 217-219, 219-221, 221-223, 223-225, 225-227, 227-229, 229-231, 231-233, 233-235, 235-237, 237-239, 239-241, 241-243, 243-245, 245-247, 247-249, 249-251, 251-253, 253-255, 255-257, 257-259, 259-261, 261-263, 263-265, 265-267, 267-269, 269-271, 271-273, 273-275, 275-277, 277-279, 279-281, 281-283, 283-285, 285-287, 287-289, 289-291, 291-293, 293-295, 295-297, 297-299, 299-301, 301-303, 303-305, 305-307, 307-309, 309-311, 311-313, 313-315, 315-317, 317-

319, 319-321, 321-323, 323-325, 325-327, 327-329, 329-331, 331-333, 333-335, 335-337, 337-339, 339-341, 341-343, 343-345, 345-347, 347-349, 349-351, 351-353, 353-355, 355-357, 357-359, 359-361, 361-363, 363-365, 365-367, 367-369, 369-371, 371-373, 373-375, 375-377, 377-379, 379-381, 381-383, 383-385, 385-387, 387-389, 389-391, 391-393, 393-395, 395-397, 397-401, 401-403, 403-405, 405-407, 407-409, 409-411, 411-413, 413-415, 415-417, 417-419, 419-421, 421-423, 423-425, 425-427, 427-429, 429-431, 431-433, 433-435, 435-437, 437-439, 439-441, 441-443, 443-445, 445-447, 447-449, 449-451, 451-453, 453-455, 455-457, 457-459, 459-461, 461-463, 463-465, 465-467, 467-469, 469-471, 471-473, 473-475, 475-477, 477-479, 479-481, 481-483, 483-485, 485-487, 487-489, 489-491, 491-493, 493-495, 495-497, 497-501).

Design methods for achieving resolved mass spectra with multiplexed assays can include primer and oligonucleotide design methods and reaction design methods. For primer and oligonucleotide design in multiplexed assays, the same general guidelines for primer design applies for uniplexed reactions, such as avoiding false priming and primer dimers, only more primers are involved for multiplex reactions. For mass spectrometry applications, analyte peaks in the mass spectra for one assay are sufficiently resolved from a product of any assay with which that assay is multiplexed, including pausing peaks and any other by-product peaks. Also, analyte peaks optimally fall within a user-specified mass window, for example, within a range of 5,000-8,500 Da. In some embodiments multiplex analysis may be adapted to mass spectrometric detection of chromosome abnormalities, for example. In certain embodiments multiplex analysis may be adapted to various single nucleotide or nanopore based sequencing methods described herein. Commercially produced microreaction chambers or devices or arrays or chips may be used to facilitate multiplex analysis, and are commercially available.

Nucleotide sequence species, amplified nucleic acid species, or detectable products generated from the foregoing may be subject to sequence analysis. The term "sequence analysis" as used herein refers to determining a nucleotide sequence of an amplification product. The entire sequence or a partial sequence of an amplification product can be determined, and the determined nucleotide sequence is referred to herein as a "read." For example, linear amplification products may be analyzed directly without further amplification in some embodiments (e.g., by using single-molecule sequencing methodology (described in greater detail hereafter)). In certain embodiments, linear amplification products may be subject to further amplification and then analyzed (e.g., using sequencing by ligation or pyrosequencing methodology (described in greater detail hereafter)). Reads may be subject to different types of sequence analysis. Any suitable sequencing method can be utilized to detect, and determine the amount of, nucleotide sequence species, amplified nucleic acid species, or detectable products generated from the foregoing. Examples of certain sequencing methods are described hereafter.

The terms "sequence analysis apparatus" and "sequence analysis component(s)" used herein refer to apparatus, and one or more components used in conjunction with such apparatus, that can be used by a person of ordinary skill to determine a nucleotide sequence from amplification products resulting from processes described herein (e.g., linear and/or exponential amplification products). Examples of sequencing platforms include, without limitation, the 454 platform (Roche) (Margulies, M. et al. 2005 Nature 437, 376-380), Illumina Genomic Analyzer (or Solexa platform) or SOLID System (Applied Biosystems) or the Helicos True Single Molecule DNA sequencing technology (Harris T D et al. 2008 Science, 320, 106-109), the single molecule, real-time (SMRT™) technology of Pacific Biosciences, and nanopore sequencing (Soni G V and Meller A. 2007 Clin Chem 53: 1996-2001). Such platforms allow sequencing of many nucleic acid molecules isolated from a specimen at high orders of multiplexing in a parallel manner (Dear Brief Funct Genomic Proteomic 2003; 1: 397-416). Each of these platforms allows sequencing of clonally expanded or non-amplified single molecules of nucleic acid fragments. Certain platforms involve, for example, (i) sequencing by ligation of dye-modified probes (including cyclic ligation and cleavage), (ii) pyrosequencing, and (iii) single-molecule sequencing. Nucleotide sequence species, amplification nucleic acid species and detectable products generated there from can be considered a "study nucleic acid" for purposes of analyzing a nucleotide sequence by such sequence analysis platforms.

Sequencing by ligation is a nucleic acid sequencing method that relies on the sensitivity of DNA ligase to base-pairing mismatch. DNA ligase joins together ends of DNA that are correctly base paired. Combining the ability of DNA ligase to join together only correctly base paired DNA ends, with mixed pools of fluorescently labeled oligonucleotides or primers, enables sequence determination by fluorescence detection. Longer sequence reads may be obtained by including primers containing cleavable linkages that can be cleaved after label identification. Cleavage at the linker removes the label and regenerates the 5' phosphate on the end of the ligated primer, preparing the primer for another round of ligation. In some embodiments primers may be labeled with more than one fluorescent label (e.g., 1 fluorescent label, 2, 3, or 4 fluorescent labels).

An example of a system that can be used by a person of ordinary skill based on sequencing by ligation generally involves the following steps. Clonal bead populations can be prepared in emulsion microreactors containing target nucleic acid sequences ("template"), amplification reaction components, beads and primers. After amplification, templates are denatured and bead enrichment is performed to separate beads with extended templates from undesired beads (e.g., beads with no extended templates). The template on the selected beads undergoes a 3' modification to allow covalent bonding to the slide, and modified beads can be deposited onto a glass slide. Deposition chambers offer the ability to segment a slide into one, four or eight chambers during the bead loading process. For sequence analysis, primers hybridize to the adapter sequence. A set of four color dye-labeled probes competes for ligation to the sequencing primer. Specificity of probe ligation is achieved by interrogating every 4th and 5th base during the ligation series. Five to seven rounds of ligation, detection and cleavage record the color at every 5th position with the number of rounds determined by the type of library used. Following each round of ligation, a new complimentary primer offset by one base in the 5' direction is laid down for another series of ligations. Primer reset and ligation rounds (5-7 ligation cycles per round) are repeated sequentially five times to generate 25-35 base pairs of sequence for a single tag. With mate-paired sequencing, this process is repeated for a second tag. Such a system can be used to exponentially amplify amplification products generated by a process described herein, e.g., by ligating a heterologous nucleic acid to the first amplification product generated by a process described herein and performing emulsion amplification using the same or a different solid support originally used to generate the first amplification product. Such a system also may be used to analyze amplification products directly generated by a process described herein by bypassing an exponential amplification process and directly sorting the solid supports described herein on the glass slide.

Pyrosequencing is a nucleic acid sequencing method based on sequencing by synthesis, which relies on detection of a pyrophosphate released on nucleotide incorporation. Generally, sequencing by synthesis involves synthesizing, one nucleotide at a time, a DNA strand complimentary to the strand whose sequence is being sought. Target nucleic acids may be immobilized to a solid support, hybridized with a sequencing primer, incubated with DNA polymerase, ATP sulfurylase, luciferase, apyrase, adenosine 5' phosphsulfate and luciferin. Nucleotide solutions are sequentially added and removed. Correct incorporation of a nucleotide releases a pyrophosphate, which interacts with ATP sulfurylase and produces ATP in the presence of adenosine 5' phosphsulfate, fueling the luciferin reaction, which produces a chemiluminescent signal allowing sequence determination. The amount of light generated is proportional to the number of bases added. Accordingly, the sequence downstream of the sequencing primer can be determined.

An example of a system that can be used by a person of ordinary skill based on pyrosequencing generally involves the following steps: ligating an adaptor nucleic acid to a study nucleic acid and hybridizing the study nucleic acid to a bead; amplifying a nucleotide sequence in the study nucleic acid in an emulsion; sorting beads using a picoliter multiwell solid support; and sequencing amplified nucleotide sequences by pyrosequencing methodology (e.g., Nakano et al., "Single-molecule PCR using water-in-oil emulsion;" Journal of Biotechnology 102: 117-124 (2003)). Such a system can be used to exponentially amplify amplification products generated by a process described herein, e.g., by ligating a heterologous nucleic acid to the first amplification product generated by a process described herein.

Certain single-molecule sequencing embodiments are based on the principal of sequencing by synthesis, and utilize single-pair Fluorescence Resonance Energy Transfer (single pair FRET) as a mechanism by which photons are emitted as a result of successful nucleotide incorporation. The emitted photons often are detected using intensified or high sensitivity cooled charge-couple-devices in conjunction with total internal reflection microscopy (TIRM). Photons are only emitted when the introduced reaction solution contains the correct nucleotide for incorporation into the growing nucleic acid chain that is synthesized as a result of the sequencing process. In FRET based single-molecule sequencing, energy is transferred between two fluorescent dyes, sometimes polymethine cyanine dyes Cy3 and Cy5, through long-range dipole interactions. The donor is excited at its specific excitation wavelength and the excited state energy is transferred, non-radiatively to the acceptor dye, which in turn becomes excited. The acceptor dye eventually returns to the ground state by radiative emission of a photon. The two dyes used in the energy transfer process represent the "single pair", in single pair FRET. Cy3 often is used as the donor fluorophore and often is incorporated as the first labeled nucleotide. Cy5 often is used as the acceptor fluorophore and is used as the nucleotide label for successive nucleotide additions after incorporation of a first Cy3 labeled nucleotide. The fluorophores generally are within 10 nanometers of each for energy transfer to occur successfully.

An example of a system that can be used based on single-molecule sequencing generally involves hybridizing a primer to a target nucleic acid sequence to generate a complex; associating the complex with a solid phase; iteratively extending the primer by a nucleotide tagged with a fluorescent molecule; and capturing an image of fluorescence resonance energy transfer signals after each iteration (e.g., U.S. Pat. No. 7,169,314; Braslavsky et al., PNAS 100(7): 3960-3964 (2003)). Such a system can be used to directly sequence amplification products (linearly or exponentially amplified products) generated by processes described herein. In some embodiments the amplification products can be hybridized to a primer that contains sequences complementary to immobilized capture sequences present on a solid support, a bead or glass slide for example. Hybridization of the primer-amplification product complexes with the immobilized capture sequences, immobilizes amplification products to solid supports for single pair FRET based sequencing by synthesis. The primer often is fluorescent, so that an initial reference image of the surface of the slide with immobilized nucleic acids can be generated. The initial reference image is useful for determining locations at which true nucleotide incorporation is occurring. Fluorescence signals detected in array locations not initially identified in the "primer only" reference image are discarded as non-specific fluorescence. Following immobilization of the primer-amplification product complexes, the bound nucleic acids often are sequenced in parallel by the iterative steps of, a) polymerase extension in the presence of one fluorescently labeled nucleotide, b) detection of fluorescence using appropriate microscopy, TIRM for example, c) removal of fluorescent nucleotide, and d) return to step a with a different fluorescently labeled nucleotide.

In some embodiments, nucleotide sequencing may be by solid phase single nucleotide sequencing methods and processes. Solid phase single nucleotide sequencing methods involve contacting target nucleic acid and solid support under conditions in which a single molecule of sample nucleic acid hybridizes to a single molecule of a solid support. Such conditions can include providing the solid support molecules and a single molecule of target nucleic acid in a "microreactor." Such conditions also can include providing a mixture in which the target nucleic acid molecule can hybridize to solid phase nucleic acid on the solid support. Single nucleotide sequencing methods useful in the embodiments described herein are described in U.S. Provisional Patent Application Ser. No. 61/021,871 filed Jan. 17, 2008.

In certain embodiments, nanopore sequencing detection methods include (a) contacting a target nucleic acid for sequencing ("base nucleic acid," e.g., linked probe molecule) with sequence-specific detectors, under conditions in which the detectors specifically hybridize to substantially complementary subsequences of the base nucleic acid; (b) detecting signals from the detectors and (c) determining the sequence of the base nucleic acid according to the signals detected. In certain embodiments, the detectors hybridized to the base nucleic acid are disassociated from the base nucleic acid (e.g., sequentially dissociated) when the detectors interfere with a nanopore structure as the base nucleic acid passes through a pore, and the detectors disassociated from the base sequence are detected. In some embodiments, a detector disassociated from a base nucleic acid emits a detectable signal, and the detector hybridized to the base nucleic acid emits a different detectable signal or no detectable signal. In certain embodiments, nucleotides in a nucleic acid (e.g., linked probe molecule) are substituted with specific nucleotide sequences corresponding to specific nucleotides ("nucleotide representatives"), thereby giving rise to an expanded nucleic acid (e.g., U.S. Pat. No. 6,723,513), and the detectors hybridize to the nucleotide representatives in the expanded nucleic acid, which serves as a base nucleic acid. In such embodiments, nucleotide representatives may be arranged in a binary or higher order arrangement (e.g., Soni and Meller, Clinical Chemistry 53(11): 1996-2001 (2007)). In some embodiments, a nucleic acid is not expanded, does not give rise to an expanded nucleic acid, and directly serves a base nucleic acid (e.g., a linked probe molecule serves as a non-expanded base nucleic acid), and detectors are directly contacted with the base nucleic acid. For example, a first detector may hybridize to a first subsequence and a second detector may hybridize to a second subsequence, where the first detector and second detector each have detectable labels that can be distinguished from one another, and where the signals from the first detector and second detector can be distinguished from one another when the detectors are disassociated from the base nucleic acid. In certain embodiments, detectors include a region that hybridizes to the base nucleic acid (e.g., two regions), which can be about 3 to about 100 nucleotides in length (e.g., about 4, 5, 6, 7, 8, 9, 10, 11, 12, 13, 14, 15, 16, 17, 18, 19, 20, 25, 30, 35, 40, 50, 55, 60, 65, 70, 75, 80, 85, 90, or 95 nucleotides in length). A detector also may include one or more regions of nucleotides that do not hybridize to the base nucleic acid. In some embodiments, a detector is a molecular beacon. A detector often comprises one or more detectable labels independently selected from those described herein. Each detectable label can be detected by any convenient detection process capable of detecting a signal generated by each label (e.g., magnetic, electric, chemical, optical and the like). For example, a CD camera can be used to detect signals from one or more distinguishable quantum dots linked to a detector.

In certain sequence analysis embodiments, reads may be used to construct a larger nucleotide sequence, which can be facilitated by identifying overlapping sequences in different reads and by using identification sequences in the reads. Such sequence analysis methods and software for constructing larger sequences from reads are known to the person of ordinary skill (e.g., Venter et al., Science 291: 1304-1351 (2001)). Specific reads, partial nucleotide sequence constructs, and full nucleotide sequence constructs may be compared between nucleotide sequences within a sample nucleic acid (i.e., internal comparison) or may be compared with a reference sequence (i.e., reference comparison) in certain sequence analysis embodiments. Internal comparisons sometimes are performed in situations where a sample nucleic acid is prepared from multiple samples or from a single sample source that contains sequence variations. Reference comparisons sometimes are performed when a reference nucleotide sequence is known and an objective is to determine whether a sample nucleic acid contains a nucleotide sequence that is substantially similar or the same, or different, than a reference nucleotide sequence. Sequence analysis can be facilitated by the use of sequence analysis apparatus and components described above.

Y-chromosome loci described herein can also be detected using standard electrophoretic techniques. Although the detection step can sometimes be preceded by an amplification step, amplification is not required in the embodiments described herein. Examples of methods for detection and quantification of the Y-chromosome loci described herein using electrophoretic techniques can be found in the art. A non-limiting example is presented herein. After running a sample (e.g., mixed nucleic acid sample isolated from maternal serum, or amplification nucleic acid species, for example) in an agarose or polyacrylamide gel, the gel may be labeled (e.g., stained) with ethidium bromide (see, Sambrook and Russell, Molecular Cloning: A Laboratory Manual 3d ed., 2001). The presence of a band of the same size as the standard control is an indication of the presence of a target nucleic acid sequence, the amount of which may then be compared to the control based on the intensity of the band, thus detecting and quantifying the target sequence of interest. In some embodiments, restriction enzymes capable of distinguishing between maternal and paternal alleles may be used to detect and quantify target nucleic acid species. In certain embodiments, oligonucleotide probes specific to Y-chromosome loci described herein (see Table 1) can be used to detect the presence of the target sequence of interest. The oligonucleotides can also be used to indicate the amount of the target nucleic acid molecules in comparison to the standard control, based on the intensity of signal imparted by the probe.

Sequence-specific probe hybridization can be used to detect a particular nucleic acid in a mixture or mixed population comprising other species of nucleic acids. Under sufficiently stringent hybridization conditions, the probes hybridize specifically only to substantially complementary sequences. The stringency of the hybridization conditions can be relaxed to tolerate varying amounts of sequence mismatch. A number of hybridization formats are known in the art, which include but are not limited to, solution phase, solid phase, or mixed phase hybridization assays. The following articles provide an overview of the various hybridization assay formats: Singer et al., Biotechniques 4:230, 1986; Haase et al., Methods in Virology, pp. 189-226, 1984; Wilkinson, In situ Hybridization, Wilkinson ed., IRL Press, Oxford University Press, Oxford; and Hames and Higgins eds., Nucleic Acid Hybridization: A Practical Approach, IRL Press, 1987.

Hybridization complexes can be detected by techniques known in the art. Nucleic acid probes capable of specifically hybridizing to a target nucleic acid (e.g., the mRNA or the amplified DNA) can be labeled by any suitable method, and the labeled probe used to detect the presence of hybridized nucleic acids. One commonly used method of detection is autoradiography, using probes labeled with $^{3}H$, $^{125}I$, $^{35}S$, $^{14}C$, $^{32}P$, $^{33}P$, or the like. The choice of radioactive isotope depends on research preferences due to ease of synthesis, stability, and half-lives of the selected isotopes. Other labels include compounds (e.g., biotin and digoxigenin), which bind to antiligands or antibodies labeled with fluorophores, chemiluminescent agents, and enzymes. In some embodiments, probes can be conjugated directly with labels such as fluorophores, chemiluminescent agents or enzymes. The choice of label depends on sensitivity required, ease of conjugation with the probe, stability requirements, and available instrumentation.

Primer extension polymorphism detection methods, also referred to herein as "microsequencing" methods, typically are carried out by hybridizing a complementary oligonucleotide to a nucleic acid carrying the polymorphic site. In these methods, the oligonucleotide typically hybridizes adjacent to the polymorphic site. The term "adjacent" as used in reference to "microsequencing" methods, refers to the 3' end of the extension oligonucleotide being sometimes 1 nucleotide from the 5' end of the polymorphic site, often 2 or 3, and at times 4, 5, 6, 7, 8, 9, or 10 nucleotides from the 5' end of the polymorphic site, in the nucleic acid when the extension oligonucleotide is hybridized to the nucleic acid. The extension oligonucleotide then is extended by one or more nucleotides, often 1, 2, or 3 nucleotides, and the number and/or type of nucleotides that are added to the extension oligonucleotide determine which polymorphic variant or variants are present. Oligonucleotide extension methods are disclosed, for example, in U.S. Pat. Nos. 4,656,127; 4,851,331; 5,679,524; 5,834,189; 5,876,934; 5,908,755; 5,912,118; 5,976,802; 5,981,186; 6,004,744; 6,013,431; 6,017,702; 6,046,005; 6,087,095; 6,210,891; and WO 01/20039. The extension products can be detected in any manner, such as by fluorescence methods (see, e.g., Chen & Kwok, Nucleic Acids Research 25: 347-353 (1997) and Chen et al., Proc. Natl. Acad. Sci. USA 94/20: 10756-10761 (1997)) or by mass spectrometric methods (e.g., MALDI-TOF mass spectrometry) and other methods described herein. Oligonucleotide extension methods using mass spectrometry are described, for example, in U.S. Pat. Nos. 5,547,835; 5,605,798; 5,691, 141; 5,849,542; 5,869,242; 5,928,906; 6,043,031; 6,194,144; and 6,258,538.

Microsequencing detection methods often incorporate an amplification process that proceeds the extension step. The amplification process typically amplifies a region from a nucleic acid sample that comprises the polymorphic site. Amplification can be carried out utilizing methods described above, or for example using a pair of oligonucleotide primers in a polymerase chain reaction (PCR), in which one oligonucleotide primer typically is complementary to a region 3' of the polymorphism and the other typically is complementary to a region 5' of the polymorphism. A PCR primer pair may be used in methods disclosed in U.S. Pat. Nos. 4,683,195; 4,683, 202, 4,965,188; 5,656,493; 5,998,143; 6,140,054; WO 01/27327; and WO 01/27329 for example. PCR primer pairs may also be used in any commercially available machines that perform PCR, such as any of the GeneAmp® Systems available from Applied Biosystems.

Whole genome sequencing may also be utilized for discriminating alleles of RNA transcripts, in some embodiments. Examples of whole genome sequencing methods include, but are not limited to, nanopore-based sequencing methods, sequencing by synthesis and sequencing by ligation, as described above.

Rhd Assay

Methods and compositions described herein may be combined with other assays to determine fetal blood type and/or blood compatibility. For example, the present invention may be combined with nucleic acid-based assays that are useful for RhD typing. More specifically, RhD typing may include compositions and methods for determining the presence or absence of any one of exon 4, exon 5, exon 7 or exon 10 in the RhD gene, or the presence or absence of the RhD pseudogene ψ (psi).

Fetal Identifiers

Cell-free fetal DNA constitutes only a minor fraction of the total DNA found in maternal plasma. The amount of fetal DNA in maternal plasma is dependent on the gestational age and is estimated at 3-6% in certain embodiments, and sometimes is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35% of extracellular nucleic acid in a sample. Therefore, it sometimes is helpful to ascertain that the diagnostic result is true and not caused by insufficient amount of circulating fetal DNA or loss of the fetal DNA during sample processing.

The use of polymorphisms provide a means to confirm the presence of fetal DNA and therefore complete the analysis of negative, and otherwise inconclusive, test result in non-invasive prenatal diagnostics. The use of single nucleotide polymorphisms (SNPs), the most abundant type of polymorphism in the human genome, or insertion/deletion (Ins/Del) polymorphisms may serve as fetal identifiers to determine the presence of fetal DNA in a processed sample (Li, Y., Wenzel, F., Holzgreve, W., Hahn, S., Genotyping fetal paternally inherited SNPs by MALDI-TOF MS using cell-free fetal DNA in maternal plasma: Influence of size fractionation. Electrophoresis 27, 3889-3896 (2006); Van der Schoot, C. E., Rijnders, R. J., Bossers, B., de Haas, M., Christiaens, G. C., Dee, R. Real-time PCR of bi-allelic insertion/deletion polymorphisms can serve as a reliable positive control for cell-free fetal DNA in non-invasive prenatal genotyping [abstract] Blood 102, 93a (2003); and Chow, K. C., Chiu, R. W., Tsui, N. B., Ding, C., Lau, T. K., Leung, T. N., Lo, Y. M., Mass Spectrometric detection of a SNP panel as an internal positive control for fetal DNA analysis in maternal plasma. Clin. Chem. 53, 141-142 (2007), all of which are hereby incorporated by reference).

A SNP is considered informative for the determination of the presence of fetal DNA, if the mother is homozygous and the fetus inherited the opposite allele from the father, rendering the genotype of the fetus heterozygous.

To ensure a high probability that the presence of fetal DNA can be confirmed by the presence of the paternally-inherited allele in at least 1 SNP, a sufficient number of SNPs or Ins/Dels with a high population frequency (>0.4 for the minor frequent allele) has to be analyzed. A scheme exemplifying the concept of using SNPs to confirm the presence of fetal DNA in maternal plasma is depicted in FIG. 5.

Analysis of multiple polymorphisms in DNA extracted from maternal plasma creates a two-fold challenge: firstly, the paternally-inherited allele needs to be detected in the background of the maternal DNA; secondly, the high number of polymorphisms require significant sample material and a significant number of reactions before a conclusive test result is achieved.

Data Processing

The term "detection" or "detecting" or "identifying" Y-chromosome nucleic acid or the sex of a fetus as used herein refers to identification of the presence or absence of Y-chromosome nucleic acid by processing data arising from detecting one or more sets of amplified nucleic acid species, nucleotide sequence species, or a detectable product generated from the foregoing (collectively "detectable product"). Any suitable detection device and method can be used to distinguish one or more sets of detectable products, as addressed herein. An outcome pertaining to the presence or absence of Y-chromosome nucleic acid can be expressed in any suitable form, including, without limitation, ratio, deviation in ratio, frequency, distribution, probability (e.g., odds ratio, p-value), likelihood, percentage, value over a threshold, or risk factor, associated with the presence of Y-chromosome nucleic acid for a subject or sample. An outcome may be provided with one or more of sensitivity, specificity, standard deviation, coefficient of variation (CV) and/or confidence level, or combinations of the foregoing, in certain embodiments.

An outcome pertaining to presence or absence of Y-chromosome nucleic acid may be determined for all samples tested, and in some embodiments, an outcome pertaining to presence or absence of Y-chromosome nucleic acid is determined in a subset of the samples (e.g., samples from individual pregnant females). In certain embodiments, an outcome is determined for about 60, 65, 70, 75, 76, 77, 78, 79, 80, 81, 82, 83, 84, 85, 86, 87, 88, 89, 90, 91, 92, 93, 94, 95, 96, 97, 98, 99%, or greater than 99%, of samples analyzed in a set. A set of samples can include any suitable number of samples, and in some embodiments, a set has about 10, 15, 20, 25, 30, 35, 40, 45, 50, 55, 60, 65, 70, 75, 80, 90, 100, 200, 300, 400, 500, 600, 700, 800, 900 or 1000 samples, or more than 1000 samples. The set may be considered with respect to samples tested in a particular period of time, and/or at a particular location. The set may be otherwise defined by, for example, gestational age and/or ethnicity. The set may be comprised of a sample which is subdivided into subsamples or replicates all or some of which may be tested. The set may comprise a sample from the same subject collected at two different times. In certain embodiments, an outcome is determined about 60% or more of the time for a given sample analyzed (e.g., about 65, 70, 75, 76, 77, 78, 79, 80, 81, 82, 83, 84, 85, 86, 87, 88, 89, 90, 91, 92, 93, 94, 95, 96, 97, 98, 99%, or more than 99% of the time for a given sample). In certain embodiments, analyzing a higher number of characteristics (e.g., sequence variations) that discriminate alleles can increase the percentage of outcomes determined for the samples (e.g., discriminated in a multiplex analysis). In some embodiments, one or more tissue or fluid samples (e.g., one or more blood samples) are provided by a subject (e.g., pregnant female). In certain embodiments, one or more nucleic acid samples, or two or more replicate nucleic acid samples, are isolated from a single tissue or fluid sample, and analyzed by methods described herein.

In certain multiplex embodiments for determining the sex of a fetus, the presence of a male fetus is the outcome called where a detectable amount of amplification product for 100% of all Y-chromosome targets assayed in the multiplex assay is detected. In some embodiments, the presence of a male fetus is the outcome called where a detectable amount of amplification product for about 90% to about 99% (e.g., about 90, 91, 92, 93, 94, 95, 96, 97, 98, 99 or more than 99%) of all Y-chromosome targets assayed is detected. In some embodiments, the presence of a male fetus is the outcome called where a detectable amount of amplification product for all but one, or all but two, of all Y-chromosome targets assayed is detected. In certain embodiments, the presence of a female fetus is the outcome called where a detectable amount of amplification product for none of the Y-chromosome targets assayed is detected. In some embodiments, the presence of a female fetus is the outcome called where a detectable amount of amplification product for about 1% to about 25% (e.g., less than about 1%, or about 1, 2, 3, 4, 5, 6, 7, 8, 9, 10, 11, 12, 13, 14, 15, 16, 17, 18, 19, 20, 21, 22, 23, 24 or 25%) of all Y-chromosome targets assayed is detected. In some embodiments, the presence of a female fetus is the outcome called where a detectable amount of amplification product for only one, or only two, of all Y-chromosome targets assayed is detected.

Detection of presence or absence of Y-chromosome nucleic acid based on one or more sets of detectable products may be identified based on one or more calculated variables, including, but not limited to, ratio, distribution, frequency, sensitivity, specificity, standard deviation, coefficient of variation (CV), a threshold, confidence level, score, probability and/or a combination thereof. In some embodiments, (i) the number of sets selected for a diagnostic method, and/or (ii) the particular nucleotide sequence species of each set selected for a diagnostic method, is determined in part or in full according to one or more of such calculated variables.

In certain embodiments, one or more of ratio, sensitivity, specificity and/or confidence level are expressed as a percentage. In some embodiments, the percentage, independently for each variable, is greater than about 90% (e.g., about 90, 91, 92, 93, 94, 95, 96, 97, 98 or 99%, or greater than 99% (e.g., about 99.5%, or greater, about 99.9% or greater, about 99.95% or greater, about 99.99% or greater)). Coefficient of variation (CV) in some embodiments is expressed as a percentage, and sometimes the percentage is about 10% or less (e.g., about 10, 9, 8, 7, 6, 5, 4, 3, 2 or 1%, or less than 1% (e.g., about 0.5% or less, about 0.1% or less, about 0.05% or less, about 0.01% or less)). A probability (e.g., that a particular outcome determined by an algorithm is not due to chance) in certain embodiments is expressed as a p-value, and sometimes the p-value is about 0.05 or less (e.g., about 0.05, 0.04, 0.03, 0.02 or 0.01, or less than 0.01 (e.g., about 0.001 or less, about 0.0001 or less, about 0.00001 or less, about 0.000001 or less)).

For example, scoring or a score may refer to calculating the probability that Y-chromosome nucleic acid is present or absent in a subject/sample. The value of a score may be used to determine for example the variation, difference, or ratio of amplified nucleic detectable product that may correspond to the actual presence or absence of Y-chromosome nucleic acid. For example, calculating a positive score from detectable products can lead to an identification of presence or absence of Y-chromosome nucleic acid, which is particularly relevant to analysis of single samples.

In certain embodiments, simulated (or simulation) data can aid data processing for example by training an algorithm or testing an algorithm. Simulated data may for instance involve hypothetical various samples of different concentrations of fetal and maternal nucleic acid in serum, plasma and the like. Simulated data may be based on what might be expected from a real population or may be skewed to test an algorithm and/or to assign a correct classification based on a simulated data set. Simulated data also is referred to herein as "virtual" data. Fetal/maternal contributions within a sample can be simulated as a table or array of numbers (for example, as a list of peaks corresponding to the mass signals of cleavage products of a reference biomolecule or amplified nucleic acid sequence), as a mass spectrum, as a pattern of bands on a gel, label intensity, or as a representation of any technique that measures mass distribution. Simulations can be performed in most instances by a computer program. One possible step in using a simulated data set is to evaluate the confidence of the identified results, i.e. how well the selected positives/negatives match the sample and whether there are additional variations. A common approach is to calculate the probability value (p-value) which estimates the probability of a random sample having better score than the selected one. As p-value calculations can be prohibitive in certain circumstances, an empirical model may be assessed, in which it is assumed that at least one sample matches a reference sample (with or without resolved variations). Other distributions such as Poisson distribution can be used to describe the probability distribution.

In certain embodiments, an algorithm can assign a confidence value to the true positives, true negatives, false positives and false negatives calculated. The assignment of a likelihood of the occurrence of Y-chromosome nucleic acid can also be based on a certain probability model.

Simulated data often is generated in an in silico process. As used herein, the term "in silico" refers to research and experiments performed using a computer. In silico methods include, but are not limited to, molecular modeling studies, karyotyping, genetic calculations, and virtual representations of molecular structures and/or processes, such as genetic information.

As used herein, a "data processing routine" refers to a process, that can be embodied in software, that determines the biological significance of acquired data (i.e., the ultimate results of an assay). For example, a data processing routine can determine the amount of each nucleotide sequence species based upon the data collected. A data processing routine also may control an instrument and/or a data collection routine based upon results determined. A data processing routine and a data collection routine often are integrated and provide feedback to operate data acquisition by the instrument, and hence provide assay-based judging methods provided herein.

As used herein, software refers to computer readable program instructions that, when executed by a computer, perform computer operations. Typically, software is provided on a program product containing program instructions recorded on a computer readable medium, including, but not limited to, magnetic media including floppy disks, hard disks, and magnetic tape; and optical media including CD-ROM discs, DVD discs, magneto-optical discs, and other such media on which the program instructions can be recorded.

Different methods of predicting presence or absence of Y-chromosome nucleic acid can produce different types of results. For any given prediction, there are four possible types of outcomes: true positive, true negative, false positive, or false negative. The term "true positive" as used herein refers to a subject correctly diagnosed as having Y-chromosome nucleic acid. The term "false positive" as used herein refers to a subject wrongly identified as having Y-chromosome nucleic acid. The term "true negative" as used herein refers to a subject correctly identified as not having Y-chromosome nucleic acid. The term "false negative" as used herein refers to a subject wrongly identified as not having Y-chromosome nucleic acid. Two measures of performance for any given method can be calculated based on the ratios of these occurrences: (i) a sensitivity value, the fraction of predicted positives that are correctly identified as being positives (e.g., the fraction of nucleotide sequence sets correctly identified by level comparison detection/determination as indicative of Y-chromosome nucleic acid, relative to all nucleotide sequence sets identified as such, correctly or incorrectly), thereby reflecting the accuracy of the results in detecting the Y-chromosome nucleic acid; and (ii) a specificity value, the fraction of predicted negatives correctly identified as being negative (the fraction of nucleotide sequence sets correctly identified by level comparison detection/determination as indicative of absence of Y-chromosome nucleic acid, relative to all nucleotide sequence sets identified as such, correctly or incorrectly), thereby reflecting accuracy of the results in detecting the absence of Y-chromosome nucleic acid.

The term "sensitivity" as used herein refers to the number of true positives divided by the number of true positives plus the number of false negatives, where sensitivity (sens) may be within the range of $0 \leq sens \leq 1$. Ideally, method embodiments herein have the number of false negatives equaling zero or close to equaling zero, so that no subject is wrongly identified as not having Y-chromosome nucleic acid when they indeed have Y-chromosome nucleic acid. Conversely, an assessment often is made of the ability of a prediction algorithm to classify negatives correctly, a complementary measurement to sensitivity. The term "specificity" as used herein refers to the number of true negatives divided by the number of true negatives plus the number of false positives, where sensitivity (spec) may be within the range of $0 \leq spec \leq 1$. Ideally, methods embodiments herein have the number of false positives equaling zero or close to equaling zero, so that no subject wrongly identified as having Y-chromosome nucleic acid when they do not have the Y-chromosome nucleic acid. Hence, a method that has sensitivity and specificity equaling one, or 100%, sometimes is selected.

One or more prediction algorithms may be used to determine significance or give meaning to the detection data collected under variable conditions that may be weighed independently of or dependently on each other. The term "variable" as used herein refers to a factor, quantity, or function of an algorithm that has a value or set of values. For example, a variable may be the design of a set of amplified nucleic acid species, the number of sets of amplified nucleic acid species, percent fetal genetic contribution tested, percent maternal genetic contribution tested, type of sex-linked abnormalities assayed, the age of the mother and the like. The term "independent" as used herein refers to not being influenced or not being controlled by another. The term "dependent" as used herein refers to being influenced or controlled by another. For example, presence of Y-chromosome nucleic acid and male sex for a fetus are variables that are dependent upon each other.

Any suitable type of method or prediction algorithm may be utilized to give significance to the data of the present invention within an acceptable sensitivity and/or specificity. For example, prediction algorithms such as Mann-Whitney U Test, binomial test, log odds ratio, Chi-squared test, z-test, t-test, ANOVA (analysis of variance), regression analysis, neural nets, fuzzy logic, Hidden Markov Models, multiple model state estimation, and the like may be used. One or more methods or prediction algorithms may be determined to give significance to the data having different independent and/or dependent variables of the present invention. And one or more methods or prediction algorithms may be determined not to give significance to the data having different independent and/or dependent variables of the present invention. One may design or change parameters of the different variables of methods described herein based on results of one or more prediction algorithms (e.g., number of sets analyzed, types of nucleotide species in each set).

In certain embodiments, several algorithms may be chosen to be tested. These algorithms then can be trained with raw data. For each new raw data sample, the trained algorithms will assign a classification to that sample (i.e. male or female fetus). Based on the classifications of the new raw data samples, the trained algorithms' performance may be assessed based on sensitivity and specificity. Finally, an algorithm with the highest sensitivity and/or specificity or combination thereof may be identified.

As noted above, algorithms, software, processors and/or machines, for example, can be utilized to (i) process detection data pertaining to nucleotide sequence species and/or amplified nucleic acid species of sets, and/or (ii) identify the presence or absence of Y-chromosome nucleic acid.

In certain embodiments, provided are methods for determining fetal sex in a pregnant woman that comprise: (a) providing a system, where the system comprises distinct software modules, and where the distinct software modules comprise a signal detection module, a logic processing module, and a data display organization module; (b) detecting signal information indicating the presence or absence of Y chromosome nucleic acid in a sample from the pregnant female; (c) receiving, by the logic processing module, the signal information; (d) calling the fetal sex by the logic processing module, where the presence of Y chromosome nucleic acid is indicative of a male fetus, and the absence of Y chromosome nucleic acid is indicative of a female fetus; and (e) organizing, by the data display organization model in response to being called by the logic processing module, a data display indicating the sex of the fetus. The Y chromosome nucleic acid may be, for example, a nucleic acid corresponding to one or more Y chromosome loci described herein. The Y chromosome nucleic acid may, for example, be detected, may correspond to, or may be complementary to, a Y chromosome primer described herein.

In certain embodiments, provided are methods for determining the amount of fetal DNA in a sample, where the sample is obtained from a pregnant woman carrying a male fetus, which comprise: (a) providing a system, where the system comprises distinct software modules, and where the distinct software modules comprise a signal detection module, a logic processing module, and a data display organization module; (b) detecting signal information indicating the amount of Y chromosome nucleic acid in the sample; (c) receiving, by the logic processing module, the signal information; (d) calling the amount of fetal DNA in the sample by the logic processing module, where the amount of Y chromosome nucleic acid is indicative of the amount of fetal DNA in the sample; and (e) organizing, by the data display organization model in response to being called by the logic processing module, a data display indicating the amount of fetal DNA in the sample. The Y chromosome nucleic acid may be, for example, a nucleic acid corresponding to one or more Y chromosome loci described herein. The Y chromosome nucleic acid may, for example, be detected, may correspond to, or may be complementary to, a Y chromosome primer described herein.

Provided also are methods for determining fetal sex in a pregnant woman, which comprise providing signal information indicating the presence or absence of Y chromosome nucleic acid in a sample from the pregnant female; providing a system, where the system comprises distinct software modules, and where the distinct software modules comprise a signal detection module, a logic processing module, and a data display organization module; receiving, by the logic processing module, the signal information; calling the fetal sex by the logic processing module where the presence of Y chromosome nucleic acid is indicative of a male fetus, and the absence of Y chromosome nucleic acid is indicative of a female fetus; and organizing, by the data display organization model in response to being called by the logic processing module, a data display indicating the sex of the fetus. The Y chromosome nucleic acid may be, for example, a nucleic acid corresponding to one or more Y chromosome loci described herein. The Y chromosome nucleic acid may, for example, be detected, may correspond to, or may be complementary to, a Y chromosome primer described herein.

Provided also are methods for determining the amount of fetal DNA in a sample, where the sample is obtained from a pregnant woman carrying a male fetus, which comprise providing signal information indicating the amount of Y chromosome nucleic acid in the sample; providing a system, where the system comprises distinct software modules, and where the distinct software modules comprise a signal detection module, a logic processing module, and a data display organization module; receiving, by the logic processing module, the signal information; calling the amount of fetal DNA in the sample by the logic processing module where the amount of Y chromosome nucleic acid is indicative of the amount of fetal DNA in the sample; and organizing, by the data display organization model in response to being called by the logic processing module, a data display indicating amount of fetal DNA in the sample. The Y chromosome nucleic acid may be, for example, a nucleic acid corresponding to one or more Y chromosome loci described herein. The Y chromosome nucleic acid may, for example, be detected, may correspond to, or may be complementary to, a Y chromosome primer described herein.

Provided also are methods for determining fetal sex in a pregnant woman, which comprise providing a system, where the system comprises distinct software modules, and where the distinct software modules comprise a signal detection module, a logic processing module, and a data display organization module; receiving, by the logic processing module, signal information indicating the presence or absence of Y chromosome nucleic acid in a sample from the pregnant female; calling the fetal sex by the logic processing module where the presence of Y chromosome nucleic acid is indicative of a male fetus, and the absence of Y chromosome nucleic acid is indicative of a female fetus; and organizing, by the data display organization model in response to being called by the logic processing module, a data display indicating the sex of the fetus. The Y chromosome nucleic acid may be, for example, a nucleic acid corresponding to one or more Y chromosome loci described herein. The Y chromosome nucleic acid may, for example, be detected, may correspond to, or may be complementary to, a Y chromosome primer described herein.

Provided also are methods for determining the amount of fetal DNA in a sample, where the sample is obtained from a pregnant woman carrying a male fetus, which comprise providing a system, where the system comprises distinct software modules, and where the distinct software modules comprise a signal detection module, a logic processing module, and a data display organization module; receiving, by the logic processing module, signal information indicating the amount of Y chromosome nucleic acid in the sample; calling the amount of fetal DNA in the sample by the logic processing module, where the amount of Y chromosome nucleic acid is indicative of the amount of fetal DNA in the sample; and organizing, by the data display organization model in response to being called by the logic processing module, a data display indicating the amount of fetal DNA in the sample. The Y chromosome nucleic acid may be, for example, a nucleic acid corresponding to one or more Y chromosome loci described herein. The Y chromosome nucleic acid may, for example, be detected, may correspond to, or may be complementary to, a Y chromosome primer described herein.

By "providing signal information" is meant any manner of providing the information, including, for example, computer communication means from a local, or remote site, human data entry, or any other method of transmitting signal information. The signal information may be generated in one location and provided to another location.

By "obtaining" or "receiving" signal information is meant receiving the signal information by computer communication means from a local, or remote site, human data entry, or any other method of receiving signal information. The signal information may be generated in the same location at which it is received, or it may be generated in a different location and transmitted to the receiving location.

By "indicating" or "representing" the amount is meant that the signal information is related to, or correlates with, for example, the presence of Y chromosome nucleic acid. The information may be, for example, the calculated data associated with the presence of the nucleic acid as obtained, for example, after converting raw data obtained by mass spectrometry.

Also provided are computer program products, such as, for example, a computer program products comprising a computer usable medium having a computer readable program code embodied therein, the computer readable program code adapted to be executed to implement a method for determining fetal sex in a pregnant woman, which comprises (a) providing a system, where the system comprises distinct software modules, and where the distinct software modules comprise a signal detection module, a logic processing module, and a data display organization module; (b) detecting signal information indicating the presence or absence of Y chromosome nucleic acid in a sample from the pregnant female; (c) receiving, by the logic processing module, the signal information; (d) calling the fetal sex by the logic processing module where the presence of Y chromosome nucleic acid is indicative of a male fetus, and the absence of Y chromosome nucleic acid is indicative of a female fetus; and organizing, by the data display organization model in response to being called by the logic processing module, a data display indicating the sex of the fetus. The Y chromosome nucleic acid may be, for example, a nucleic acid corresponding to one or more Y chromosome loci described herein. The Y chromosome nucleic acid may, for example, be detected, may correspond to, or may be complementary to, a Y chromosome primer described herein.

Also provided are computer program products, such as, for example, a computer program products comprising a computer usable medium having a computer readable program code embodied therein, the computer readable program code adapted to be executed to implement a method for determining the amount of fetal DNA in a sample, where the sample is obtained from a pregnant woman carrying a male fetus, which comprises (a) providing a system, where the system comprises distinct software modules, and where the distinct software modules comprise a signal detection module, a logic processing module, and a data display organization module; (b) detecting signal information indicating the amount of Y chromosome nucleic acid in the sample; (c) receiving, by the logic processing module, the signal information; (d) calling the amount of fetal DNA in the sample by the logic processing module, where the amount of Y chromosome nucleic acid is indicative of the amount of fetal DNA in the sample; and (e) organizing, by the data display organization model in response to being called by the logic processing module, a data display indicating the amount of fetal DNA in the sample. The Y chromosome nucleic acid may be, for example, a nucleic acid corresponding to one or more Y chromosome loci described herein. The Y chromosome nucleic acid may, for example, be detected, may correspond to, or may be complementary to, a Y chromosome primer described herein.

Also provided are computer program products, such as, for example, computer program products comprising a computer usable medium having a computer readable program code embodied therein, the computer readable program code adapted to be executed to implement a method for determining fetal sex in a pregnant woman, which comprises providing a system, where the system comprises distinct software modules, and where the distinct software modules comprise a signal detection module, a logic processing module, and a data display organization module; receiving signal information indicating the presence or absence of Y chromosome nucleic acid in a sample from the pregnant female; calling the fetal sex by the logic processing module where the presence of Y chromosome nucleic acid is indicative of a male fetus, and the absence of Y chromosome nucleic acid is indicative of a female fetus; and organizing, by the data display organization model in response to being called by the logic processing module, a data display indicating the sex of the fetus. The Y chromosome nucleic acid may be, for example, a nucleic acid corresponding to one or more Y chromosome loci described herein. The Y chromosome nucleic acid may, for example, be detected, may correspond to, or may be complementary to, a Y chromosome primer described herein.

Also provided are computer program products, such as, for example, computer program products comprising a computer usable medium having a computer readable program code embodied therein, the computer readable program code adapted to be executed to implement a method for determining the amount of fetal DNA in a sample, where the sample is obtained from a pregnant woman carrying a male fetus, which comprises providing a system, where the system comprises distinct software modules, and where the distinct software modules comprise a signal detection module, a logic processing module, and a data display organization module; receiving signal information indicating the amount of Y chromosome nucleic acid in the sample; calling the amount of fetal DNA in the sample by the logic processing module, where the amount of Y chromosome nucleic acid is indicative of the amount of fetal DNA in the sample; and organizing, by the data display organization model in response to being called by the logic processing module, a data display indicating the amount of fetal DNA in the sample. The Y chromosome nucleic acid may be, for example, a nucleic acid corresponding to one or more Y chromosome loci described herein. The Y chromosome nucleic acid may, for example, be detected, may correspond to, or may be complementary to, a Y chromosome primer described herein.

Signal information may be, for example, mass spectrometry data obtained from mass spectrometry of RNA, or of amplified nucleic acid. As the RNA may be amplified into a nucleic acid that is detected, the signal information may be detection information, such as mass spectrometry data, obtained from stoichiometrically-produced nucleic acid from the RNA. The mass spectrometry data may be raw data, such as, for example, a set of numbers, or, for example, a two dimensional display of the mass spectrum. The signal information may be converted or transformed to any form of data that may be provided to, or received by, a computer system. The signal information may also, for example, be converted, or transformed to identification data or information representing the fetal sex. The signal information may also, for example, be converted or transformed to identification data or information representing the amount of fetal DNA.

Also provided is a machine for determining fetal sex in a pregnant woman, where the machine comprises a computer system having distinct software modules, and where the distinct software modules comprise a signal detection module, a logic processing module, and a data display organization module, where the software modules are adapted to be executed to implement a method for determining fetal sex in a pregnant woman, which comprises (a) detecting signal information indicating the presence or absence of Y chromosome nucleic acid in a sample from the pregnant female; (b) receiving, by the logic processing module, the signal information; (c) calling the fetal sex by the logic processing module, where the presence of Y chromosome nucleic acid is indicative of a male fetus, and the absence of Y chromosome nucleic acid is indicative of a female fetus; and organizing, by the data display organization model in response to being called by the logic processing module, a data display indicating the sex of the fetus. The Y chromosome nucleic acid may be, for example, a nucleic acid corresponding to one or more Y chromosome loci described herein. The Y chromosome nucleic acid may, for example, be detected, may correspond to, or may be complementary to, a Y chromosome primer described herein.

The machine may further comprise a memory module for storing signal information or data indicating fetal sex. Also provided are methods for determining fetal sex in a pregnant woman, where the methods comprise the use of a machine for determining fetal sex in a pregnant woman.

Also provided is a machine for determining the amount of fetal DNA in a sample, where the sample is obtained from a pregnant woman carrying a male fetus, where the machine comprises a computer system having distinct software modules, and where the distinct software modules comprise a signal detection module, a logic processing module, and a data display organization module, where the software modules are adapted to be executed to implement a method for determining the amount of fetal DNA in a sample, which comprises (a) detecting signal information indicating the amount of Y chromosome nucleic acid in the sample; (b) receiving, by the logic processing module, the signal information; (c) calling the amount of fetal DNA in the sample by the logic processing module, where the amount of Y chromosome nucleic acid is indicative of the amount of fetal DNA in the sample; and (e) organizing, by the data display organization model in response to being called by the logic processing module, a data display indicating the amount of fetal DNA in the sample. The Y chromosome nucleic acid may be, for example, a nucleic acid corresponding to one or more Y chromosome loci described herein. The Y chromosome nucleic acid may, for example, be detected, may correspond to, or may be complementary to, a Y chromosome primer described herein.

The machine may further comprise a memory module for storing signal information or data indicating the amount of fetal DNA. Also provided are methods for determining the amount of fetal DNA in a sample, where the sample is obtained from a pregnant woman carrying a male fetus, where the methods comprise the use of a machine for determining the amount of fetal DNA in a sample.

Also provided are methods for determining fetal sex in a pregnant woman that comprise: (a) detecting signal information, where the signal information indicates the presence or absence of Y chromosome nucleic acid in a sample from the pregnant female; (b) transforming the signal information representing presence or absence of Y chromosome nucleic acid into identification data, where the identification data represents the fetal sex. The Y chromosome nucleic acid may be, for example, a nucleic acid corresponding to one or more Y chromosome loci described herein. The Y chromosome nucleic acid may, for example, be detected, may correspond to, or may be complementary to, a Y chromosome primer described herein.

Also provided are methods for determining the amount of fetal DNA in a sample, where the sample is obtained from a pregnant woman carrying a male fetus, that comprise: (a) detecting signal information, where the signal information indicates the amount of Y chromosome nucleic acid in the sample; (b) transforming the signal information representing the amount of Y chromosome nucleic acid into identification data, where the identification data represents the amount of fetal DNA in the sample. The Y chromosome nucleic acid may be, for example, a nucleic acid corresponding to one or more Y chromosome loci described herein. The Y chromosome nucleic acid may, for example, be detected, may correspond to, or may be complementary to, a Y chromosome primer described herein.

Also provided are methods for determining fetal sex in a pregnant woman that comprise: (a) providing signal information indicating the presence or absence of Y chromosome nucleic acid in a sample from the pregnant female; (b) transforming the signal information representing the presence or absence of Y chromosome nucleic acid into identification data, where the identification data represents the fetal sex, whereby the presence of Y chromosome nucleic acid is indicative of a male fetus, and the absence of Y chromosome nucleic acid is indicative of a female fetus; and (c) displaying the identification data. The Y chromosome nucleic acid may be, for example, a nucleic acid corresponding to one or more Y chromosome loci described herein. The Y chromosome nucleic acid may, for example, be detected, may correspond to, or may be complementary to, a Y chromosome primer described herein.

Also provided are methods for determining the amount of fetal DNA in a sample, where the sample is obtained from a pregnant woman carrying a male fetus, that comprise: (a) providing signal information indicating the amount of Y chromosome nucleic acid in the sample; (b) transforming the signal information representing the amount of Y chromosome nucleic acid into identification data, where the identification data represents the amount of fetal DNA in the sample; and (c) displaying the identification data. The Y chromosome nucleic acid may be, for example, a nucleic acid corresponding to one or more Y chromosome loci described herein. The Y chromosome nucleic acid may, for example, be detected, may correspond to, or may be complementary to, a Y chromosome primer described herein.

Also provided are methods for determining fetal sex in a pregnant woman that comprise: (a) receiving signal information indicating the presence or absence of Y chromosome nucleic acid in a sample from the pregnant female; (b) transforming the signal information representing the presence or absence of Y chromosome nucleic acid into identification data, where the identification data represents the fetal sex, whereby the presence of Y chromosome nucleic acid is indicative of a male fetus, and the absence of Y chromosome nucleic acid is indicative of a female fetus; and (c) displaying the identification data. The Y chromosome nucleic acid may be, for example, a nucleic acid corresponding to one or more Y chromosome loci described herein. The Y chromosome nucleic acid may, for example, be detected, may correspond to, or may be complementary to, a Y chromosome primer described herein.

Also provided are methods for determining the amount of fetal DNA in a sample, where the sample is obtained from a pregnant woman carrying a male fetus that comprise: (a) receiving signal information indicating the amount of Y chromosome nucleic acid in the sample; (b) transforming the signal information representing the amount of Y chromosome nucleic acid into identification data, where the identification data represents the amount of fetal DNA in the sample; and (c) displaying the identification data. The Y chromosome nucleic acid may be, for example, a nucleic acid corresponding to one or more Y chromosome loci described herein. The Y chromosome nucleic acid may, for example, be detected, may correspond to, or may be complementary to, a Y chromosome primer described herein.

For purposes of these, and similar embodiments, the term "signal information" indicates information readable by any electronic media, including, for example, computers that represent data derived using the present methods. For example, "signal information" can represent the amount of Y chromosome nucleic acid; a ratio of Y chromosome nucleic acid to female nucleic acid, an amount of amplified nucleic acid that corresponds to, or is complementary to, a Y chromosome locus, or an amount of amplified nucleic acid that corresponds to, or is complementary to, more than one Y chromosome locus. Signal information, such as in these examples, that represents physical substances may be transformed into identification data, such as a visual display that represents other physical substances, such as, for example, fetal sex. Identification data may be displayed in any appropriate manner, including, but not limited to, in a computer visual display, by encoding the identification data into computer readable media that may, for example, be transferred to another electronic device (e.g., electronic record), or by creating a hard copy of the display, such as a print out or physical record of information. The information may also be displayed by auditory signal or any other means of information communication. In some embodiments, the signal information may be detection data obtained using methods to detect the Y chromosome nucleic acid.

Once the signal information is detected, it may be forwarded to the logic processing module. The logic processing module may "call" or "identify" the fetal sex.

Provided also are methods for transmitting prenatal genetic information to a human pregnant female subject, which comprise determining the fetal sex in a pregnant woman where the fetal sex has been determined from the presence or absence of Y chromosome nucleic acid in a sample from the pregnant female; and transmitting the fetal sex to the pregnant female subject. The Y chromosome nucleic acid may be, for example, a nucleic acid corresponding to one or more Y chromosome loci described herein. The Y chromosome nucleic acid may, for example, be detected, may correspond to, or may be complementary to, a Y chromosome primer described herein.

Provided also are methods for transmitting prenatal genetic information to a human pregnant female subject carrying a male fetus, which comprise determining the amount of fetal DNA in a sample obtained from the pregnant woman, and where the amount of fetal DNA has been determined from the amount of Y chromosome nucleic acid in the sample; and transmitting the amount of fetal DNA to the pregnant female subject. The Y chromosome nucleic acid may be, for example, a nucleic acid corresponding to one or more Y chromosome loci described herein. The Y chromosome nucleic acid may, for example, be detected, may correspond to, or may be complementary to, a Y chromosome primer described herein.

Provided also are methods for transmitting prenatal genetic information to a human pregnant female subject, which comprise determining the fetal sex in a pregnant woman where the fetal sex has been determined from the presence or absence of Y chromosome nucleic acid in a sample from the pregnant female; and transmitting prenatal genetic information representing the fetal sex to the pregnant female subject. The Y chromosome nucleic acid may be, for example, a nucleic acid corresponding to one or more Y chromosome loci described herein. The Y chromosome nucleic acid may, for example, be detected, may correspond to, or may be complementary to, a Y chromosome primer described herein.

Provided also are methods for transmitting prenatal genetic information to a human pregnant female subject carrying a male fetus, which comprise determining the amount of fetal DNA in a sample is obtained from the pregnant woman, and where the amount of fetal DNA has been determined from the amount of Y chromosome nucleic acid in the sample; and transmitting prenatal genetic information representing the amount of fetal DNA in the sample to the pregnant female subject. The Y chromosome nucleic acid may be, for example, a nucleic acid corresponding to one or more Y chromosome loci described herein. The Y chromosome nucleic acid may, for example, be detected, may correspond to, or may be complementary to, a Y chromosome primer described herein.

The terms "determining the fetal sex" or "determining the amount of fetal DNA" as used herein refers to any method for obtaining such information, including, without limitation, obtaining the information from a laboratory file. A laboratory file can be generated by a laboratory that carried out an assay to determine the fetal sex in a pregnant woman or the amount of fetal DNA in a sample. The laboratory may be in the same location or different location (e.g., in another country) as the personnel identifying the fetal sex or the amount of fetal DNA from the laboratory file. For example, the laboratory file can be generated in one location and transmitted to another location in which the information therein will be transmitted to the pregnant female subject. The laboratory file may be in tangible form or electronic form (e.g., computer readable form), in certain embodiments.

The term "transmitting the fetal sex to the pregnant female subject" or "transmitting the amount of fetal DNA in the sample" or any other information transmitted as used herein refers to communicating the information to the female subject, or family member, guardian or designee thereof, in a suitable medium, including, without limitation, in verbal, document, or file form.

Also provided are methods for providing to a human pregnant female subject a medical prescription based on prenatal genetic information, which comprise determining the fetal sex in a pregnant female, where the fetal sex has been determined from the presence or absence of Y chromosome nucleic acid in a sample from the pregnant female; and providing a medical prescription based on the fetal sex. The Y chromosome nucleic acid may be, for example, a nucleic acid corresponding to one or more Y chromosome loci described herein. The Y chromosome nucleic acid may, for example, be detected, may correspond to, or may be complementary to, a Y chromosome primer described herein.

Also provided are methods for providing to a human pregnant female subject carrying a male fetus a medical prescription based on prenatal genetic information, which comprise determining the amount of fetal DNA in a sample, obtained from the pregnant woman, where the amount of fetal DNA has been determined from the amount of Y chromosome nucleic acid in the sample; and providing a medical prescription based on the amount of fetal DNA in the sample. The Y chromosome nucleic acid may be, for example, a nucleic acid corresponding to one or more Y chromosome loci described herein. The Y chromosome nucleic acid may, for example, be detected, may correspond to, or may be complementary to, a Y chromosome primer described herein.

The term "providing a medical prescription based on prenatal genetic information" refers to communicating the prescription to the female subject, or family member, guardian or designee thereof, in a suitable medium, including, without limitation, in verbal, document or file form.

Also provided are methods for providing to a human pregnant female subject a medical prescription based on prenatal genetic information, which comprise reporting to the pregnant female subject the fetal sex in the pregnant female, where the fetal sex has been determined from the presence or absence of Y chromosome nucleic acid in a sample from the pregnant female; and providing a medical prescription based on fetal sex to the pregnant female subject. The Y chromosome nucleic acid may be, for example, a nucleic acid corresponding to one or more Y chromosome loci described herein. The Y chromosome nucleic acid may, for example, be detected, may correspond to, or may be complementary to, a Y chromosome primer described herein.

Also provided are methods for providing to a human pregnant female subject carrying a male fetus, a medical prescription based on prenatal genetic information, which comprise reporting to the pregnant female subject the amount of fetal DNA in a sample obtained from the pregnant woman, where the amount of fetal DNA has been determined from the amount of Y chromosome nucleic acid in the sample; and providing a medical prescription based on the amount of fetal DNA in the sample to the pregnant female subject. The Y chromosome nucleic acid may be, for example, a nucleic acid corresponding to one or more Y chromosome loci described herein. The Y chromosome nucleic acid may, for example, be detected, may correspond to, or may be complementary to, a Y chromosome primer described herein.

The medical prescription may be for any course of action determined by, for example, a medical professional upon reviewing the prenatal genetic information. For example, the prescription may be for the pregnant female subject to undergo an amniocentesis procedure. Or, in another example, the medical prescription may be for the pregnant female subject to undergo another genetic test. In yet another example, the medical prescription may be medical advice to not undergo further genetic testing.

Also provided are files, such as, for example, a file comprising the determination of fetal sex in a pregnant female subject, where the fetal sex has been determined from the presence or absence of Y chromosome nucleic acid in a sample from the pregnant female.

Also provided are files, such as, for example, a file comprising the determination of the amount of fetal DNA in a sample, where the sample is obtained from a pregnant woman carrying a male fetus, where the amount of fetal DNA has been determined from the amount of Y chromosome nucleic acid in the sample.

The file may be, for example, but not limited to, a computer readable file, a paper file, or a medical record file.

Computer program products include, for example, any electronic storage medium that may be used to provide instructions to a computer, such as, for example, a removable storage device, CD-ROMS, a hard disk installed in hard disk drive, signals, magnetic tape, DVDs, optical disks, flash drives, RAM or floppy disk, and the like.

The systems discussed herein may further comprise general components of computer systems, such as, for example, network servers, laptop systems, desktop systems, handheld systems, personal digital assistants, computing kiosks, and the like. The computer system may comprise one or more input means such as a keyboard, touch screen, mouse, voice recognition or other means to allow the user to enter data into the system. The system may further comprise one or more output means such as a CRT or LCD display screen, speaker, FAX machine, impact printer, inkjet printer, black and white or color laser printer or other means of providing visual, auditory or hardcopy output of information.

The input and output means may be connected to a central processing unit which may comprise among other components, a microprocessor for executing program instructions and memory for storing program code and data. In some embodiments the methods may be implemented as a single user system located in a single geographical site. In other embodiments methods may be implemented as a multi-user system. In the case of a multi-user implementation, multiple central processing units may be connected by means of a network. The network may be local, encompassing a single department in one portion of a building, an entire building, span multiple buildings, span a region, span an entire country or be worldwide. The network may be private, being owned and controlled by the provider or it may be implemented as an internet based service where the user accesses a web page to enter and retrieve information.

The various software modules associated with the implementation of the present products and methods can be suitably loaded into the a computer system as desired, or the software code can be stored on a computer-readable medium such as a floppy disk, magnetic tape, or an optical disk, or the like. In an online implementation, a server and web site maintained by an organization can be configured to provide software downloads to remote users. As used herein, "module," including grammatical variations thereof, means, a self-contained functional unit which is used with a larger system. For example, a software module is a part of a program that performs a particular task. Thus, provided herein is a machine comprising one or more software modules described herein, where the machine can be, but is not limited to, a computer (e.g., server) having a storage device such as floppy disk, magnetic tape, optical disk, random access memory and/or hard disk drive, for example.

The present methods may be implemented using hardware, software or a combination thereof and may be implemented in a computer system or other processing system. An example computer system may include one or more processors. A processor can be connected to a communication bus. The computer system may include a main memory, sometimes random access memory (RAM), and can also include a secondary memory. The secondary memory can include, for example, a hard disk drive and/or a removable storage drive, representing a floppy disk drive, a magnetic tape drive, an optical disk drive, memory card etc. The removable storage drive reads from and/or writes to a removable storage unit in a well-known manner. A removable storage unit includes, but is not limited to, a floppy disk, magnetic tape, optical disk, etc. which is read by and written to by, for example, a removable storage drive. As will be appreciated, the removable storage unit includes a computer usable storage medium having stored therein computer software and/or data.

In alternative embodiments, secondary memory may include other similar means for allowing computer programs or other instructions to be loaded into a computer system. Such means can include, for example, a removable storage unit and an interface device. Examples of such can include a program cartridge and cartridge interface (such as that found in video game devices), a removable memory chip (such as an EPROM, or PROM) and associated socket, and other removable storage units and interfaces which allow software and data to be transferred from the removable storage unit to a computer system.

The computer system may also include a communications interface. A communications interface allows software and data to be transferred between the computer system and external devices. Examples of communications interface can include a modem, a network interface (such as an Ethernet card), a communications port, a PCMCIA slot and card, etc. Software and data transferred via communications interface are in the form of signals, which can be electronic, electromagnetic, optical or other signals capable of being received by communications interface. These signals are provided to communications interface via a channel. This channel carries signals and can be implemented using wire or cable, fiber optics, a phone line, a cellular phone link, an RF link and other communications channels. Thus, in one example, a communications interface may be used to receive signal information to be detected by the signal detection module.

In a related aspect, the signal information may be input by a variety of means, including but not limited to, manual input devices or direct data entry devices (DDEs). For example, manual devices may include, keyboards, concept keyboards, touch sensitive screens, light pens, mouse, tracker balls, joysticks, graphic tablets, scanners, digital cameras, video digitizers and voice recognition devices. DDEs may include, for example, bar code readers, magnetic strip codes, smart cards, magnetic ink character recognition, optical character recognition, optical mark recognition, and turnaround documents. In one embodiment, an output from a gene or chip reader my serve as an input signal.

In some embodiments, provided is a kit for determining the fetal sex in a pregnant woman. One component of the kit is primers for amplifying the region of interest, such as, for example, primers directed to one or more loci described herein. Another component of the kit may be, for example, a standard control primer representing chromosome nucleic acid that is not Y-chromosome specific.

In some embodiments, provided is a kit for determining the amount of fetal DNA in a sample, where the sample is obtained from a pregnant woman carrying a male fetus. One component of the kit is primers for amplifying the region of interest, such as, for example, primers directed to one or more loci described herein. Another component of the kit may be, for example, a standard control primer representing chromosome nucleic acid that is not Y-chromosome specific.

Kits

Furthermore, the invention in part provides kits comprising compositions described herein and optionally instructions for carrying out methods described herein. Parts of the kit can be packaged individually in vials or in combination in containers or multicontainer units. Kits may be advantageously used for carrying out methods described herein and can be, inter alia, employed in a variety of applications referred herein. Manufacture of kits often are in accordance with standard procedures known to persons skilled in the art.

EXAMPLES

The following examples illustrate certain embodiments of the invention and are not limiting. Those of skill in the art will readily recognize a variety of non-critical parameters that can be changed or modified to yield essentially similar results.

Example 1

Fetal Sex Assay

Determination of fetal sex was enabled by multiplex PCR followed by multiplexed primer extension analysis using MALDI-TOF MS. Initial testing on male and female genomic DNA showed the ability of the assay system to discriminate the presence or absence of Y-chromosomal DNA. Secondary studies were performed using DNA mixtures with as low as 20 genomic copies of either male or female DNA mixed with a 50-fold excess of female genomic DNA.

Testing of the assay using maternal plasma and non-pregnant female plasma samples was performed and shows a high degree of reproducibility between replicate sample aliquots of maternal plasma and high specificity as determined by the lack of Y-chromosomal target detection in plasma DNA isolated from non-pregnant female donors.

Detailed Steps for the Fetal Sex Determination Assay Protocol

The protocol provided below does not limit the scope of the invention. Instead it provides an representative protocol for practicing a part of the invention.

1. Prepare multiplex PCR primer mix using a set of primers provided in Table 3 (MP set 1, 2, 3 or 4). Mix 100 ump primer (5.0 up volume) with 910 ul water for a final concentration of 0.5 uM.

TABLE 3

| MP Set | ASSAY ID | 2nd-PCR Primer | SEQ ID NO | 1st-PCR Primer | SEQ ID NO | Extend Primer | SEQ ID NO |
|---|---|---|---|---|---|---|---|
| 1 | SRY-4-i-2 | ACGTTGGATGGCATTTCCACTGGTATCCC | 1 | ACGTTGGATGAGATGGCTCTAGAGAATCCC | 35 | CCAGAATGCGAAACTC | 68 |
| | HSFY-1 | ACGTTGGATGGAAAGTTGCCTTTCTGCCTGC | 2 | ACGTTGGATGTTCCTCCTCTCCACCCC | 36 | CCCATCTCTTCTCAATCC | 69 |
| | RBMY2-1 | ACGTTGGATGGAAGTTGGGAGAGTTACTCG | 3 | ACGTTGGATGAGAGAAGGCGATTCCTTTG | 37 | AAACATGCTCACGATCAC | 70 |
| | ALB-2-i | ACGTTGGATGGCAAATTCAGTACTACTTCATTC | 4 | ACGTTGGATGCAGTATCTTCAGCAGTGTCC | 38 | GCAGTGTCCATTTGAAGAT | 71 |
| | TTTY22-1 | ACGTTGGATGCTCTGGCTAGCATCACAATG | 5 | ACGTTGGATGACGAAGGCTACTTCTCTAC | 39 | GCAGGGACTTGTCGCTAGG | 72 |
| | RBMY1A1-1 | ACGTTGGATGCTATTCTTGCCGAGAACC | 6 | ACGTTGGATGGAACCTCAGGCTCTTTGTCC | 40 | AAAAAGCGCAGTATTTTCTG | 73 |
| | XKRY-1 | ACGTTGGATGTCCCTCTGTGGTACAGAAAC | 7 | ACGTTGGATGATGACCCCAAAAGCACAGAC | 41 | CAATTGGATCACATTACATCAAA | 74 |
| | TTTY16-1 | ACGTTGGATGTCGAATTTGATTCCAGAGG | 8 | ACGTTGGATGTCCCAGACTGAAATCCCAAG | 42 | ggggTGAAATCCCAAGACAATGGA | 75 |
| | CDY1-1 | ACGTTGGATGGTCAGGAGATCGAGACAATC | 9 | ACGTTGGATGCTGGCCTACGAATTGTTG | 43 | GGCCCTACGAATTGTTGTATTTTT | 76 |
| 2 | PRY-2 | ACGTTGGATGCTTGAGTCTGGGAGTTTGAG | 10 | ACGTTGGATGACCACCAGCTGGCTAATTTG | 44 | GTCACATTTGTTGCCCT | 77 |
| | TTTY22-2 | ACGTTGGATGACTAGGCACCTCATTCTCAG | 11 | ACGTTGGATGTCCAGTAGTCTTCAGTGTTGAGAG | 45 | GGACTCTCAATGAAAGCA | 78 |
| | ALB-2-i [1] | ACGTTGGATGGCAAATTCAGTACTACTTCATTC | 4 | ACGTTGGATGCAGTATCTTCAGCAGTGTCC | 38 | GCAGTGTCCATTTGAAGAT | 71 |
| | XKRY-2 | ACGTTGGATGGGCATTCGTTGGTGATTATC | 12 | ACGTTGGATGAGTGTAAGCTCCCCGTGTTTC | 46 | tGGAAGAATGCCAGAGTCA | 79 |
| | TTTY16-2 | ACGTTGGATGCCTCATGAGGGATATGTGC | 13 | ACGTTGGATGATGAGTGCATTGACTGTGAC | 47 | TAGCCATAGTGCACATCTCA | 80 |
| | RBMY2-2 | ACGTTGGATGTCTTTGCTGAGAAAGGAC | 14 | ACGTTGGATGAGTGACACAGGGAAAACACG | 48 | CTCTTCACTGATTTTAAAGTTT | 81 |
| | BPY22-2 | ACGTTGGATGGTAGAGTAGAGTCACACTCC | 15 | ACGTTGGATGTGATGAACGCCTCAAAG | 49 | TGTCACCAAGCACACTATTGCCAGG | 82 |
| | RBMY1A1-2 | ACGTTGGATGCTTTTAGAGCGTAGACAAAC | 16 | ACGTTGGATGCTTTTAGAGCGTAGACAAAC | 50 | TAGAGCGTAGACAAACTGGATAGACA | 83 |
| | CDY1-2 | ACGTTGGATGTGTGAGGGCAGAGAAGTGTC | 17 | ACGTTGGATGAAAGACACGGGATTGGAAC | 51 | cccagTGGAACAGTTGCTGTGCCACCT | 84 |
| 3 | SRY-4-i-2[1] | ACGTTGGATGGCATTTCCACTGGTATCCC | 1 | ACGTTGGATGAGATGGCTCTAGAGAATCCC | 35 | CCAGAATGCGAAACTC | 68 |
| | CYORF14-3 | ACGTTGGATGATCAACAAACAAGGGGCTTC | 18 | ACGTTGGATGCTACTGGGTCTAGCCTTAT | 52 | GACATGAAGTCATTTGCT | 85 |
| | ALB-3-i | ACGTTGGATGGCAAATTCAGTACTTCATTC | 4 | ACGTTGGATGCAGTATCTTCAGCAGTGTCC | 38 | cGCAGTGTCCATTTGAAGAT | 86 |

TABLE 3-continued

| MP Set | ASSAY ID | 2nd-PCR Primer | SEQ ID NO | 1st-PCR Primer | SEQ ID NO | Extend Primer | SEQ ID NO |
|---|---|---|---|---|---|---|---|
| | TTTY22-3 | ACGTTGGATGACCCCCAATAGAAGTGATAG | 19 | ACGTTGGATGTGGCTGGACAGCTTTCATAC | 53 | AATTCGAGTTACAG CCACCG | 87 |
| | RBMY1A1-3 | ACGTTGGATGTCATACGTAGAGATCGGTG | 20 | ACGTTGGATGTGGAAATGTGTTGGCTTGGG | 54 | GTATCCTGAAGCCAAT AAATAC | 88 |
| | XKRY-3 | ACGTTGGATGAGGCCAAATAGTCTTTACTC | 21 | ACGTTGGATGCCCTGAAGGAATAAATGGAC | 55 | GAAGGAATAAATGGACT CTCGAT | 89 |
| | HSFY-3 | ACGTTGGATGGTCATCTGCACTAGGCATTC | 22 | ACGTTGGATGTACCAAGGCATTGGACTCTG | 56 | CTGCACATGAGATACATA TCTTCC | 90 |
| | PRY-3 | ACGTTGGATGAATTCAGAGCCTGACCCAAG | 23 | ACGTTGGATGTGTGGACCCCAGGATATAAC | 57 | GTGGACCCCAGGATATAA CAAATTA | 91 |
| | CDY1-3 | ACGTTGGATGGCATGCCTCCCCTTGCTGTC | 24 | ACGTTGGATGGGGTAAAGCATCTGCCAATG | 58 | CTGCCAATGAAATGTTAAT TGCTGGGC | 92 |
| 4 | HSFY-4 | ACGTTGGATGGCTCTCTACTTTACCTTCCC | 25 | ACGTTGGATGTGGAACATAGAGAGCACCAG | 59 | AGCAACCCAACC CTCTGC | 93 |
| | TTTY16-4 | ACGTTGGATGTCAAGACTGTGAGGTGGTTG | 26 | ACGTTGGATGATGGTCCTGATTCTTGCAC | 60 | GGCTCTTTCAGG AATGGA | 94 |
| | XKRY-4 | ACGTTGGATGTGGAAGTTACAGGCCTTGAG | 27 | ACGTTGGATGTGACAAAGTCGACTCAGTGC | 61 | TTGCACCTGTATCA CACAGT | 95 |
| | RBMY1A1-4 | ACGTTGGATGGACCATAGTCTCAGTATGCC | 28 | ACGTTGGATGGCACACAAATCATCCAAG | 62 | GTTCCCGAGAAACT AGGGATT | 96 |
| | TTTY22-4 | ACGTTGGATGGGAAGTTTGTATAATTGCTCC | 29 | ACGTTGGATGCAATGTTCACTGCCATTCC | 63 | CCAATTGACTGCTCAAA TTTACA | 97 |

TABLE 3-continued

| MP Set | ASSAY ID | 2nd-PCR Primer | SEQ ID NO | 1st-PCR Primer | SEQ ID NO | Extend Primer | SEQ ID NO |
|---|---|---|---|---|---|---|---|
| | ALB-4-i | ACGTTGGATGGCAAATTCAGTTACTTCATTC | 4 | ACGTTGGATGCAGTATCTTCAGCAGTGTCC | 38 | tccGCAGTGTCCATTTGAAGAT | 98 |
| | BPY22-4 | ACGTTGGATGTCAACCAAGGGATGAAAGCC | 30 | ACGTTGGATGAATGATGCTTCAGTCCCACC | 64 | GCCAGAGCCACAGAGGGCATTTT | 99 |
| | CDY1-4 | ACGTTGGATGGCTTTTGCATAACTGAGCAC | 31 | ACGTTGGATGCCGCTACACTTTGTATGACC | 65 | ccccgGTCTCTTTTTATGAGCACA | 100 |
| | RBMY2-4 | ACGTTGGATGGTCAGGTACATACTAAAATGC | 32 | ACGTTGGATGTGTAACACTCAGAGCAAAGG | 66 | GTAACACTCAGAGCAAAGGGGCACT | 101 |
| 5 | DBY | ACGTTGGATGCTGAATGAAAGTTCAAACGTC | 33 | ACGTTGGATGGATACTATGCCACCAAAGGG | 67 | gACAGTACCTGTATTTCCTTAG | 102 |
| 6 | TTTY | ACGTTGGATGTACCTTATGGCAGGGACTTG | 34 | ACGTTGGATGCTCTGCTAGCATCACAATG | 5 | gTATGCAGGGACTTGTCGCTAGG | 103 |

PCR primers and extend primers are provided in Table 3.
Designations MP1-MP4 correspond to multiplex (MP) primer sets 1-4.
The underlined portion of the primer is a universal tag sequence for improved amplification reactions.
Lower case nucleotides in the extend primer sequence represent non-template nucleotides that increase the mass of the oligonucleotide.

In Table 3, MP5 provides PCR primers and an extend primer directed to exon 6 of the dead box, Y isoform gene (NCBI reference mRNA sequence NM_004660 (DBY); chromosome positions chrY:13537002-13537120 from NCBI Build 36.1)

MP6 provides PCR primers and an extend primer directed to two sequences on the Y chromosome: testis-specific transcript, Y-linked 22-5'UTR (NCBI reference mRNA sequence AF527463 (TTTY22); chromosome positions chrY: 10248638-10248718 from NCBI Build 36.1) and an unnamed sequence that is 26 kb upstream of TTTY1 (chrY: 6291654-6291734 from NCBI Build 36.1). The TTTY assay provides an ultra-sensitive test for gender determination since two Y-chromosome sequences are detected.

The SRY assay provides PCR primers and an extend primer directed to exon 1 of the sex determining region Y (NCBI reference mRNA sequence NM_003140.1 (SRY); chromosome positions chrY:2715334-2715425 from NCBI Build 36.1). This assay may be used alone or in combination with other assays to determine the sex of a fetus, or to determine the amount of fetal nucleic acid present in a sample.

2. Prepare PCR cocktail as in Table 4.

TABLE 4

PCR cocktail preparation with UNG

| Reagent | Conc. in 50 ul rxn | Volume reagent for 50 ul reaction (ul) |
|---|---|---|
| Water, HPLC grade | N/A | 7.55 |
| 10xPCR Buffer (contains 15 mM MgCl2, Tris-Cl, KCl, (NH4)2SO4, pH 8.7 (20° C.) | 1.25x | 6.25 |
| 25 mM MgCl2 (Qiagen) | 1.625 mM | 3.25 |
| PCR Nucleotide Mix PLUS (10 mM dATP, dCTP, dGTP/30 mM dUTP) | 200 μM | 1 |
| 0.5 uM PCR primer mix -F, -R | 0.1 μM | 10 |
| 1 U/μl Uracil-DNA-Glycosylase (UNG)(NEB) | 1.25 U/rxn | 1.25 |
| 5 U/μl HotStar Taq (Qiagen) | 3.5 U/rxn | 0.7 |
| DNA (plasma) Added Separately | — | 20 |
| Total | | 50 |

3. To the DNAs, add 30 uL PCR cocktail per well, mixing well.
4. Seal plate and centrifuge.
5. Run PCR with _PCR30-11_ program on PCR cycler (Table 5).

TABLE 5

PCR 30-11 Thermocycling Conditions

| PCR Cycle | Cycling Conditions | Number of Cycles |
|---|---|---|
| UDG Incubation | 30° C. for 10 minutes | 1 Cycle |
| Initial Denaturation | 94° C. for 15 minutes | 1 Cycle |
| Cycled Template Denaturation | 94° C. for 20 seconds | 30 Cycles |
| Cycled primer Annealing | 58° C. for 30 seconds | |
| Cycled primer Extension | 72° C. for 1 minute | |
| Cycled Template Denaturation | 94° C. for 20 seconds | 11 Cycles |
| Cycled primer Annealing | 62° C. for 30 seconds | |
| Cycled primer Extension | 72° C. for 1 minute | |
| Final Extension | 72° C. for 3 minute | 1 Cycle |
| Hold | 4° C. | |

6. Prepare SAP cocktail as in Table 6.

TABLE 6

SAP Cocktail Mix

| SAP Mix Reagent | Volume for 1 rxn (ul) |
|---|---|
| Nanopure Water | 2.95 uL |
| SAP Buffer | 0.34 uL |
| Shrimp Alkaline Phosphatase (SAP) (1.7 U/uL) | 0.71 uL |
| Total Volume | 4.00 uL |

7. From the PCR plate, aliquot 10 uL PCR into a new 96-well plate.
8. Dispense 4 uL SAP cocktail mix into the PCR aliquoted plate.
9. Seal plate, centrifuge, and cycle using the SAP 40-5 conditions in Table 7.

TABLE 7

SAP Thermal Cycling Conditions - SAP_40_5

| SAP Cycle | Cycling Conditions | Number of Cycles |
|---|---|---|
| Initial Incubation | 37° C. for 40 minutes | 1 Cycle |
| Cycled Template Denaturation | 85° C. for 5 minutes | 1 Cycle |
| Hold | 4° C. | |

10. Prepare a multiplexed extend primer mix according to Table 8.

TABLE 8

Extend Primer Mix Preparation

| 200 uM Extend primer | Conc. in mix | Volume primer | Volume Water | Final conc. primer in 18 uL rxn |
|---|---|---|---|---|
| SRY-4-i-2 | 7 uM | 17.5 | 272.5 | 0.625 uM |
| HSFY-1 | 7 uM | 17.5 | | |
| RBMY2-1 | 7 uM | 17.5 | | |
| ALB-2-i | 7 uM | 17.5 | | |
| TTTY22-1 | 7 uM | 17.5 | | 1.25 uM |
| RBMY1A1-1 | 14 uM | 35 | | |
| XKRY-1 | 14 uM | 35 | | |
| TTTY16-1 | 14 uM | 35 | | |
| CDY1-1 | 14 uM | 35 | | |
| Total | | 500 ul | | |

11. Prepare EXTEND cocktail as in Table 9 using the corresponding multiplex set of Extend Primers provided in Table 3.

TABLE 9

| Extend Reagent | Volume for 1 rxn |
|---|---|
| Water (HPLC grade) | 1.238 uL |
| iPLEX Buffer Plus (10x) | 0.4 uL |
| iPLEX termination Mix | 0.4 uL |
| Extend Primer Mix, 7/14 uM | 1.88 uL |
| Thermosequenase (32 U/uL) | 0.082 uL |
| Total Volume | 4.0 uL |

12. Dispense 4 uL of the Extend cocktail mix into corresponding wells of the plate from the SAP incubation step.

13. Seal plate, centrifuge, and cycle with the following conditions in Table 10.

TABLE 10

200 step EXTEND cycling

| PCR Cycle | Cycling Conditions | Number of Cycles | |
|---|---|---|---|
| Initial Denaturation | 94° C. for 30 seconds | 1 Cycle | |
| Cycled Template Denaturation | 94° C. for 5 seconds | | |
| Cycled primer Annealing | 52° C. for 5 seconds | | 40 cycles |
| Cycled primer Extension | 80° C. for 5 seconds | 5 cycles | |
| Final Extension | 72° C. for 3 minutes | | |
| Hold | 4° C. | | |

14. Sample Conditioning, Dispensing, and Acquiring Spectra:
  a. Add 32 ul water per well.
  b. Add 15 mg Clean Resin, per well.
  c. Rotate 360 degrees for 10 min. Centrifuge at 4000 rpm for 5 minutes
15. Spotting to SpectroCHIP® solid support and MALDI run:
  a. Pintool: Samsung 6-pin Nanodispenser
  b. pintool settings:
    i. Calibrant: 96 to 96, non-skirted plate in adapter, 120 mm/sec dispense speed
    ii. Analyte: 96 to 96, non-skirted plate in adapter, 20-50 mm/sec dispense speed (dependent upon volume check)

Steps 10-14 are further described hereafter. Following genomic amplification, the assay interrogates amplified regions through the use of specific primers that are designed to hybridize directly adjacent to the site of interest. These DNA oligonucleotides are referred to as iPLEX® MassEXTEND® primers. In the extension reaction, the iPLEX primers are hybridized to the complementary DNA templates and extended with a DNA polymerase. Special termination mixtures that contain different combinations of deoxy- and dideoxynucleotide triphosphates along with enzyme and buffer, direct limited extension of the iPLEX primers. Primer extension occurs until a complementary dideoxynucleotide is incorporated.

The extension reaction generates primer products of varying length, each with a unique molecular weight. As a result, the primer extension products can be simultaneously separated and detected using Matrix Assisted Laser Desorption/Ionization, Time-Of-Flight (MALDI-TOF) mass spectrometry on the Sequenom MassARRAY® Analyzer Compact System.

Assay Performance

Initial development of XLR (X-linked, Lymphocyte Regulated) assay was performed by designing assay multiplexes that each amplified 11 Y-chromosomal sequences and the ALB sequence. These were tested for their ability to generate assay calls and successful primer extension when amplifying ~1000 genomic copies of male DNA. At high DNA copy number, assays within each multiplex gave expected calls but variable extend rates with 35-40 PCR cycles and a 200 step extend cycling reaction. Further testing was performed using a dilution series of template DNA with 50-800 genomic copies of male DNA per reaction. As indicated by decreased call rates and extend rates, these studies identified individual Y-chromosome assays within the multiplexes that showed decreased performance when using lower amounts of DNA template. The three poorest performing Y-chromosome target assays from each multiplex were removed to give four multiplexes designed to amplify eight Y-chromosomal sequences and ALB. See Table 3.

Performance of each of these resulting 9-plexes was tested using between 12-400 copies of male genomic DNA, with results showing equivalently high call rates in assays of multiplexes 1, 2 and 4 at all levels of male genomic DNA, but with variable extension rates. Also in these studies, multiplex 3 showed consistent call drop out of one Y-chromosome assay (PRY-4) when using low copy numbers of male DNA. These resulting nine-plexes were carried forward for further testing using the DNA mixture model system described below.

Multiplexing Results

A mixture model was developed to test the ability of the four XLR gender multiplexes to detect low copy numbers of Y-chromosomal target sequences in a high copy number background of female genomic DNA. This model system was designed to mimic the mixtures of fetal and maternal DNA in a maternal plasma sample. In this model, mixtures were prepared so that each PCR would receive 20 genomic copies ('fetal') of either a male or female CEPH genomic DNA combined with 980 genomic copies ('maternal') of a female CEPH DNA to generate a 2% mixture of 'fetal'/'maternal' DNA. Five female 'fetal' DNAs and six 'fetal' male DNAs were combined with 8 female 'maternal' DNAs, to generate 88 unique DNA samples for analysis.

Specific PCR and extend primer sequences used for the four individual multiplexes are listed in Table 3.

The four XLR multiplexes containing ALB and 8 Y-chromosomal assays were tested for their ability to detect Y-chromosomal targets in the 2% DNA mixtures described above. Standard PCR 40 58-2s-62 cycling conditions were used for these studies.

Each of the multiplexes showed some degree of spurious Y-target calls in samples containing only female DNA. MP1, MP2, MP3, and MP4 showed 7, 3, 7, and 8 spurious Y-target calls, respectively, when using female/female DNA mixtures. These spurious calls are possibly associated with the method of PCR set up for the DNA mixtures, with the use of a prePCR liquid handler (Matrix) to add DNA to the PCR plate containing aliquoted PCR cocktail. MP1 was the only multiplex that showed all Y-target calls for samples containing 2% male genomic DNA. MP2 showed notable dropout for Y-target assays PRY-2 and TTTY22-2 in samples containing 2% male genomic DNA. MP3 showed notable dropout for TTTY22-3 and no detection of the PRY-3 target in samples containing 2% male genomic DNA. MP4 showed notable dropouts for TTTY22-4 target detection in samples containing 2% male genomic DNA. The assay failure involving the TTTY22 loci in multiplexes 2, 3, and 4 occurred only in DNA mixtures containing the male DNA NA04477. One potential explanation might be DNA specific alteration of the TTTY22 region that interferes with amplification using the specific amplicon designs for TTTY22-2, TTTY22-3, and TTTY22-4, but not the TTTY22-1 assay design in MP1. Because MP1 was the only multiplex without dropout of Y-target calls in samples containing Y-chromosomal template and MP1 showed similar levels of spurious calls to the other multiplexes, MP1 was carried forward to further testing. However, MP2, MP3 and MP4 are still considered good tests for the determination of fetal sex.

Replicate Analysis

Replicate analysis of the 2% male DNA mixtures was used to test the reproducibility of Y-target detection in samples containing Y-chromosomal DNA template and specificity of Y-target detection in samples containing no Y-chromosomal template. PCR-40 58-2s-62 cycling was used in these studies. All Y-target assays were successfully called in samples containing male DNA (XY/XX samples on right side of the panel). Multiple spurious Y-target calls were made in female DNA only samples. While there was no correlation between specific DNAs and spurious calls, spurious Y-target call rates were highest in assays RBMY1a1 and RBMY2. The RBMY gene family has multiple copies on the Y-chromosome and shares homology with RBMX gene on the X-chromosome. One or both of these factors may play a role in the higher degree of spurious calls for the RBMY assays. One explanation is that the higher copy numbers of the RBMY template on the Y-chromosome may lead to higher chances of successful amplification when there is a single copy contamination event with Y-chromosome fragments containing the RBMY gene loci. Alternatively, non-specific recognition of RBMX template by RBMY primers at early PCR cycle number may lead to amplification. However, this non-specific amplification appears unlikely as there were no candidate template sites identified when gene specific PCR primer sequences for both RBMY1a1 and RBMY2 assay were queried through the NCBI reverse e-PCR site.

PCR Cycling Conditions

In an effort to match assay conditions between RHD and XLR, PCR cycling conditions used for the RHD assay (PCR 30-11) were tested with XLR MP1. In addition, a higher stringency cycling condition (PCR 40-62) was also tested. These additional cycling conditions are summarized in Table 11.

With PCR 40-62 cycling conditions, no improvement was seen in RBMY1a1 and RBMY2 spurious call rates. Spurious calls rates may be improved in other assays using the PCR 40-62 conditions, however, this condition was tested on only one plate replicate.

Of note, the median extension rate of assay CDY1-1 was improved from ~75% in both the PCR 40 58-2s-62 and PCR 30-11 cycling conditions to nearly complete extension when using PCR 40-62 conditions. However, as there was no change in call rate with cycling conditions, it was decided that PCR 30-11 cycling would be used in future work in an effort to minimize differences between the XLR assay and RHD assays.

TABLE 11

| | Alternate PCR cycling conditions | | |
|---|---|---|---|
| PCR 30-11 | UNG Incubation | 30° C. 10 minutes | 1 cycle |
| | Taq Activation | 94° C. 15 minutes | 1 cycle |
| | Denature | 94° C. 20 seconds | 30 cycles |

TABLE 11-continued

| | Alternate PCR cycling conditions | | |
|---|---|---|---|
| | Anneal | 58° C. 30 seconds | |
| | Elongation | 72° C. 60 seconds | |
| | Denature | 94° C. 20 seconds | 10 cycles |
| | Anneal | 62° C. 30 seconds | |
| | Elongation | 72° C. 60 seconds | |
| | Final Elongation | 72° C. 3 minutes | 1 cycle |
| | Storage | 4° C. forever | 1 cycle |
| PCR 40-62 | UNG Incubation | 30° C. 10 minutes | 1 cycle |
| | Taq Activation | 94° C. 15 minutes | 1 cycle |
| | Denature | 94° C. 20 seconds | 40 cycles |
| | Anneal | 62° C. 30 seconds | |
| | Elongation | 72° C. 60 seconds | |
| | Final Elongation | 72° C. 3 minutes | 1 cycle |
| | Storage | 4° C. forever | 1 cycle |

Analytical Sensitivity

In five replicate analyses of 48 DNA mixtures containing 20 genomic copies of male DNA in a background of 980 genomic copies female DNA, 8 Y-targets were detected in each case using the MP1 assay design with PCR 40 58-2s-62 cycling conditions. Using an assay calling rule of 8 positive Y-targets to determine the presence of male DNA, there was 100% sensitivity to detect the presence of male DNA in this model system.

In five replicate analyses of 40 DNA mixtures containing 1000 genomic copies of only female DNA, 0 Y-target calls in 169 of 200 samples containing only female DNA, 1 Y-target call in 26 of 200 female DNA samples, and 2 Y-target calls in 5 of 200 female DNA samples measured.

Plasma Samples from Pregnant Women

Maternal plasma was collected using an IRB approved protocol with donor consent. 20 mL peripheral blood was collected in lavender top EDTA blood tubes. Following collection, samples were centrifuged and the plasma fraction transferred to individual 1 mL aliquots. Aliquoted plasma was stored at −80° C.

For all plasma samples, plasma DNA was isolated using the QIAamp Viral MinElute kit from Qiagen® with the vacuum protocol. Final elution was performed with 60 ul water, and 20 ul of this eluate was used for PCR unless otherwise indicated. PCR 30-11 cycling conditions were used unless indicated. TypePLEX extend reaction was performed with the 200 extension reaction cycling.

Any DNA isolation, extraction or enrichment method known in the art or not yet developed may be used that yields sufficient fetal nucleic acid.

Maternal plasma obtained from Precision Med protocol #3402 was used to test the ability of fetal gender assay MP1 to detect to the presence of Y-chromosomal DNA in maternal plasma. For this study, 2 separate aliquots of 14 second trimester maternal plasma samples were tested independently on different days. Of these samples, fetal gender phenotype was known in only 5 pregnancies.

Shown in FIG. 2 below is the summary of Y-target calls for the first replicate of each plasma aliquot from each assay date. Of the 14 samples, 6 donors (right most six samples) appear to carry a male fetus as judged by the presence of 8 Y-target calls in both analysis dates. Male fetal gender phenotype was confirmed in 2 of these pregnancies but no fetal gender phenotype information was available for the remaining 4 samples. Of the 8 samples on the left of the figure, 5 show no Y-target calls in either replicate analysis, while 3 show 1 Y-target call in either the 20070829 or 20071130 analysis but not both. Given the results from the DNA model testing of female only DNAs showing 0-2 Y-target calls, these results suggest these 8 donors carry a female fetus. Female fetal gender was confirmed in 3 of these pregnancies, but no fetal gender phenotype information was available for the remaining 5 samples as of the preparation of this report. Of the results with apparent female fetus, spurious calls for samples #204, 218, and 251 were for RBMY1a1, TTTY16, and RBMY2, respectively.

Plasma Samples from Non-Pregnant Female

Figure 3:
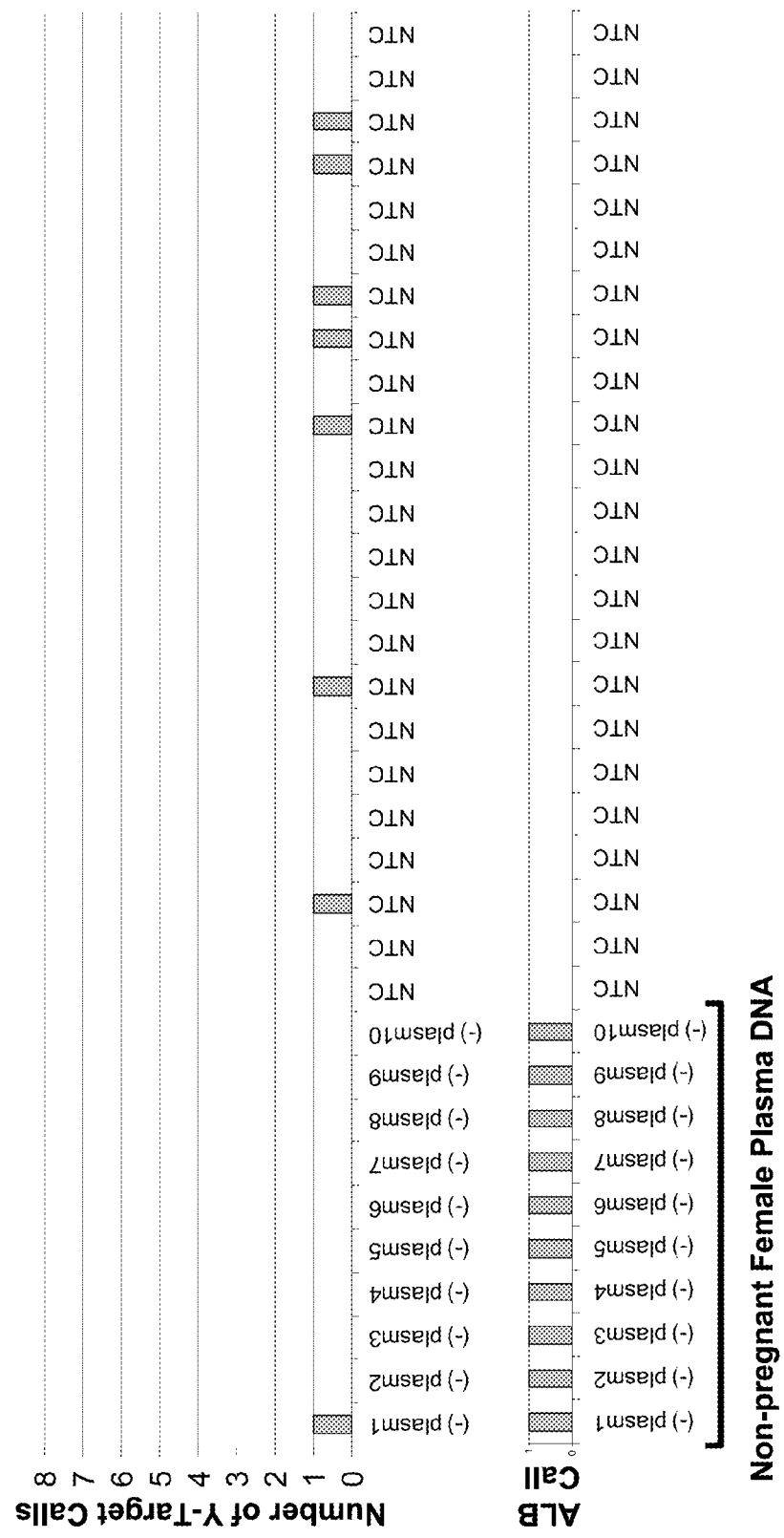
FIG. 3 shows the results from the analysis of non-pregnant female plasma DNA. Top panel shows the number of Y-target calls for each replicate non-pregnant female plasma DNA or NTC. Bottom panel shows the presence or absence of ALB call for each sample to indicate successful PCR. (NTC=non-template control).

Replicate plasma aliquots obtained from a non-pregnant female donor were tested in parallel as a negative control for the later Precision Med 3402 sample analysis (20071130). As seen in FIG. 3, of 10 non-pregnant female plasma DNA preparations, only one aliquot showed 1 Y-target call. Inclusion of 23 NTC PCRs (water only) showed 7 NTC samples each with one Y-target call. The remaining 16 NTC samples showed no Y-target calls. These results correspond to those seen in DNA mixture model testing.

Additional Plasma Samples

In addition to the plasma samples above, plasma samples from Hemacare® protocols #0049 and #0071 were assayed. In total, 57 plasma aliquots obtained from 25 donors at varying time points during pregnancy were assayed. These included 8 donors with plasma obtained from each trimester, 5 donors with plasma obtained from both 1st and 2nd trimester, and 12 donors with plasma collected from 1st trimester only. No fetal gender information was available for these samples at the time of testing.

Fifty-two PCR analyses showed 8 Y-target calls. These plasma DNA isolates were derived from 12 donors and show 100% concordance for 8 Y-target calls between both plasma DNA PCR replicate testing and sampling at various trimesters. This demonstrates the high degree of reproducibility of results when all Y-targets are called. Of the remaining 62 plasma DNA PCR replicates, 20 show 0 Y-target calls and 42 show 1-4 Y-target calls. Samples #004, #011 and #063 (with 3, 3, and 4 Y-target calls in at least one PCR replicate, respectively) are from donor very likely carrying female fetuses. This conclusion can be reached by comparing Y-target calls from individual plasma DNA replicate preparations between plasma samples collected in the 1st, 2nd, and 3rd trimesters of pregnancy for these donors. Of note in the samples with 1-4 Y-target calls is the minimal concordance of Y-target calls that are made between PCR replicates, indicating a high degree of variability in these calls and that the variability arises during the PCR amplification. That the spurious calls originate in the PCR is consistent with knowledge gained in prior development of RHD and other assays.

In total, there were 69 Y-target calls in all Hemacare plasma samples that showed less than 8 positive Y-targets. All assays except RBMY1a1 and RBMY2 gave between 3-6 calls per Y-target assay in these samples. However, Y-target assays for RBMY1a1 and RBMY2 gave 26 and 16 calls, respectively in these samples.

Using the remaining portion of plasma DNA isolated from the original plasma aliquot, a third PCR replicate was generated for samples 001 (as a negative control), 003 (as a positive control), 004, 011, and 063. The DNA volume used in these PCRs was only 12-17 ul instead of the 20 ul used in the first 2 PCR replicates due to limited sample volume. The resulting PCR product was assayed in duplicate in the TypePLEX extend reaction.

Overall Performance Assessment

The 2% DNA mixture models studies demonstrated the ability of XLR MP1 to detect male DNA in a sample at concentrations as low as 20 genomic copies in a background of female genomic DNA as high as 980 genomic copies. In the replicate studies of MP1, XLR MP1 gave 8 Y-target calls in 240 of 240 samples analyses containing male DNA. In parallel, the XLR MP1 assay gave 0 Y-target calls in 169 of 200 samples containing only female DNA, 1 Y-target call in 26 of 200 female DNA samples, and 2 Y-target calls in 5 of 200 female DNA samples measured. These results demonstrate a distinct grouping pattern whereby the presence of male DNA in a sample, even at concentrations as low as 20 genomic copies, will give 8 Y-target calls and the absence of male DNA in the sample will give less than 2 Y-targets calls.

Representative criteria for assay calling are provided in Table 12.

TABLE 12

| Y-target calls | Assay result call |
| --- | --- |
| 8 | Male |
| 3-7 | Inconclusive |
| 0-2 | Female |

Example 2

Examples of Embodiments

Described hereafter are non-limiting examples of certain embodiments of the invention.

A1. A method for identifying the presence or absence of Y-chromosome nucleic acid in extracellular nucleic acid from a pregnant female, which comprises:

(a) contacting under amplification conditions extracellular nucleic acid from a pregnant female with one or more primer sets selected from the group consisting of:

| first primer | SEQ ID NO: | corresponding second primer | SEQ ID NO: |
| --- | --- | --- | --- |
| AGATGGCTCTAGAGAATCCC | 104 | GCATTTTCCACTGGTATCCC | 137 |
| TTTCCTCTCTCTCCACCCC | 105 | AAAGTTGCCTTTCTGCCTGC | 138 |
| AGAGAAGGCGGATTCCTTTG | 106 | GAAGTTGGGAGAGTTACTCG | 139 |
| ACGAAGGGCTACTTCTCTAC | 107 | CTCTGGCTAGCATCACAATG | 136 |
| GAACCTCAGGCTCTTTGTCC | 108 | TCTATTCTTGCCGAGAGACC | 140 |
| ATGACCCCAAAAGCACAGAC | 109 | TCCCTCTGTGGTACAGAAAC | 141 |
| TCCCAGACTGAAATCCCAAG | 110 | TCGAATTTGATTCCCAGAGG | 142 |
| CTGGCCCTACGAATTTGTTG | 111 | GTCAGGAGATCGAGACAATC | 143 |

-continued

| first primer | SEQ ID NO: | corresponding second primer | SEQ ID NO: |
|---|---|---|---|
| ACCACAGCTGGCTAATTTTG | 112 | CTTGAGTCTGGGAGTTTGAG | 144 |
| TCCAGTAGTGCTGTTGAGAG | 113 | ACTAGGCACCTCATTCTCAG | 145 |
| AGTGTAAGCTCCCCTGTTTC | 114 | GGCATTCGTTGGTGATTATC | 146 |
| ATGGTGGCATTGACTGTGAC | 115 | CCTCATGAAGGGATATGTGC | 147 |
| AGTGACACAGGGAAAACACG | 116 | TTCTTTGGCTGAGAAAGGAC | 148 |
| GTGATGTGACAGCCTCAAAG | 117 | GTAGAGTAGAGTGACACTCC | 149 |
| CTTTTAGAGCGTAGACAAAC | 118 | GAGTCTTTCCTTCTTGTGCG | 150 |
| GAAAGCACGGGATTGGAAC | 119 | TGGAGGCAGAAAGAAGTGTC | 151 |
| AGATGGCTCTAGAGAATCCC | 104 | GCATTTTCCACTGGTATCCC | 137 |
| GCTACTGGGTCTAGCCTTAT | 120 | ATCAACAAACAAGGGGCTTC | 152 |
| TGGCTGGACAGCTTTCATAC | 121 | ACCCCCAATAGAAGTGATAG | 153 |
| TGGAAATGTGTTGGCTTGGG | 122 | TCATACGTAGAGTATCGGTG | 154 |
| CCCTGAAGGAATAAATGGAC | 123 | AGGCCAAATAGTCTTTACTC | 155 |
| TACCAAGGCATTGGACTCTG | 124 | GTCATCTGCACTAGGCATTC | 156 |
| TGTGGACCCCAGGATATAAC | 125 | AATTCAGAGCCTGACCCAAG | 157 |
| GGGTAAAGCATCTGCCAATG | 126 | GCATGCCTCCCTTGCTGTC | 158 |
| TGGAACATAGAGAGCACCAG | 127 | GCTCTCTACTTTACCTTCCC | 159 |
| ATGGGTCCTGATTCTTGCAC | 128 | TCAAGACTGTGAGGTGGTTG | 160 |
| TGACAAAGTCGACTCAGTGC | 129 | TGGAAGTTACAGGCCTTGAG | 161 |
| GCACACACAAATCATCCAAG | 130 | GACCATAGTCTCAGTATGCC | 162 |
| CAATGTTCACTGCCCATTCC | 131 | GGAAGTTTGTATAATTGCTCC | 163 |
| AATGATGCTTCAGTCCCACC | 132 | TCAACCAAGGGATGAAAGCC | 164 |
| CCGCTACACTTTGTATGACC | 133 | GCTTTTGCATAACTGAGCAC | 165 |
| TGTAACACTCAGAGCAAAGG | 134 | GTCAGGTACATACTAAAATGC | 166 |
| GATACTATGCCACCAAAGGG | 135 | CTGAATGAAAGTTCAAACGTC | 167 |
| CTCTGGCTAGCATCACAATG | 136 | TACCTTATGGCAGGGACTTG. | 168 | wherein (i) the nucleic acid comprises maternal nucleic acid and fetal nucleic acid, (ii) each primer of each primer set hybridizes to Y-chromosome nucleic acid, and (iii) each primer set consists of a first primer and a corresponding second primer; and
  (b) detecting the presence or absence of amplification product from each primer set, whereby the presence of Y-chromosome nucleic acid is based on detecting the presence of the amplification product.

A2. The method of embodiment A1, wherein the extracellular nucleic acid is deoxyribonucleic acid (DNA).

A3. The method of embodiment A1, wherein the extracellular nucleic acid is ribonucleic acid (RNA).

A4. The method of embodiment A1, wherein the extracellular nucleic acid is contacted with one or more primer sets selected from the group consisting of

| first primer | SEQ ID NO: | corresponding second primer | SEQ ID NO: |
|---|---|---|---|
| AGATGGCTCTAGAGAATCCC | 104 | GCATTTTCCACTGGTATCCC | 137 |
| GATACTATGCCACCAAAGGG | 135 | CTGAATGAAAGTTCAAACGTC | 167 |
| CTCTGGCTAGCATCACAATG | 136 | TACCTTATGGCAGGGACTTG. | 168 |

A5. The method of embodiment A1, wherein detecting the presence or absence of the amplification product comprises contacting under extension conditions each amplification product with an extension oligonucleotide selected from the group consisting of

| | SEQ ID NO: |
|---|---|
| CCAGAATGCGAAACTC | 68 |
| CCCATCTCTTCTCAATCC | 69 |
| AAACATGCTCACGATCAC | 70 |
| GCAGGGACTTGTCGCTAGG | 72 |
| AAAAAGCGCAGGTATTTTCTG | 73 |
| CAATTGGATCACATTACATCAAA | 74 |
| TGAAATCCCAAGACAATGGA | 169 |
| GGCCCTACGAATTTGTTGTATTTTT | 76 |
| GTCACATTTTGTTGCCCT | 77 |
| GGACTCTCAATGAAAGCA | 78 |
| GGAAGAATGCCAGAGTCA | 170 |
| TAGCCATAGTGCACATCTCA | 80 |
| CTCTTCACTGATTTTAAAGTTT | 81 |
| TGTCACCAAGCACACTATTGCCAGG | 82 |
| TAGAGCGTAGACAAACTGGATAGACA | 83 |
| TGGAACAGTTGCTGTGCCACCT | 171 |
| CCAGAATGCGAAACTC | 68 |
| GACATGAAGTCATTTGCT | 85 |
| AATTCGAGTTACAGCCACCG | 87 |
| GTATCCTGAAGCCAATAAATAC | 88 |
| GAAGGAATAAATGGACTCTCGAT | 89 |
| CTGCACATGAGATACATATCTTCC | 90 |
| GTGGACCCCAGGATATAACAAATTA | 91 |
| CTGCCAATGAAATGTTAATTGCTGGGC | 92 |
| AGCAACCCAACCCTCTGC | 93 |
| GGCTCTTTCAGGAATGGA | 94 |
| TTGCACCTGTATCACACAGT | 95 |
| GTTCCCGAGAAACTAGGGATT | 96 |
| CCATTGACTGCTCAAATTTACA | 97 |

| | SEQ ID NO: |
|---|---|
| GCCAGAGCCACAGAGGGCATTTT | 99 |
| GTCTCTTTTTATGAGCACA | 172 |
| GTAACACTCAGAGCAAAGGGGCACT | 101 |
| ACAGTACCTGTATTTCCTTAG | 173 |
| TATGGCAGGGACTTGTCGCTAGG | 174 | and detecting extended extension oligonucleotide.

A6. The method of embodiment A5, wherein the extension oligonucleotide is selected from the group consisting of

| | SEQ ID NO: |
|---|---|
| CCAGAATGCGAAACTC | 68 |
| ACAGTACCTGTATTTCCTTAG | 173 |
| TATGGCAGGGACTTGTCGCTAGG. | 174 |

A7. The method of embodiment A5 or embodiment A6, wherein the extended extension oligonucleotide is detected by mass spectrometry.

A8. The method of any one of embodiments A1-A7, wherein the extracellular nucleic acid is from blood serum.

A9. The method of any one of embodiments A1-A7, wherein the extracellular nucleic acid is from blood plasma.

A10. The method of any one of embodiments A1-A9, which further comprises determining the sex of the fetus based on the presence or absence of Y-chromosome nucleic acid, whereby the presence of Y-chromosome nucleic acid determines the fetus is male.

A11. The method of any one of embodiments A1-A10, wherein one or both primers in a primer set include a universal tag sequence.

A12. The method of any one of embodiments A1-A11, which further comprises contacting the extracellular nucleic acid with a control primer set under amplification conditions and detecting the presence or absence of a control amplification product from the control primer set, wherein the control primers of the control primer set can hybridize to the maternal nucleic acid.

A13. The method of embodiment A12, wherein the control primers of the control primer set hybridize to a nucleotide sequence that encodes or controls the expression of an albumin protein.

A14. The method of embodiment A13, wherein the control primer set comprises the following control primers:

| first primer | SEQ ID NO: | corresponding second primer | SEQ ID NO: |
|---|---|---|---|
| CAGTATCTTCAGCAGTGTCC | 175 | GCAAATTCAGTTACTTCATTC. | 176 |

A15. The method of any one of embodiments A12-A14, wherein detecting the presence or absence of the control amplification product comprises contacting under extension conditions each control amplification product with a control extension oligonucleotide and detecting extended control extension oligonucleotide.

A16. The method of embodiment A15, wherein the control extension oligonucleotide has the nucleotide sequence GCAGTGTCCATTTGAAGAT (SEQ ID NO: 71).

A17. The method of any one of embodiments A1-A16, wherein the extracellular nucleic acid is contacted with two or more primer sets in a multiplex reaction.

A18. The method of any one of embodiments A1-A3, A5 and A7-A17, wherein the extracellular nucleic acid is contacted with the following primer sets

| first primer | SEQ ID NO: | corresponding second primer | SEQ ID NO: |
| --- | --- | --- | --- |
| AGATGGCTCTAGAGAATCCC | 104 | GCATTTTCCACTGGTATCCC | 137 |
| TTTCCTCTCTCTCCACCCC | 105 | AAAGTTGCCTTTCTGCCTGC | 138 |
| AGAGAAGGCGGATTCCTTTG | 106 | GAAGTTGGGAGAGTTACTCG | 139 |
| ACGAAGGGCTACTTCTCTAC | 107 | CTCTGGCTAGCATCACAATG | 136 |
| GAACCTCAGGCTCTTTGTCC | 108 | TCTATTCTTGCCGAGAGACC | 140 |
| ATGACCCCAAAAGCACAGAC | 109 | TCCCTCTGTGGTACAGAAAC | 141 |
| TCCCAGACTGAAATCCCAAG | 110 | TCGAATTTGATTCCCAGAGG | 142 |
| CTGGCCCTACGAATTTGTTG | 111 | GTCAGGAGATCGAGACAATC. | 143 |

B1. A method for determining the presence or absence of Y-chromosome nucleic acid in a sample from a pregnant female, the method comprising amplifying nucleic acid from the sample from the pregnant female with at least one primer pair selected from Table 3, wherein each primer in the primer pair may comprise the entire sequence shown in the table or only the non-underlined sequence-specific portion, wherein the presence of amplification products indicates the presence of Y-chromosome nucleic acid.

B2. A method for determining the presence or absence of Y-chromosome nucleic acid in a sample from a pregnant female, the method comprising:
a) contacting nucleic acid from a pregnant female with at least one primer pair selected from Table 3, wherein each primer of the primer pair may comprise the entire sequence shown in the table or only the non-underlined sequence-specific portion;
and b) contacting nucleic acid amplification products of step a) with at least one corresponding extend primer from Table 3, wherein the presence of extend products indicates the presence of Y-chromosome nucleic acid.

B3. The method of embodiment B1 or embodiment B2, which is further limited by one or more applicable embodiments presented in any one of embodiments A1-A19.

C1. A method for determining the amount of fetal nucleic acid in a sample of extracellular nucleic acid from a pregnant female, which comprises:
(a) contacting under amplification conditions extracellular nucleic acid from a pregnant female with one or more primer sets selected from the group consisting of:

| first primer | SEQ ID NO: | corresponding second primer | SEQ ID NO: |
| --- | --- | --- | --- |
| AGATGGCTCTAGAGAATCCC | 104 | GCATTTTCCACTGGTATCCC | 137 |
| TTTCCTCTCTCTCCACCCC | 105 | AAAGTTGCCTTTCTGCCTGC | 138 |
| AGAGAAGGCGGATTCCTTTG | 106 | GAAGTTGGGAGAGTTACTCG | 139 |
| ACGAAGGGCTACTTCTCTAC | 107 | CTCTGGCTAGCATCACAATG | 136 |
| GAACCTCAGGCTCTTTGTCC | 108 | TCTATTCTTGCCGAGAGACC | 140 |
| ATGACCCCAAAAGCACAGAC | 109 | TCCCTCTGTGGTACAGAAAC | 141 |
| TCCCAGACTGAAATCCCAAG | 110 | TCGAATTTGATTCCCAGAGG | 142 |
| CTGGCCCTACGAATTTGTTG | 111 | GTCAGGAGATCGAGACAATC | 143 |
| ACCACAGCTGGCTAATTTTG | 112 | CTTGAGTCTGGGAGTTTGAG | 144 |

-continued

| first primer | SEQ ID NO: | corresponding second primer | SEQ ID NO: |
|---|---|---|---|
| TCCAGTAGTGCTGTTGAGAG | 113 | ACTAGGCACCTCATTCTCAG | 145 |
| AGTGTAAGCTCCCCTGTTTC | 114 | GGCATTCGTTGGTGATTATC | 146 |
| ATGGTGGCATTGACTGTGAC | 115 | CCTCATGAAGGGATATGTGC | 147 |
| AGTGACACAGGGAAAACACG | 116 | TTCTTTGGCTGAGAAAGGAC | 148 |
| GTGATGTGACAGCCTCAAAG | 117 | GTAGAGTAGAGTGACACTCC | 149 |
| CTTTTAGAGCGTAGACAAAC | 118 | GAGTCTTTCCTTCTTGTGCG | 150 |
| GAAAGACACGGGATTGGAAC | 119 | TGGAGGCAGAAAGAAGTGTC | 151 |
| AGATGGCTCTAGAGAATCCC | 104 | GCATTTTCCACTGGTATCCC | 137 |
| GCTACTGGGTCTAGCCTTAT | 120 | ATCAACAAACAAGGGGCTTC | 152 |
| TGGCTGGACAGCTTTCATAC | 121 | ACCCCAATAGAAGTGATAG | 153 |
| TGGAAATGTGTTGGCTTGGG | 122 | TCATACGTAGAGTATCGGTG | 154 |
| CCCTGAAGGAATAAATGGAC | 123 | AGGCCAAATAGTCTTTACTC | 155 |
| TACCAAGGCATTGGACTCTG | 124 | GTCATCTGCACTAGGCATTC | 156 |
| TGTGGACCCCAGGATATAAC | 125 | AATTCAGAGCCTGACCCAAG | 157 |
| GGGTAAAGCATCTGCCAATG | 126 | GCATGCCTCCCTTGCTGTC | 158 |
| TGGAACATAGAGAGCACCAG | 127 | GCTCTCTACTTTACCTTCCC | 159 |
| ATGGGTCCTGATTCTTGCAC | 128 | TCAAGACTGTGAGGTGGTTG | 160 |
| TGACAAAGTCGACTCAGTGC | 129 | TGGAAGTTACAGGCCTTGAG | 161 |
| GCACACACAAATCATCCAAG | 130 | GACCATAGTCTCAGTATGCC | 162 |
| CAATGTTCACTGCCCATTCC | 131 | GGAAGTTTGTATAATTGCTCC | 163 |
| AATGATGCTTCAGTCCCACC | 132 | TCAACCAAGGGATGAAAGCC | 164 |
| CCGCTACACTTTGTATGACC | 133 | GCTTTTGCATAACTGAGCAC | 165 |
| TGTAACACTCAGAGCAAAGG | 134 | GTCAGGTACATACTAAAATGC | 166 |
| GATACTATGCCACCAAAGGG | 135 | CTGAATGAAAGTTCAAACGTC | 167 |
| CTCTGGCTAGCATCACAATG | 136 | TACCTTATGGCAGGGACTTG. | 168 | wherein (i) the nucleic acid comprises maternal nucleic acid and fetal nucleic acid, (ii) each primer of each primer set hybridizes to Y-chromosome nucleic acid, and (iii) each primer set consists of a first primer and a corresponding second primer; and
  (b) determining the amount of amplification product from each primer set, whereby the amount of fetal nucleic acid in the extracellular nucleic acid is determined based on the amount of the amplification product.

C2. The method of embodiment C1, wherein the extracellular nucleic acid is deoxyribonucleic acid (DNA).

C3. The method of embodiment C1, wherein the extracellular nucleic acid is ribonucleic acid (RNA).

C4. The method of embodiment C1, wherein the extracellular nucleic acid is contacted with one or more primer sets selected from the group consisting of

| first primer | SEQ ID NO: | corresponding second primer | SEQ ID NO: |
|---|---|---|---|
| AGATGGCTCTAGAGAATCCC | 104 | GCATTTTCCACTGGTATCCC | 137 |
| GATACTATGCCACCAAAGGG | 135 | CTGAATGAAAGTTCAAACGTC | 167 |
| CTCTGGCTAGCATCACAATG | 136 | TACCTTATGGCAGGGACTTG. | 168 |

C5. The method of embodiment C1, wherein detecting the presence or absence of the amplification product comprises contacting under extension conditions each amplification product with an extension oligonucleotide selected from the group consisting of

| | SEQ ID NO: |
|---|---|
| CCAGAATGCGAAACTC | 68 |
| CCCATCTCTTCTCAATCC | 69 |
| AAACATGCTCACGATCAC | 70 |
| GCAGGGACTTGTCGCTAGG | 72 |
| AAAAAGCGCAGGTATTTTCTG | 73 |
| CAATTGGATCACATTACATCAAA | 74 |
| TGAAATCCCAAGACAATGGA | 169 |
| GGCCCTACGAATTTGTTGTATTTTT | 76 |
| GTCACATTTTGTTGCCCT | 77 |
| GGACTCTCAATGAAAGCA | 78 |
| GGAAGAATGCCAGAGTCA | 170 |
| TAGCCATAGTGCACATCTCA | 80 |
| CTCTTCACTGATTTTAAAGTTT | 81 |
| TGTCACCAAGCACACTATTGCCAGG | 82 |
| TAGAGCGTAGACAAACTGGATAGACA | 83 |
| TGGAACAGTTGCTGTGCCACCT | 171 |
| CCAGAATGCGAAACTC | 68 |
| GACATGAAGTCATTTGCT | 85 |
| AATTCGAGTTACAGCCACCG | 87 |
| GTATCCTGAAGCCAATAAATAC | 88 |
| GAAGGAATAAATGGACTCTCGAT | 89 |
| CTGCACATGAGATACATATCTTCC | 90 |
| GTGGACCCCAGGATATAACAAATTA | 91 |
| CTGCCAATGAAATGTTAATTGCTGGGC | 92 |
| AGCAACCCAACCCTCTGC | 93 |
| GGCTCTTTCAGGAATGGA | 94 |
| TTGCACCTGTATCACACAGT | 95 |
| GTTCCCGAGAAACTAGGGATT | 96 |
| CCATTGACTGCTCAAATTTACA | 97 |

| | SEQ ID NO: |
|---|---|
| GCCAGAGCCACAGAGGGCATTTT | 99 |
| GTCTCTTTTTATGAGCACA | 172 |
| GTAACACTCAGAGCAAAGGGGCACT | 101 |
| ACAGTACCTGTATTTCCTTAG | 173 |
| TATGGCAGGGACTTGTCGCTAGG | 174 | and detecting extended extension oligonucleotide.

C6. The method of embodiment C5, wherein the extension oligonucleotide is selected from the group consisting of

| | SEQ ID NO: |
|---|---|
| CCAGAATGCGAAACTC | 68 |
| ACAGTACCTGTATTTCCTTAG | 173 |
| TATGGCAGGGACTTGTCGCTAGG. | 174 |

C7. The method of embodiment C5 or embodiment C6, wherein the extended extension oligonucleotide is detected by mass spectrometry.

C8. The method of any one of embodiments C1-C7, wherein the extracellular nucleic acid is from blood serum.

C9. The method of any one of embodiments C1-C7, wherein the extracellular nucleic acid is from blood plasma.

C10. The method of any one of embodiments C1-C9, wherein the amount of the fetal nucleic acid is expressed as a percentage of fetal nucleic acid in the extracellular nucleic acid.

C11. The method of any one of embodiments C1-C10, wherein one or both primers in a primer set include a universal tag sequence.

C12. The method of any one of embodiments C1-C11, which further comprises contacting the extracellular nucleic acid with a control primer set under amplification conditions and detecting the presence or absence of a control amplification product from the control primer set, wherein the control primers of the control primer set can hybridize to the maternal nucleic acid.

C13. The method of embodiment C12, wherein the control primers of the control primer set hybridize to a nucleotide sequence that encodes or controls the expression of an albumin protein.

C14. The method of embodiment C13, wherein the control primer set comprises the following control primers:

| first primer | SEQ ID NO: | corresponding second primer | SEQ ID NO: |
|---|---|---|---|
| CAGTATCTTCAGCAGTGTCC | 175 | GCAAATTCAGTTACTTCATTC. | 176 |

C15. The method of any one of embodiments C12-C14, wherein detecting the presence or absence of the control amplification product comprises contacting under extension conditions each control amplification product with a control extension oligonucleotide and detecting extended control extension oligonucleotide.

C16. The method of embodiment C15, wherein the control extension oligonucleotide has the nucleotide sequence GCAGTGTCCATTTGAAGAT (SEQ ID NO: 71).

C17. The method of any one of embodiments C1-C16, wherein the extracellular nucleic acid is contacted with two or more primer sets in a multiplex reaction.

C18. The method of any one of embodiments C1-03, C5 and C7-C17, wherein the extracellular nucleic acid is contacted with the following primer sets

| first primer | SEQ ID NO: | corresponding second primer | SEQ ID NO: |
|---|---|---|---|
| AGATGGCTCTAGAGAATCCC | 104 | GCATTTTCCACTGGTATCCC | 137 |
| TTTCCTCTCTCTCCACCCC | 105 | AAAGTTGCCTTTCTGCCTGC | 138 |
| AGAGAAGGCGGATTCCTTTG | 106 | GAAGTTGGGAGAGTTACTCG | 139 |
| ACGAAGGGCTACTTCTCTAC | 107 | CTCTGGCTAGCATCACAATG | 136 |
| GAACCTCAGGCTCTTTGTCC | 108 | TCTATTCTTGCCGAGAGACC | 140 |
| ATGACCCCAAAAGCACAGAC | 109 | TCCCTCTGTGGTACAGAAAC | 141 |
| TCCCAGACTGAAATCCCAAG | 110 | TCGAATTTGATTCCCAGAGG | 142 |
| CTGGCCCTACGAATTTGTTG | 111 | GTCAGGAGATCGAGACAATC. | 143 |

C19. The method of any one of embodiments C1-C18, wherein the fetal nucleic acid is from a male fetus.

D1. A kit that comprises one or more primer sets selected from the group consisting of:

| first primer | SEQ ID NO: | corresponding second primer | SEQ ID NO: |
|---|---|---|---|
| AGATGGCTCTAGAGAATCCC | 104 | GCATTTTCCACTGGTATCCC | 137 |
| TTTCCTCTCTCTCCACCCC | 105 | AAAGTTGCCTTTCTGCCTGC | 138 |
| AGAGAAGGCGGATTCCTTTG | 106 | GAAGTTGGGAGAGTTACTCG | 139 |
| ACGAAGGGCTACTTCTCTAC | 107 | CTCTGGCTAGCATCACAATG | 136 |
| GAACCTCAGGCTCTTTGTCC | 108 | TCTATTCTTGCCGAGAGACC | 140 |
| ATGACCCCAAAAGCACAGAC | 109 | TCCCTCTGTGGTACAGAAAC | 141 |
| TCCCAGACTGAAATCCCAAG | 110 | TCGAATTTGATTCCCAGAGG | 142 |
| CTGGCCCTACGAATTTGTTG | 111 | GTCAGGAGATCGAGACAATC | 143 |
| ACCACAGCTGGCTAATTTTG | 112 | CTTGAGTCTGGGAGTTTGAG | 144 |
| TCCAGTAGTGCTGTTGAGAG | 113 | ACTAGGCACCTCATTCTCAG | 145 |
| AGTGTAAGCTCCCCTGTTTC | 114 | GGCATTCGTTGGTGATTATC | 146 |
| ATGGTGGCATTGACTGTGAC | 115 | CCTCATGAAGGGATATGTGC | 147 |
| AGTGACACAGGGAAAACACG | 116 | TTCTTTGGCTGAGAAAGGAC | 148 |
| GTGATGTGACAGCCTCAAAG | 117 | GTAGAGTAGAGTGACACTCC | 149 |
| CTTTTAGAGCGTAGACAAAC | 118 | GAGTCTTTCCTTCTTGTGCG | 150 |
| GAAAGACACGGGATTGGAAC | 119 | TGGAGGCAGAAAGAAGTGTC | 151 |
| AGATGGCTCTAGAGAATCCC | 104 | GCATTTTCCACTGGTATCCC | 137 |
| GCTACTGGGTCTAGCCTTAT | 120 | ATCAACAAACAAGGGGCTTC | 152 |
| TGGCTGGACAGCTTTCATAC | 121 | ACCCCCAATAGAAGTGATAG | 153 |

| first primer | SEQ ID NO: | corresponding second primer | SEQ ID NO: |
|---|---|---|---|
| TGGAAATGTGTTGGCTTGGG | 122 | TCATACGTAGAGTATCGGTG | 154 |
| CCCTGAAGGAATAAATGGAC | 123 | AGGCCAAATAGTCTTTACTC | 155 |
| TACCAAGGCATTGGACTCTG | 124 | GTCATCTGCACTAGGCATTC | 156 |
| TGTGGACCCCAGGATATAAC | 125 | AATTCAGAGCCTGACCCAAG | 157 |
| GGGTAAAGCATCTGCCAATG | 126 | GCATGCCTCCCTTGCTGTC | 158 |
| TGGAACATAGAGAGCACCAG | 127 | GCTCTCTACTTTACCTTCCC | 159 |
| ATGGGTCCTGATTCTTGCAC | 128 | TCAAGACTGTGAGGTGGTTG | 160 |
| TGACAAAGTCGACTCAGTGC | 129 | TGGAAGTTACAGGCCTTGAG | 161 |
| GCACACACAAATCATCCAAG | 130 | GACCATAGTCTCAGTATGCC | 162 |
| CAATGTTCACTGCCCATTCC | 131 | GGAAGTTTGTATAATTGCTCC | 163 |
| AATGATGCTTCAGTCCCACC | 132 | TCAACCAAGGGATGAAAGCC | 164 |
| CCGCTACACTTTGTATGACC | 133 | GCTTTTGCATAACTGAGCAC | 165 |
| TGTAACACTCAGAGCAAAGG | 134 | GTCAGGTACATACTAAAATGC | 166 |
| GATACTATGCCACCAAAGGG | 135 | CTGAATGAAAGTTCAAACGTC | 167 |
| CTCTGGCTAGCATCACAATG | 136 | TACCTTATGGCAGGGACTTG | 168 | wherein each primer set consists of a first primer and a corresponding second primer.

D2. The kit of embodiment D1, wherein the one or more primer sets are selected from the group consisting of

| first primer | SEQ ID NO: | corresponding second primer | SEQ ID NO: |
|---|---|---|---|
| AGATGGCTCTAGAGAATCCC | 104 | GCATTTTCCACTGGTATCCC | 137 |
| GATACTATGCCACCAAAGGG | 135 | CTGAATGAAAGTTCAAACGTC | 167 |
| CTCTGGCTAGCATCACAATG | 136 | TACCTTATGGCAGGGACTTG. | 168 |

D3. The kit of embodiment D1 or D2, which further comprises one or more extension oligonucleotides selected from the group consisting of:

| | SEQ ID NO: |
|---|---|
| CCAGAATGCGAAACTC | 68 |
| CCCATCTCTTCTCAATCC | 69 |
| AAACATGCTCACGATCAC | 70 |
| GCAGGGACTTGTCGCTAGG | 72 |
| AAAAAGCGCAGGTATTTTCTG | 73 |
| CAATTGGATCACATTACATCAAA | 74 |
| TGAAATCCCAAGACAATGGA | 169 |
| GGCCCTACGAATTTGTTGTATTTTT | 76 |
| GTCACATTTTGTTGCCCT | 77 |
| GGACTCTCAATGAAAGCA | 78 |
| GGAAGAATGCCAGAGTCA | 170 |
| TAGCCATAGTGCACATCTCA | 80 |
| CTCTTCACTGATTTTAAAGTTT | 81 |
| TGTCACCAAGCACACTATTGCCAGG | 82 |
| TAGAGCGTAGACAAACTGGATAGACA | 83 |
| TGGAACAGTTGCTGTGCCACCT | 171 |
| CCAGAATGCGAAACTC | 68 |
| GACATGAAGTCATTTGCT | 85 |
| AATTCGAGTTACAGCCACCG | 87 |

| | |
|---|---|
| 89 | CTGCACATGAGATACATATCTTCC |
| 90 | GTGGACCCCAGGATATAACAAATTA |
| 91 | CTGCCAATGAAATGTTAATTGCTGGGC |
| 92 | AGCAACCCAACCCTCTGC |
| 93 | GGCTCTTTCAGGAATGGA |
| 94 | TTGCACCTGTATCACACAGT |
| 95 | GTTCCCGAGAAACTAGGGATT |
| 96 | CCATTGACTGCTCAAATTTACA |
| 97 | GCCAGAGCCACAGAGGGCATTTT |
| 99 | GTCTCTTTTTATGAGCACA |
| 172 | GTAACACTCAGAGCAAAGGGGCACT |
| 101 | ACAGTACCTGTATTTCCTTAG |
| 173 | TATGGCAGGGACTTGTCGCTAGG. |
| 174 | |

D4. The kit of embodiment D3, wherein the one or more extension oligonucleotides are selected from the group consisting of

| | SEQ ID NO: |
|---|---|
| CCAGAATGCGAAACTC | 68 |
| ACAGTACCTGTATTTCCTTAG | 173 |
| TATGGCAGGGACTTGTCGCTAGG. | 174 |

D5. The kit of any one of embodiments D1-D4, wherein one or both primers in a primer set include a universal tag sequence.

D6. The kit of any one of embodiments D1-D5, which further comprises one or more control primer sets, wherein the control primers of the one or more control primer sets can hybridize to maternal nucleic acid under hybridization conditions.

D7. The kit of embodiment D6, wherein control primers of the one or more control primer sets hybridize to a nucleotide sequence that encodes or controls the expression of an albumin protein.

D8. The kit of embodiment D7, wherein the one or more control primer sets comprises the following control primers:

| first primer | SEQ ID NO: | corresponding second primer | SEQ ID NO: |
|---|---|---|---|
| CAGTATCTTCAGCAGTGTCC | 175 | GCAAATTCAGTTACTTCATTC. | 176 |

D9. The kit of any one of embodiments D6-D8, which further comprises one or more control extension oligonucleotides.

D10. The kit of embodiment D9, wherein the one or more control extension oligonucleotides comprises an oligonucleotide having the nucleotide sequence GCAGTGTC-CATTTGAAGAT (SEQ ID NO: 71).

D11. The kit of any one of embodiments D1, D3 and D5-D10, wherein the kit comprises the following primer sets

| first primer | SEQ ID NO: | corresponding second primer | SEQ ID NO: |
|---|---|---|---|
| AGATGGCTCTAGAGAATCCC | 104 | GCATTTTCCACTGGTATCCC | 137 |
| TTTCCTCTCTCTCCACCCC | 105 | AAAGTTGCCTTTCTGCCTGC | 138 |
| AGAGAAGGCGGATTCCTTTG | 106 | GAAGTTGGGAGAGTTACTCG | 139 |
| ACGAAGGGCTACTTCTCTAC | 107 | CTCTGGCTAGCATCACAATG | 136 |
| GAACCTCAGGCTCTTTGTCC | 108 | TCTATTCTTGCCGAGAGACC | 140 |
| ATGACCCCAAAAGCACAGAC | 109 | TCCCTCTGTGGTACAGAAAC | 141 |
| TCCCAGACTGAAATCCCAAG | 110 | TCGAATTTGATTCCCAGAGG | 142 |
| CTGGCCCTACGAATTTGTTG | 111 | GTCAGGAGATCGAGACAATC. | 143 |

D12. The kit of any one of embodiments D1-D1, which further comprises an enzyme.

D13. The kit of embodiment D12, wherein the enzyme is a polymerase.

D14. The kit of any one of embodiments D1-D13, which further comprises amplification components.

D15. The kit of any one of embodiments D1-D14, which further comprises one or more components for extracting nucleic acid from blood serum or blood plasma.

D16. The kit of any one of embodiments D1-D15, which further comprises instructions, or directions for accessing instructions, for carrying out a method described herein using the kit.

D17. A system that comprises a mass spectrometer and a kit described in any one of embodiments D1-D16.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, yet these modifications and improvements are within the scope and spirit of the invention.

The invention illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the invention claimed. The term "a" or "an" can refer to one of or a plurality of the elements it modifies (e.g., "a primer" can mean one or more primers) unless it is contextually clear either one of the elements or more than one of the elements is described. The term "about" as used herein refers to a value sometimes within 10% of the underlying parameter (i.e., plus or minus 10%), a value sometimes within 5% of the underlying parameter (i.e., plus or minus 5%), a value sometimes within 2.5% of the underlying parameter (i.e., plus or minus 2.5%), or a value sometimes within 1% of the underlying parameter (i.e., plus or minus 1%), and sometimes refers to the parameter with no variation. For example, a length of "about 100 nucleotides" can include lengths between 90 nucleotides and 110 nucleotides. Further, when a listing of values is described herein (e.g., 50%, 60%, 70%, 80%, 85%, 86%, 87%, 88%, 89%, 90%, 91%, 92%, 93% or 94%), the listing includes all intermediate values thereof (e.g., 62%, 67%). Thus, it should be understood that although the present invention has been specifically disclosed by representative embodiments and optional features, modification and variation of the concepts herein disclosed may be resorted to by those skilled in the art, and such modifications and variations are considered within the scope of this invention.

Embodiments of the invention are set forth in the claims that follow.

What is claimed is:

1. A method for identifying the presence or absence of Y-chromosome nucleic acid in extracellular nucleic acid from a pregnant female, which comprises:

(a) contacting under amplification conditions extracellular nucleic acid from a pregnant female with three or more primer sets selected from the group consisting of:

| first primer | SEQ ID NO: | corresponding second primer | SEQ ID NO: |
| --- | --- | --- | --- |
| AGATGGCTCTAGAGAATCCC | 104 | GCATTTTCCACTGGTATCCC | 137 |
| TTTCCTCTCTCTCCACCCC | 105 | AAAGTTGCCTTTCTGCCTGC | 138 |
| AGAGAAGGCGGATTCCTTTG | 106 | GAAGTTGGGAGAGTTACTCG | 139 |
| ACGAAGGGCTACTTCTCTAC | 107 | CTCTGGCTAGCATCACAATG | 136 |
| GAACCTCAGGCTCTTTGTCC | 108 | TCTATTCTTGCCGAGAGACC | 140 |
| ATGACCCCAAAAGCACAGAC | 109 | TCCCTCTGTGGTACAGAAAC | 141 |
| TCCCAGACTGAAATCCCAAG | 110 | TCGAATTTGATTCCCAGAGG | 142 |
| CTGGCCCTACGAATTTGTTG | 111 | GTCAGGAGATCGAGACAATC; | 143 | wherein (i) the nucleic acid comprises maternal nucleic acid and fetal nucleic acid, (ii) each primer of each primer set hybridizes to Y-chromosome nucleic acid, and (iii) each primer set consists of a first primer and a corresponding second primer; and (b) detecting the presence or absence of amplification products from three or more of the primer sets, whereby the presence of Y-chromosome nucleic acid is based on detecting the presence of the amplification products and whereby the absence of Y-chromosome nucleic acid is based on detecting the absence of the amplification products.

2. The method of claim 1, wherein the extracellular nucleic acid is deoxyribonucleic acid (DNA).

3. The method of claim 1, wherein the extracellular nucleic acid is ribonucleic acid (RNA).

4. The method of claim 1, wherein the extracellular nucleic acid is contacted with one or more first primer and corresponding second primer selected from the group consisting of:

| first primer | SEQ ID NO: | corresponding second primer | SEQ ID NO: |
|---|---|---|---|
| GATACTATGCCACCAAAGGG | 135 | CTGAATGAAAGTTCAAACGTC | 167 |
| CTCTGGCTAGCATCACAATG | 136 | TACCTTATGGCAGGGACTTG. | 168 |

5. The method of claim 1, wherein detecting the presence or absence of the amplification products comprises contacting under extension conditions amplification products with an extension oligonucleotide selected from the group consisting of:

| | SEQ ID NO: |
|---|---|
| CCAGAATGCGAAACTC | 68 |
| CCCATCTCTTCTCAATCC | 69 |
| AAACATGCTCACGATCAC | 70 |
| GCAGGGACTTGTCGCTAGG | 72 |
| AAAAAGCGCAGGTATTTTCTG | 73 |
| CAATTGGATCACATTACATCAAA | 74 |
| TGAAATCCCAAGACAATGGA | 169 |
| GGCCCTACGAATTTGTTGTATTTTT | 76 | and detecting the presence or absence of extended extension oligonucleotides.

6. The method of claim 4, wherein detecting the presence or absence of the amplification products comprises contacting under extension conditions amplification products with an extension oligonucleotide selected from the group consisting of:

| | SEQ ID NO: |
|---|---|
| ACAGTACCTGTATTTCCTTAG | 173 |
| TATGGCAGGGACTTGTCGCTAGG | 174 | and detecting the presence or absence of extended extension oligonucleotides.

7. The method of claim 5, wherein the extended extension oligonucleotides are detected by mass spectrometry.

8. The method of claim 6, wherein the extended extension oligonucleotides are detected by mass spectrometry.

9. The method of claim 1, wherein the extracellular nucleic acid is from blood serum.

10. The method of claim 1, wherein the extracellular nucleic acid is from blood plasma.

11. The method of claim 1, which further comprises determining the sex of the fetus based on the presence or absence of Y-chromosome nucleic acid, whereby the presence of Y-chromosome nucleic acid determines the fetus is male.

12. The method of claim 1, wherein the first primers or second corresponding primers or the first primers and second corresponding primers include universal tag sequences.

13. The method claim 1, wherein the extracellular nucleic acid is contacted with four or more of the primer sets.

14. The method claim 1, wherein the extracellular nucleic acid is contacted with five or more of the primer sets.

15. The method of claim 1, wherein the extracellular nucleic acid is contacted with six or more of the primer sets.

16. The method of claim 1, wherein the extracellular nucleic acid is contacted with seven or more of the primer sets.

17. The method of claim 1, wherein the extracellular nucleic acid is contacted with eight of the primer sets.

18. The method of claim 17, which further comprises contacting the extracellular nucleic acid with a control primer set under amplification conditions and detecting the presence or absence of a control amplification product from the control primer set, wherein the control primers of the control primer set can hybridize to the maternal nucleic acid.

19. The method of claim 18, wherein the control primers of the control primer set hybridize to a nucleotide sequence that encodes or controls the expression of an albumin protein.

20. The method of claim 19, wherein the control primer set comprises the following control primers:

| first primer | SEQ ID NO: | corresponding second primer | SEQ ID NO: |
|---|---|---|---|
| CAGTATCTTCAGCAGTGTCC | 175 | GCAAATTCAGTTACTTCATTC. | 176 |

21. The method of claim 18, wherein detecting the presence or absence of the control amplification product comprises contacting under extension conditions each control amplification product with a control extension oligonucleotide and detecting extended control extension oligonucleotide.

22. The method of claim 21, wherein the control extension oligonucleotide has the nucleotide sequence GCAGTGTCCATTTGAAGAT (SEQ ID NO: 71).

23. A kit that comprises three or more primer sets selected from the group consisting of:

| first primer | SEQ ID NO: | corresponding second primer | SEQ ID NO: |
|---|---|---|---|
| AGATGGCTCTAGAGAATCCC | 104 | GCATTTTCCACTGGTATCCC | 137 |
| TTTCCTCTCTCTCCACCCC | 105 | AAAGTTGCCTTTCTGCCTGC | 138 |
| AGAGAAGGCGGATTCCTTTG | 106 | GAAGTTGGGAGAGTTACTCG | 139 |
| ACGAAGGGCTACTTCTCTAC | 107 | CTCTGGCTAGCATCACAATG | 136 |
| GAACCTCAGGCTCTTTGTCC | 108 | TCTATTCTTGCCGAGAGACC | 140 |

| first primer | SEQ ID NO: | corresponding second primer | SEQ ID NO: |
|---|---|---|---|
| ATGACCCCAAAAGCACAGAC | 109 | TCCCTCTGTGGTACAGAAAC | 141 |
| TCCCAGACTGAAATCCCAAG | 110 | TCGAATTTGATTCCCAGAGG | 142 |
| CTGGCCCTACGAATTTGTTG | 111 | GTCAGGAGATCGAGACAATC | 143 | wherein the primers comprise a 5' tag sequence.

24. The kit of claim 23, comprising eight of the primer sets.

25. A method for determining the amount of fetal nucleic acid in a sample of extracellular nucleic acid from a pregnant female, which comprises:

(a) contacting under amplification conditions extracellular nucleic acid from a pregnant female with three or more primer sets selected from the group consisting of:

| first primer | SEQ ID NO: | corresponding second primer | SEQ ID NO: |
|---|---|---|---|
| AGATGGCTCTAGAGAATCCC | 104 | GCATTTTCCACTGGTATCCC | 137 |
| TTTCCTCTCTCTCCACCCC | 105 | AAAGTTGCCTTTCTGCCTGC | 138 |
| AGAGAAGGCGGATTCCTTTG | 106 | GAAGTTGGGAGAGTTACTCG | 139 |
| ACGAAGGGCTACTTCTCTAC | 107 | CTCTGGCTAGCATCACAATG | 136 |
| GAACCTCAGGCTCTTTGTCC | 108 | TCTATTCTTGCCGAGAGACC | 140 |
| ATGACCCCAAAAGCACAGAC | 109 | TCCCTCTGTGGTACAGAAAC | 141 |
| TCCCAGACTGAAATCCCAAG | 110 | TCGAATTTGATTCCCAGAGG | 142 |
| CTGGCCCTACGAATTTGTTG | 111 | GTCAGGAGATCGAGACAATC; | 143 |

(b) detecting the amount of amplification products from three or more of the primer sets, whereby the amount of fetal nucleic acid in the extracellular nucleic acid is determined based on the amount of the amplification product.

26. The method of claim 25, wherein detecting the amount of the amplification products comprises contacting under extension conditions amplification products with an extension oligonucleotide selected from the group consisting of:

| | SEQ ID NO: |
|---|---|
| CCAGAATGCGAAACTC | 68 |
| CCCATCTCTTCTCAATCC | 69 |
| AAACATGCTCACGATCAC | 70 |
| GCAGGGACTTGTCGCTAGG | 72 |
| AAAAAGCGCAGGTATTTTCTG | 73 |
| CAATTGGATCACATTACATCAAA | 74 |
| TGAAATCCCAAGACAATGGA | 169 |
| GGCCCTACGAATTTGTTGTATTTTT | 76 | and detecting the amount of extended extension oligonucleotides.

27. The kit of claim 23, wherein the 5' tag sequence comprises a universal primer sequence.

* * * * *

SEQUENCE LISTING

```
<160> NUMBER OF SEQ ID NOS: 186

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
acgttggatg gcattttcca ctggtatccc                                      30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
acgttggatg aaagttgcct ttctgcctgc                                      30

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 3
acgttggatg gaagttggga gagttactcg                30

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
acgttggatg gcaaattcag ttacttcatt c               31

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
acgttggatg ctctggctag catcacaatg                30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
acgttggatg tctattcttg ccgagagacc                30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
acgttggatg tccctctgtg gtacagaaac                30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
acgttggatg tcgaatttga ttcccagagg                30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
acgttggatg gtcaggagat cgagacaatc                                              30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
acgttggatg cttgagtctg ggagtttgag                                              30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
acgttggatg actaggcacc tcattctcag                                              30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
acgttggatg ggcattcgtt ggtgattatc                                              30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
acgttggatg cctcatgaag ggatatgtgc                                              30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
acgttggatg ttctttggct gagaaaggac                                              30

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
acgttggatg gtagagtaga gtgacactcc                                              30

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
acgttggatg gagtctttcc ttcttgtgcg                                       30

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
acgttggatg tggaggcaga aagaagtgtc                                       30

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
acgttggatg atcaacaaac aagggcttc                                        30

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
acgttggatg accccaata gaagtgatag                                        30

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
acgttggatg tcatacgtag agtatcggtg                                       30

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
acgttggatg aggccaaata gtctttactc                                       30

```
<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
acgttggatg gtcatctgca ctaggcattc                                      30

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
acgttggatg aattcagagc ctgacccaag                                      30

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
acgttggatg gcatgcctcc cttgctgtc                                       29

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
acgttggatg gctctctact ttaccttccc                                      30

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
acgttggatg tcaagactgt gaggtggttg                                      30

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
acgttggatg tggaagttac aggccttgag                                      30

<210> SEQ ID NO 28
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
acgttggatg gaccatagtc tcagtatgcc                                          30

<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
acgttggatg ggaagtttgt ataattgctc c                                        31

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
acgttggatg tcaaccaagg gatgaaagcc                                          30

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
acgttggatg gcttttgcat aactgagcac                                          30

<210> SEQ ID NO 32
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
acgttggatg gtcaggtaca tactaaaatg c                                        31

<210> SEQ ID NO 33
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
acgttggatg ctgaatgaaa gttcaaacgt c                                        31

<210> SEQ ID NO 34
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 34
acgttggatg taccttatgg cagggacttg                                        30

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
acgttggatg agatggctct agagaatccc                                        30

<210> SEQ ID NO 36
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
acgttggatg tttcctctct ctccacccc                                         29

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
acgttggatg agagaaggcg gattcctttg                                        30

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
acgttggatg cagtatcttc agcagtgtcc                                        30

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
acgttggatg acgaagggct acttctctac                                        30

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic
```

```
                                        primer

<400> SEQUENCE: 40
acgttggatg gaacctcagg ctctttgtcc                                         30

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
acgttggatg atgaccccaa aagcacagac                                         30

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
acgttggatg tcccagactg aaatcccaag                                         30

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
acgttggatg ctggccctac gaatttgttg                                         30

<210> SEQ ID NO 44
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
acgttggatg accacagctg gctaattttg                                         30

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
acgttggatg tccagtagtg ctgttgagag                                         30

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 46
acgttggatg agtgtaagct cccctgtttc                                    30

<210> SEQ ID NO 47
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
acgttggatg atggtggcat tgactgtgac                                    30

<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
acgttggatg agtgacacag ggaaaacacg                                    30

<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
acgttggatg gtgatgtgac agcctcaaag                                    30

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
acgttggatg cttttagagc gtagacaaac                                    30

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
acgttggatg gaaagacacg ggattggaac                                    30

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
```
acgttggatg gctactgggt ctagcctttat                          30

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
acgttggatg tggctggaca gctttcatac                           30

<210> SEQ ID NO 54
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
acgttggatg tggaaatgtg ttggcttggg                           30

<210> SEQ ID NO 55
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
acgttggatg ccctgaagga ataaatggac                           30

<210> SEQ ID NO 56
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
acgttggatg taccaaggca ttggactctg                           30

<210> SEQ ID NO 57
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
acgttggatg tgtggacccc aggatataac                           30

<210> SEQ ID NO 58
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
acgttggatg gggtaaagca tctgccaatg                           30

<210> SEQ ID NO 59
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
acgttggatg tggaacatag agagcaccag                                    30

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
acgttggatg atgggtcctg attcttgcac                                    30

<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
acgttggatg tgacaaagtc gactcagtgc                                    30

<210> SEQ ID NO 62
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
acgttggatg gcacacacaa atcatccaag                                    30

<210> SEQ ID NO 63
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
acgttggatg caatgttcac tgcccattcc                                    30

<210> SEQ ID NO 64
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
acgttggatg aatgatgctt cagtcccacc                                    30

<210> SEQ ID NO 65

```
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
acgttggatg ccgctacact ttgtatgacc                                     30

<210> SEQ ID NO 66
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
acgttggatg tgtaacactc agagcaaagg                                     30

<210> SEQ ID NO 67
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
acgttggatg gatactatgc caccaaaggg                                     30

<210> SEQ ID NO 68
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ccagaatgcg aaactc                                                    16

<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
cccatctctt ctcaatcc                                                  18

<210> SEQ ID NO 70
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
aaacatgctc acgatcac                                                  18

<210> SEQ ID NO 71
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 71
gcagtgtcca tttgaagat                                                  19

<210> SEQ ID NO 72
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gcagggactt gtcgctagg                                                  19

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
aaaaagcgca ggtattttct g                                               21

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
caattggatc acattacatc aaa                                             23

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
ggggtgaaat cccaagacaa tgga                                            24

<210> SEQ ID NO 76
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
ggccctacga atttgttgta ttttt                                           25

<210> SEQ ID NO 77
<211> LENGTH: 18
<212> TYPE: DNA
<213> ORGANISM: Artificial Sequence
<220> FEATURE:
```

-continued

<223> OTHER INFORMATION: Description of Artificial Sequence: Synthetic
      primer

<400> SEQUENCE: 77
gtcacatttt gttgccct                                                 18

<210> SEQ ID NO 78
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
ggactctcaa tgaaagca                                                 18

<210> SEQ ID NO 79
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
tggaagaatg ccagagtca                                                19

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
tagccatagt gcacatctca                                               20

<210> SEQ ID NO 81
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ctcttcactg attttaaagt tt                                            22

<210> SEQ ID NO 82
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
tgtcaccaag cacactattg ccagg                                         25

<210> SEQ ID NO 83
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 83
tagagcgtag acaaactgga tagaca                                              26

<210> SEQ ID NO 84
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
cccagtggaa cagttgctgt gccacct                                             27

<210> SEQ ID NO 85
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
gacatgaagt catttgct                                                       18

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
cgcagtgtcc atttgaagat                                                     20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
aattcgagtt acagccaccg                                                     20

<210> SEQ ID NO 88
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
gtatcctgaa gccaataaat ac                                                  22

<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
```

```
gaaggaataa atggactctc gat                                        23
```

<210> SEQ ID NO 90
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90

```
ctgcacatga gatacatatc ttcc                                       24
```

<210> SEQ ID NO 91
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91

```
gtggacccca ggatataaca aatta                                      25
```

<210> SEQ ID NO 92
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92

```
ctgccaatga aatgttaatt gctgggc                                    27
```

<210> SEQ ID NO 93
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93

```
agcaacccaa ccctctgc                                              18
```

<210> SEQ ID NO 94
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94

```
ggctctttca ggaatgga                                              18
```

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95

```
ttgcacctgt atcacacagt                                            20
```

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
gttcccgaga aactagggat t                                              21

<210> SEQ ID NO 97
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
ccattgactg ctcaaattta ca                                             22

<210> SEQ ID NO 98
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
tccgcagtgt ccatttgaag at                                             22

<210> SEQ ID NO 99
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
gccagagcca cagagggcat ttt                                            23

<210> SEQ ID NO 100
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
ccccggtctc tttttatgag caca                                           24

<210> SEQ ID NO 101
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
gtaacactca gagcaaaggg gcact                                          25

<210> SEQ ID NO 102
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 102
gacagtacct gtatttcctt ag                                             22

<210> SEQ ID NO 103
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 103
gtatggcagg gacttgtcgc tagg                                           24

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 104
agatggctct agagaatccc                                                20

<210> SEQ ID NO 105
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 105
tttcctctct ctccacccc                                                 19

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 106
agagaaggcg gattcctttg                                                20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 107
acgaagggct acttctctac                                                20

<210> SEQ ID NO 108
<211> LENGTH: 20

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
gaacctcagg ctctttgtcc                                            20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
atgaccccaa aagcacagac                                            20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
tcccagactg aaatcccaag                                            20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
ctggccctac gaatttgttg                                            20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
accacagctg gctaattttg                                            20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
tccagtagtg ctgttgagag                                            20

<210> SEQ ID NO 114
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 114
agtgtaagct cccctgtttc                                                20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
atggtggcat tgactgtgac                                                20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
agtgacacag ggaaaacacg                                                20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
gtgatgtgac agcctcaaag                                                20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
cttttagagc gtagacaaac                                                20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
gaaagacacg ggattggaac                                                20

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 120
gctactgggt ctagccttat                                           20

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
tggctggaca gctttcatac                                           20

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
tggaaatgtg ttggcttggg                                           20

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
ccctgaagga ataaatggac                                           20

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
taccaaggca ttggactctg                                           20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
tgtggacccc aggatataac                                           20

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 126
gggtaaagca tctgccaatg                                              20

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
tggaacatag agagcaccag                                              20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
atgggtcctg attcttgcac                                              20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
tgacaaagtc gactcagtgc                                              20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
gcacacacaa atcatccaag                                              20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
caatgttcac tgcccattcc                                              20

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
```

```
aatgatgctt cagtcccacc                                                    20
```

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133

```
ccgctacact ttgtatgacc                                                    20
```

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134

```
tgtaacactc agagcaaagg                                                    20
```

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135

```
gatactatgc caccaaaggg                                                    20
```

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136

```
ctctggctag catcacaatg                                                    20
```

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137

```
gcattttcca ctggtatccc                                                    20
```

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138

```
aaagttgcct ttctgcctgc                                                    20
```

-continued

```
<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
gaagttggga gagttactcg                                           20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
tctattcttg ccgagagacc                                           20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
tccctctgtg gtacagaaac                                           20

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
tcgaatttga ttcccagagg                                           20

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
gtcaggagat cgagacaatc                                           20

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
cttgagtctg ggagtttgag                                           20

<210> SEQ ID NO 145
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
actaggcacc tcattctcag                                                 20

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
ggcattcgtt ggtgattatc                                                 20

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
cctcatgaag ggatatgtgc                                                 20

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
ttctttggct gagaaaggac                                                 20

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
gtagagtaga gtgacactcc                                                 20

<210> SEQ ID NO 150
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
gagtctttcc ttcttgtgcg                                                 20

<210> SEQ ID NO 151
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 151
tggaggcaga aagaagtgtc                                                 20

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
atcaacaaac aaggggcttc                                                 20

<210> SEQ ID NO 153
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
acccccaata gaagtgatag                                                 20

<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
tcatacgtag agtatcggtg                                                 20

<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
aggccaaata gtctttactc                                                 20

<210> SEQ ID NO 156
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
gtcatctgca ctaggcattc                                                 20

<210> SEQ ID NO 157
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 157
aattcagagc ctgacccaag                                              20

<210> SEQ ID NO 158
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
gcatgcctcc cttgctgtc                                               19

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
gctctctact ttaccttccc                                              20

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
tcaagactgt gaggtggttg                                              20

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
tggaagttac aggccttgag                                              20

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
gaccatagtc tcagtatgcc                                              20

<210> SEQ ID NO 163
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 163
ggaagtttgt ataattgctc c                                              21

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
tcaaccaagg gatgaaagcc                                                20

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
gcttttgcat aactgagcac                                                20

<210> SEQ ID NO 166
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
gtcaggtaca tactaaaatg c                                              21

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
ctgaatgaaa gttcaaacgt c                                              21

<210> SEQ ID NO 168
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
taccttatgg cagggacttg                                                20

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169

```
tgaaatccca agacaatgga                                              20
```

<210> SEQ ID NO 170
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170

```
ggaagaatgc cagagtca                                                18
```

<210> SEQ ID NO 171
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171

```
tggaacagtt gctgtgccac ct                                           22
```

<210> SEQ ID NO 172
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172

```
gtctcttttt atgagcaca                                               19
```

<210> SEQ ID NO 173
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173

```
acagtacctg tatttcctta g                                            21
```

<210> SEQ ID NO 174
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174

```
tatggcaggg acttgtcgct agg                                          23
```

<210> SEQ ID NO 175
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175

```
cagtatcttc agcagtgtcc                                              20
```

<210> SEQ ID NO 176
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
gcaaattcag ttacttcatt c                                             21

<210> SEQ ID NO 177
<211> LENGTH: 301
<212> TYPE: DNA
<213> ORGANISM: Unknown
<220> FEATURE:
<223> OTHER INFORMATION: Description of Unknown: CDY1-1 polynucleotide

<400> SEQUENCE: 177
tatggagtac ttcagggtag aatggacaga tactcaaaag cagtatgaac aaacaaagat    60
taaggtaaag ataaatacat gaacaaatat gtaagataaa aaatttggct gggctcagtg   120
gctcacacct gtaatcccag catttggga ggctgaggtg cttggatcac gaggtcagga    180
gatcgagaca atcctggcta acatggtgaa accccgtctc tactaaaaat acaacaaatt   240
cgtagggcca ggtggcaggt gcctgtagtc tcagctactc gggaggctga gacaggagaa   300
t                                                                   301

<210> SEQ ID NO 178
<211> LENGTH: 301
<212> TYPE: DNA
<213> ORGANISM: Unknown
<220> FEATURE:
<223> OTHER INFORMATION: Description of Unknown: HSFY-1 polynucleotide

<400> SEQUENCE: 178
cctttgcctt tgtgtccaca gaggtttctg tattccaccg tgcaggtgca aaacatacac    60
cagagcagaa aagcagtttg ttcttcctct ttgtttctaa atatagaggt gcttaaacaa   120
catccctatt ttgagattac tattccataa aagaaaacaa tctcatctta gagtaacttt   180
cacttcttgt tctagcaaag agaaagttgc ctttctgcct gcagaaatta tcaaacgcct   240
cttttgtatt ttaatttcat gagaaggatt gagaagagat ggggggtgga gagagaggaa   300
a                                                                   301

<210> SEQ ID NO 179
<211> LENGTH: 301
<212> TYPE: DNA
<213> ORGANISM: Unknown
<220> FEATURE:
<223> OTHER INFORMATION: Description of Unknown: RBMY1A1-1
      polynucleotide

<400> SEQUENCE: 179
ggccaggcga acctcaggct ctttgtccta ctaaaaagcg caggtatttt ctgtttctct    60
ggacagctgg gtctctcggc aagaatagaa agcgaaggtt tgggattttg tctataaaag   120
gggatgggtt ttctatgtgt gggtgttgaa ttacgggagg agtcagtggg gaaagaactc   180
ctcagtgcta ttaagagact cactttcgtt aaactcattg attttcctg aggattctac    240 ctttaactgc ctaatgtgtc cgactagttg tgggagatgg tgctaagccg ccattggttt   300
t                                                                   301

```
<210> SEQ ID NO 180
<211> LENGTH: 301
<212> TYPE: DNA
<213> ORGANISM: Unknown
<220> FEATURE:
<223> OTHER INFORMATION: Description of Unknown: RBMY2-1 polynucleotide

<400> SEQUENCE: 180
caatgcagaa ataacatttc aattttgat ttgcaaacaa ggattggtat gcaataacta      60
ttattttcaa tgcttgcttt aatatctgct cgagtctcct ttttcagatc gactctcccc    120
accatctact atagatgcca cataacttga gctaccatat gcttcacgag gatcagggag    180
caccctaccc agagaaggcg gattcctttg gtcttttctg caaacatgct cacgatcaca    240
ataatgaaaa tcaccacagc tcgagtaact ctcccaactt ctgccatatc tatctcgtgt    300
a                                                                    301

<210> SEQ ID NO 181
<211> LENGTH: 301
<212> TYPE: DNA
<213> ORGANISM: Unknown
<220> FEATURE:
<223> OTHER INFORMATION: Description of Unknown: TTTY16-1 polynucleotide

<400> SEQUENCE: 181
gccactcttc tagaaagaac agaagaacac cacaaccaag aacagaaata taccagtgtt     60
taattgtctt tcagccaatc caaggagaga cactatcatt catctctacc gggcctatta    120
aatttacctc gaatttgatt cccagaggag ttggtgcttc acatcatcag ggggaacttc    180
tccattgtct tgggatttca gtctgggata gagactttga acagcaataa ggtaataagg    240
tcagataggg gtggggatac ccctctggtg aggggtggat gccatgctgt accttcacct    300
g                                                                    301

<210> SEQ ID NO 182
<211> LENGTH: 301
<212> TYPE: DNA
<213> ORGANISM: Unknown
<220> FEATURE:
<223> OTHER INFORMATION: Description of Unknown: TTTY22-1 polynucleotide

<400> SEQUENCE: 182
accaatgcaa tgcactagtc tcagggcacc aggcctgagc tgtgagctct ggctagcatc     60
acaatgaatg ccaccattgc ctagcgacaa gtccctgcca taaggtagag aagtagccct    120
tcgtggaggt gcacagacca tggattcttg ccttcttctg tgtggggtcc acaggatatt    180
cccatagttc taggagagga cagacattag cctgcctaaa gaaacatcaa gcagagcccc    240
aggaataaac tgtggaattc ctaacgattc aaaaagattt gcaggatgca tcagacctgc    300
c                                                                    301

<210> SEQ ID NO 183
<211> LENGTH: 198
<212> TYPE: DNA
<213> ORGANISM: Unknown
<220> FEATURE:
<223> OTHER INFORMATION: Description of Unknown: SRY-4-i polynucleotide

<400> SEQUENCE: 183
acgtccagga tagagtgaag cgacccatga acgcattcat cgtgtggtct cgcgatcaga     60
ggcgcaagat ggctctagag aatcccagaa tgcgaaactc agagatcagc aagcagctgg    120
```

```
gataccagtg gaaaatgctt actgaagccg aaaaatggcc attcttccag gaggcacaga    180
aattacaggc catgcaca                                                  198

<210> SEQ ID NO 184
<211> LENGTH: 301
<212> TYPE: DNA
<213> ORGANISM: Unknown
<220> FEATURE:
<223> OTHER INFORMATION: Description of Unknown: XKRY-1 polynucleotide

<400> SEQUENCE: 184 tatatcctttt gagtacgtat ctggaagtag agtagctgga ttatgtggta attcttattt    60
ttaatttaac tgtattttttg aacactcaat tctatgaccc caaaagcaca gactagaaaa   120
gcacaacaaa aaacaattgg atcacattac atcaaactaa aatgtttctg taccacagag   180
ggaaaagggt gaaaagcaaa tgttcactga tagtgtatat gctatattac aagcacttat   240
taaattaaag gtataggttc caaaatgtac taggtgaaaa atgtattatg gttatttttt   300
c                                                                    301

<210> SEQ ID NO 185
<211> LENGTH: 68
<212> TYPE: DNA
<213> ORGANISM: Unknown
<220> FEATURE:
<223> OTHER INFORMATION: Description of Unknown: Alb-2-i oligonucleotide

<400> SEQUENCE: 185
gctcagtatc ttcagcagtg tccatttgaa gatcatgtaa aattagtgaa tgaagtaact    60
gaatttgc                                                             68

<210> SEQ ID NO 186
<211> LENGTH: 10
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 186
acgttggatg                                                           10
```